(12) United States Patent
Yang et al.

(10) Patent No.: US 12,410,166 B2
(45) Date of Patent: Sep. 9, 2025

(54) SULFONYLAMIDINE SUBSTITUTED COMPOUNDS AND THEIR USE AS BETA-LACTAMASE INHIBITORS

(71) Applicant: NINGXIA ACADEMY OF AGRICULTURE AND FORESTRY SCIENCES, Ningxia (CN)

(72) Inventors: Zhixiang Yang, Ningxia (CN); Haikang Yang, Ningxia (CN); Jinbo Ji, Ningxia (CN); Lijuan Zhai, Ningxia (CN); Jian Sun, Ningxia (CN); Jingwen Ji, Ningxia (CN); Lili He, Ningxia (CN); Dong Tang, Ningxia (CN); Zafar Iqbal, Ningxia (CN); Yuanbai Liu, Ningxia (CN); Yangxiu Mu, Ningxia (CN); Xueqin Ma, Ningxia (CN); Jianqiang Yu, Ningxia (CN)

(73) Assignee: NINGXIA ACADEMY OF AGRICULTURE AND FORESTRY SCIENCES, Ningxia (CN)

( * ) Notice: Subject to any disclaimer, the term of this patent is extended or adjusted under 35 U.S.C. 154(b) by 203 days.

(21) Appl. No.: 18/040,129

(22) PCT Filed: Mar. 4, 2022

(86) PCT No.: PCT/CN2022/079306
§ 371 (c)(1),
(2) Date: Jan. 31, 2023

(87) PCT Pub. No.: WO2022/233181
PCT Pub. Date: Nov. 10, 2022

(65) Prior Publication Data
US 2024/0132488 A1    Apr. 25, 2024

(30) Foreign Application Priority Data

May 7, 2021  (WO) ................ PCT/CN2021/092095

(51) Int. Cl.
| | |
|---|---|
| *C07D 471/04* | (2006.01) |
| *A61K 31/407* | (2006.01) |
| *A61K 31/437* | (2006.01) |
| *A61K 31/444* | (2006.01) |
| *A61K 31/4545* | (2006.01) |
| *A61K 31/497* | (2006.01) |
| *A61P 31/04* | (2006.01) |

(52) U.S. Cl.
CPC .......... *C07D 471/04* (2013.01); *A61K 31/407* (2013.01); *A61K 31/437* (2013.01); *A61K 31/444* (2013.01); *A61K 31/4545* (2013.01); *A61K 31/497* (2013.01); *A61P 31/04* (2018.01)

(58) Field of Classification Search
CPC ..................................................... C07D 471/04
USPC ..................................................... 514/210.16
See application file for complete search history.

(56) References Cited

FOREIGN PATENT DOCUMENTS

| WO | WO 2020030761 A1 | 2/2020 |
| WO | WO 2022/047790 A1 | 3/2022 |

OTHER PUBLICATIONS

Iqbal et al., Beilstein Journal of Organic Chemistry, (2021), 17, 711-718.*
Gao, Yuanyu et al. "Amidine Derivatives of Avibactam: Synthesis and In Vitro β-Lactamase Inhibition Activity"; *ChemistrySelect*, vol. 6, No. 5, Feb. 3, 2021 (Feb. 3, 2021); pp. 1174-1178.
Iqbal Zafar, et al. "β-Lactamase inhibition profile of new amidine-substituted diazabicyclooctanes"; *Beilstein J. Org. Chem.*, vol. 17, Mar. 12, 2021 (Mar. 12, 2021); pp. 711-718.
Ji, Jingwen, et al. "Sulfonylamidine-substituted derivatives of avibactam:Synthesis and antibacterial activity"; *J. Heterocyclic Chem.*, vol. 58. No. 12, Sep. 10, 2021 (Sep. 10, 2021); pp. 2390-2394.
Liu, Yuanbai, et al. "Substituted-amidine derivatives of diazabicyclooctane as prospective [beta]-Lactamase inhibitors"; *Monatshefte Fur Chemie, Chem. Monthly*, vol. 153 No. 3, Feb. 12, 2022; pp. 301-309.

* cited by examiner

Primary Examiner — Niloofar Rahmani
(74) Attorney, Agent, or Firm — Haynes and Boone, LLP

(57) ABSTRACT

The present invention belongs to the medical field, and relates to novel β-lactamase inhibitors, for the treatment of bacterial infections in combination with β-lactam antibiotics, including infection caused by drug resistant organisms and especially multi-drug resistant organisms. The present invention includes compounds according to formula (I): or pharmaceutically acceptable salts thereof, wherein M and R are as defined herein.

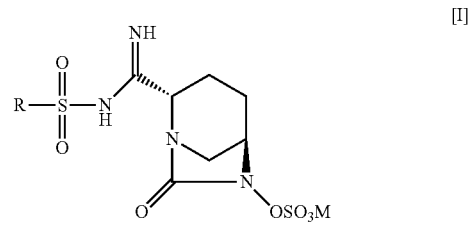

18 Claims, No Drawings

SULFONYLAMIDINE SUBSTITUTED COMPOUNDS AND THEIR USE AS BETA-LACTAMASE INHIBITORS

CROSS-REFERENCE TO RELATED APPLICATION

This application claims priority to PCT International Application No. PCT/CN2022/079306, filed Mar. 4, 2022, which claims the benefit of and priority to PCT/CN2021/092095, filed May 7, 2021, the entire contents of each of which is hereby incorporated herein in its entirety by express reference thereto.

FIELD OF THE INVENTION

This invention relates to novel beta-lactamase inhibitors and their preparation and their use as antibacterial agents either alone or in combination with an antibiotic (or plural antibiotics) for the treatment of infections caused by β-lactamase-producing pathogenic bacteria. More particularly, the invention relates to compositions and methods for overcoming bacterial antibiotic resistance.

BACKGROUND OF THE INVENTION

Microbial drug resistance to β-lactam antibiotics, especially in Gram-negative bacterial, is most commonly mediated by β-lactamases. β-lactamases are enzymes that catalyze the hydrolysis of the β-lactam ring, which inactivate the antibacterial activity of the β-lactam antibiotic and allow the bacterial to become resistant. Inhibition of the β-lactamase with a β-lactamases inhibitor slows or prevents degradation of the β-lactam antibiotic and restores β-lactam antibiotic susceptibility to β-lactamase producing bacteria. Many of these β-lactamases are not effectively inhibited by β-lactamase inhibitors currently on the market rendering the β-lactam antibiotics ineffective in treating bacteria that producing these β-lactamases. There is an urgent need for novel β-lactamase inhibitors that inhibit β-lactamases that are not effectively inhibited by the current clinical β-lactamases (e.g. KPC, class C and class D β-lactamases) and that could be used in combination with β-lactam antibiotics to treat infection caused by β-lactam resistant bacteria.

Recently, certain diazabicyclic compounds have been disclosed in WO 2009/091856 which is hereby incorporated by reference in its entirety. In addition, a number of diazabicyclic heterocycles have been disclosed in the following patents or applications as β-lactamase inhibitors: US 2003/0199541 A1, US 2004/0157826 A1, US 2004/0097490 A1, US 2005/0020572 A1, US 2006/7112592 B2, US 2006/0189652 A1, US 2008/7439253 B2, US 2009/0018329 A1, EP 1307457 B1, EP 1537117 B1, WO 2002/100860 A2, WO 2002/10172 A1, WO 2003/063864 A2, WO 2004/052891 A1, WO 2004/022563 A1, WO 2008/142285 A1, WO 2009/090320 A1, US 2010/0092443 A1, WO 2010/126820 A2, WO 2013/038330 A1, US 2015/0031666 A1, US 2015/0239840 A1, US 2016/0297817 A1, US2016/0002235 A1, WO 2017037607 A1, WO 2018053057 A2, WO 2018053215 A1, WO2018060481A1, WO2018060484A1, WO2018208769A1.

DETAILED DESCRIPTION OF THE INVENTION

In one aspect, the present invention relates to new diazabicyclic compounds (some of which have potent broad-spectrum β-lactamase inhibitory activity and others do not have such activity) that when used in combination with a β-lactam antibiotic or with other non β-lactam antibiotic enhance the activity of the antibiotic against class A, class B, class C, and class D enzyme producing organisms and thereby enhance the antibacterial properties. The inventive compounds are therefore useful in the treatment of bacterial infections in humans or animals either alone or in combination with β-lactam antibiotics.

In accordance with the present invention, there are provided (A) new compounds of general formula (I), (B) pharmaceutically acceptable salts of the compounds of formula (I), and (C) pharmaceutically acceptable solvates of the compounds of formula (I) and of their salts, and (D) deuterated compounds of compounds of (A), (B) and (C), (namely, (i) compounds of formula (I) modified in that they have been deuterated, (ii) pharmaceutically acceptable salts of the compounds of formula (I) modified in that they have been deuterated, (iii) pharmaceutically acceptable solvates of the compounds of formula (I) and of their salts modified in that they have been deuterated):

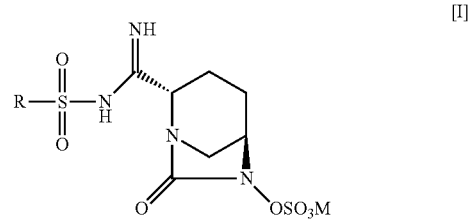

wherein:

M is hydrogen or a pharmaceutically acceptable salt forming cation, a "pharmaceutically acceptable salt" refers to a salt of a compound, which salt possesses the desired pharmacological activity of the parent compound, specified compounds "modified in that they have been deuterated" refer to compounds prepared by modifying the specified compounds so that one or more hydrogen atoms in the compound have been replaced with or converted to deuterium, R is optionally substituted with one or two substituents independently selected from the following:

Lower alkyl, amine, substituted amine, alkoxy, hydroxyalkyl, halogen, hydroxy, carboxy, alkoxycarbonyl, haloalkyl, trifluoromethyl, trifluoromethyloxy, alkylamine, substituted alkylamine, carboxamide, thiocarboxamide, sulfonic acid, sulphate, acylamino, sulfonylamino, substituted or unsubstituted sulfonamide, substituted or unsubstituted urea, substituted or unsubstituted thiourea, oxyimino, hydroxamic acid, acyl, trifluoromethyl carbonyl, cyano, amidino, guanidino, aryloxy, heterocyclylalkyloxy, and heteroaryloxy.

The compounds of the present invention are new and the structural features are significantly distinct from the compounds described in the prior art.

In the formula (I), R is a radical selected from any of the following groups:

(1) $C_{1-6}$ straight, or branched chain alkyl or amino which is optionally substituted. Non-limiting examples of such compounds are:

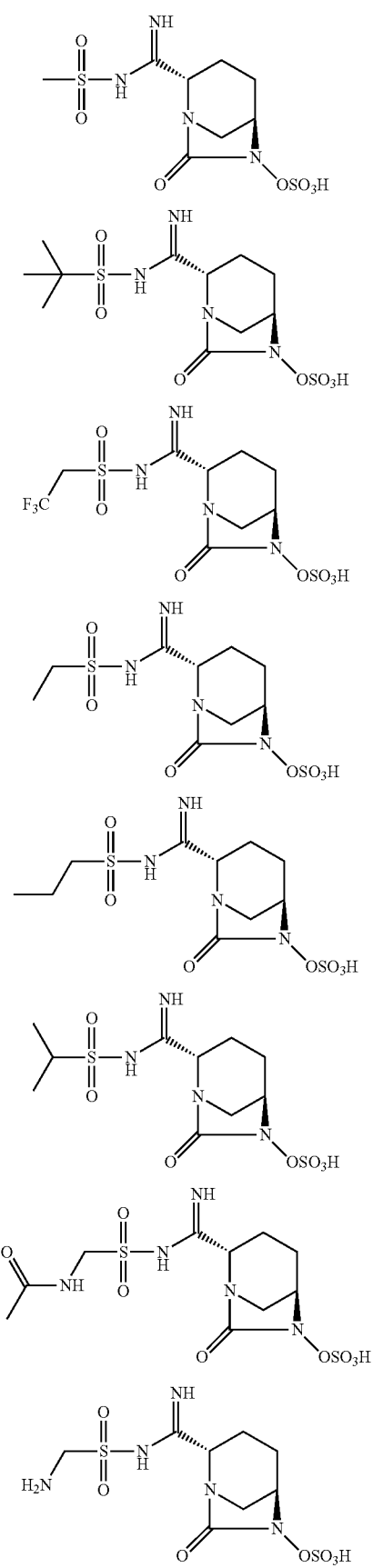

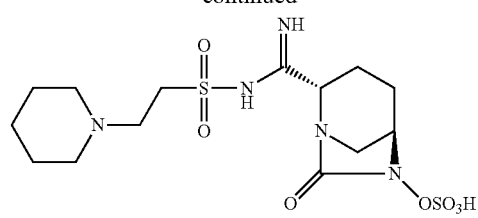
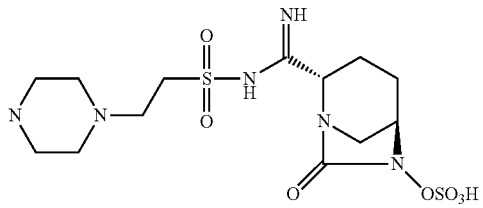
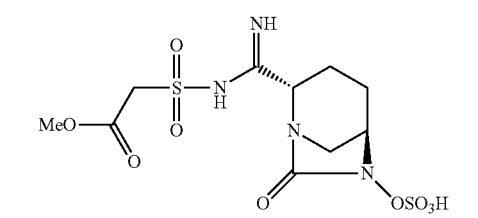
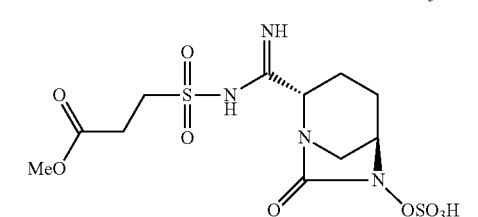
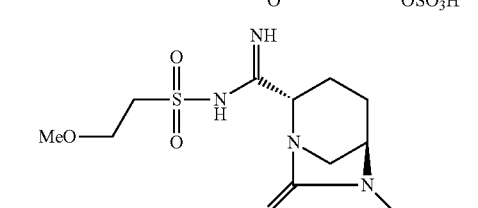
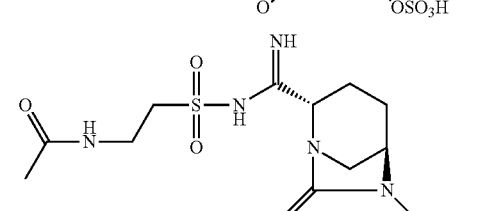
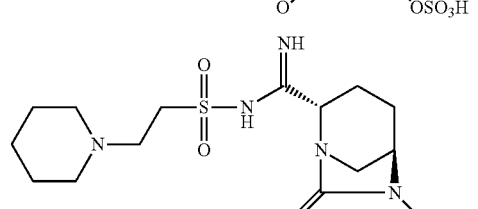
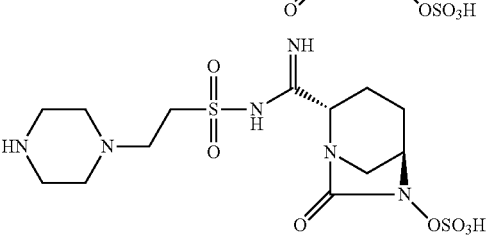
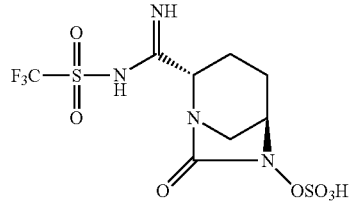
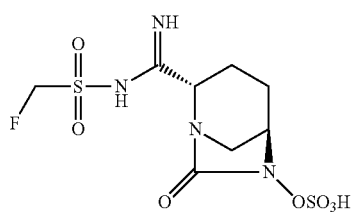
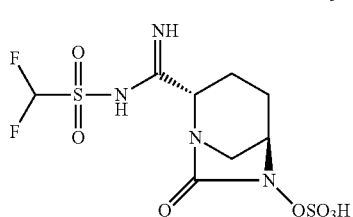
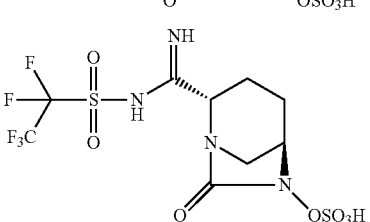
(2) $C_{3-6}$ cycloalkyl or heterocycles which is optionally substituted. Non-limiting examples of such compounds are:
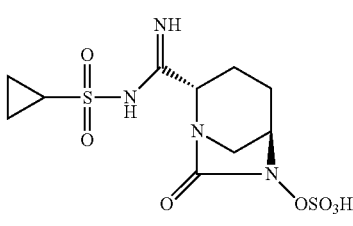
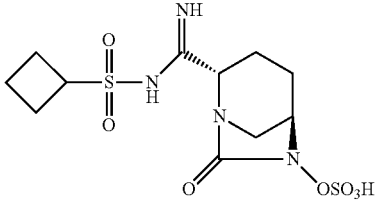
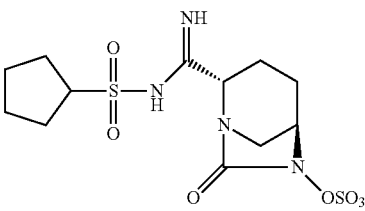

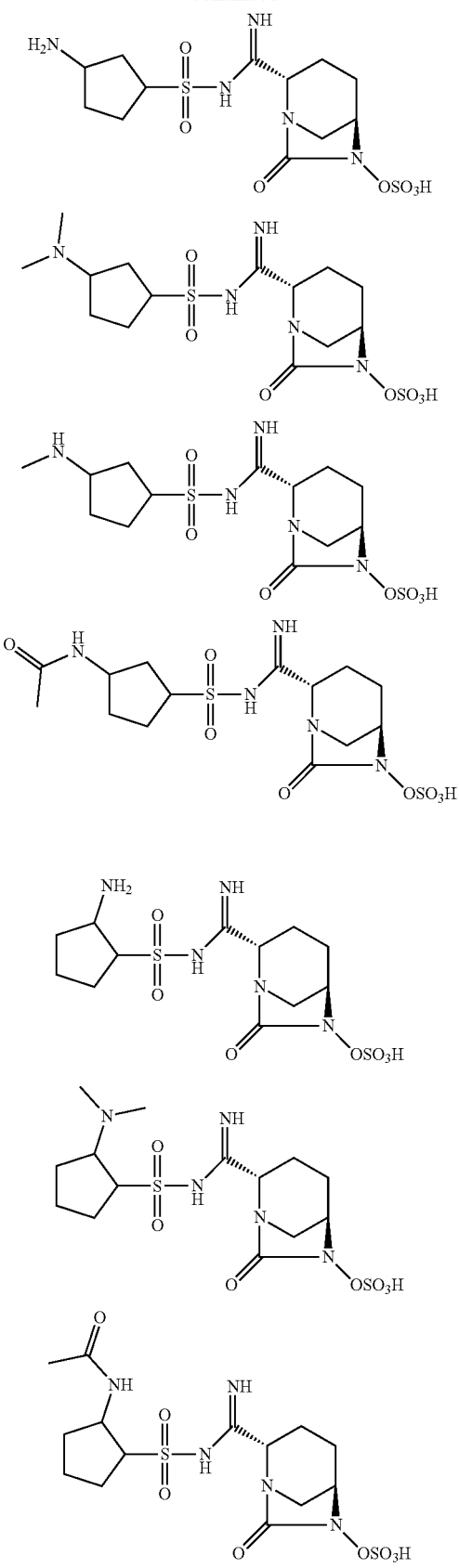
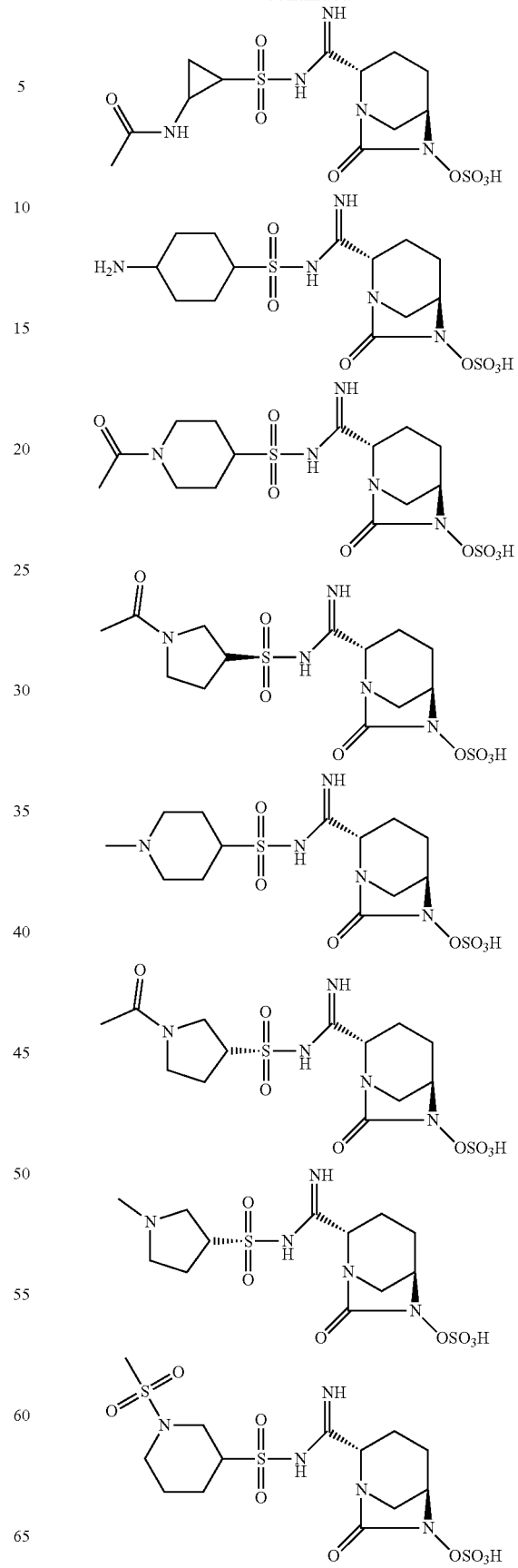

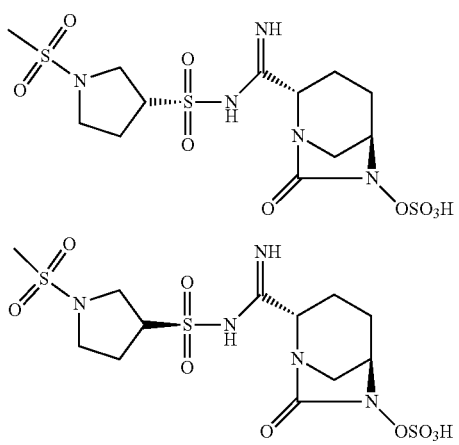
(3) $C_{5-6}$ membered aryl or heteroaryl which is optionally substituted. Non-limiting examples of such compounds are:
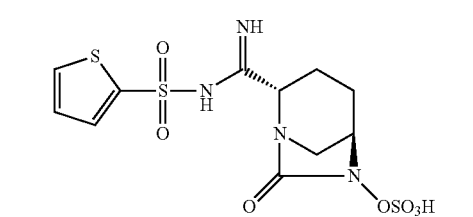
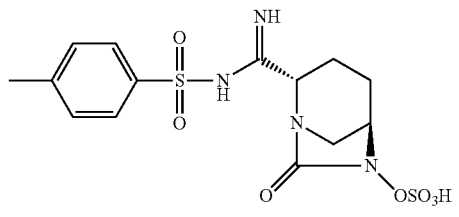
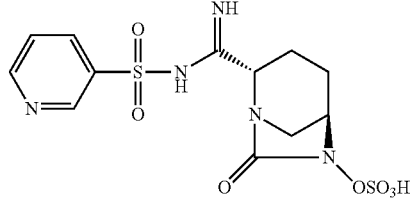
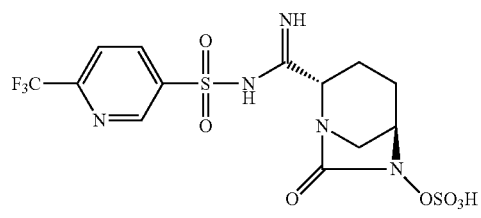
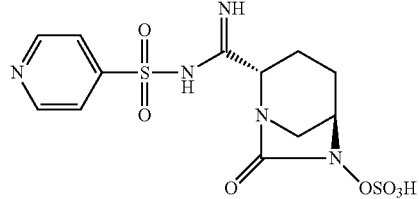
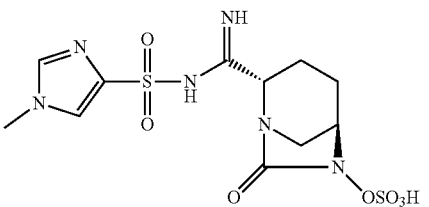
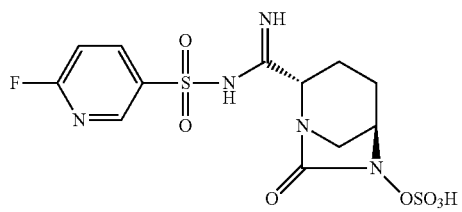
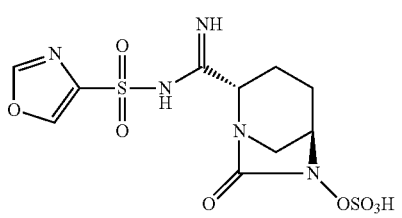
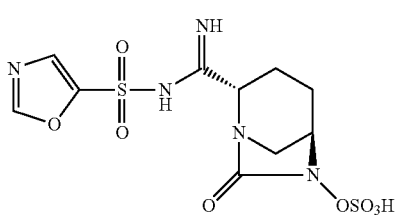
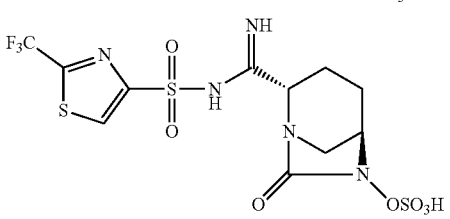
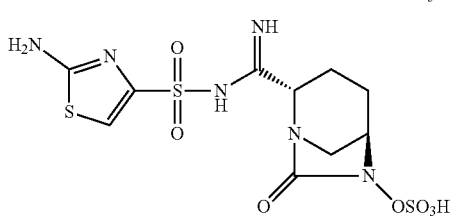
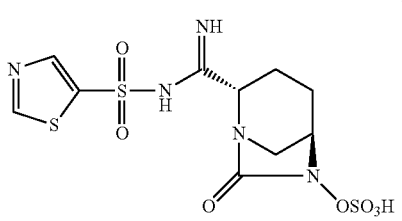
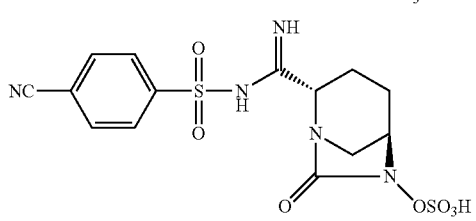

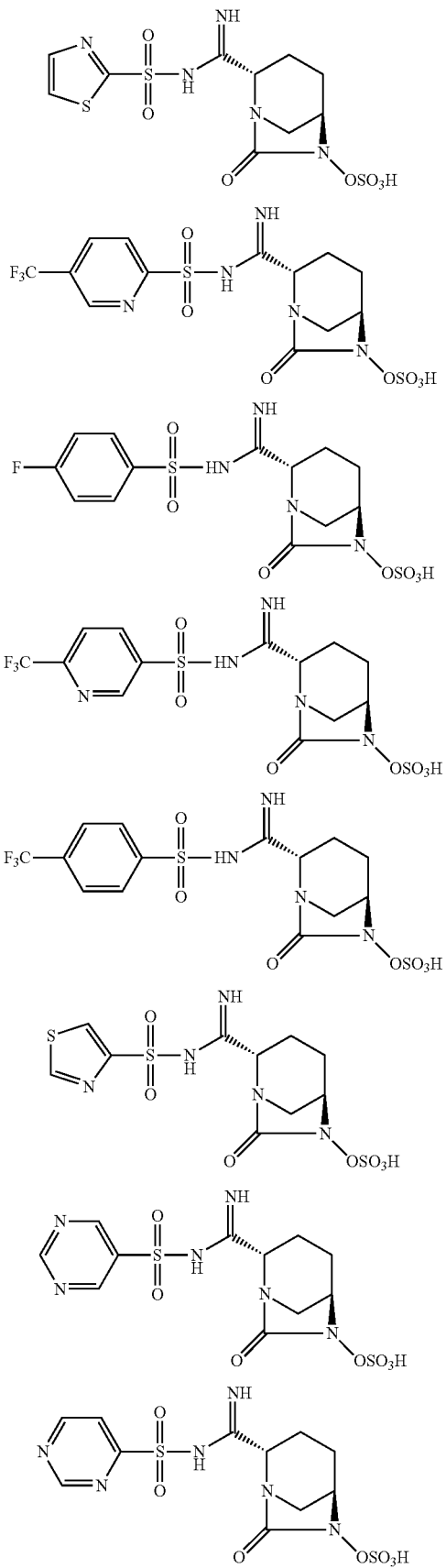
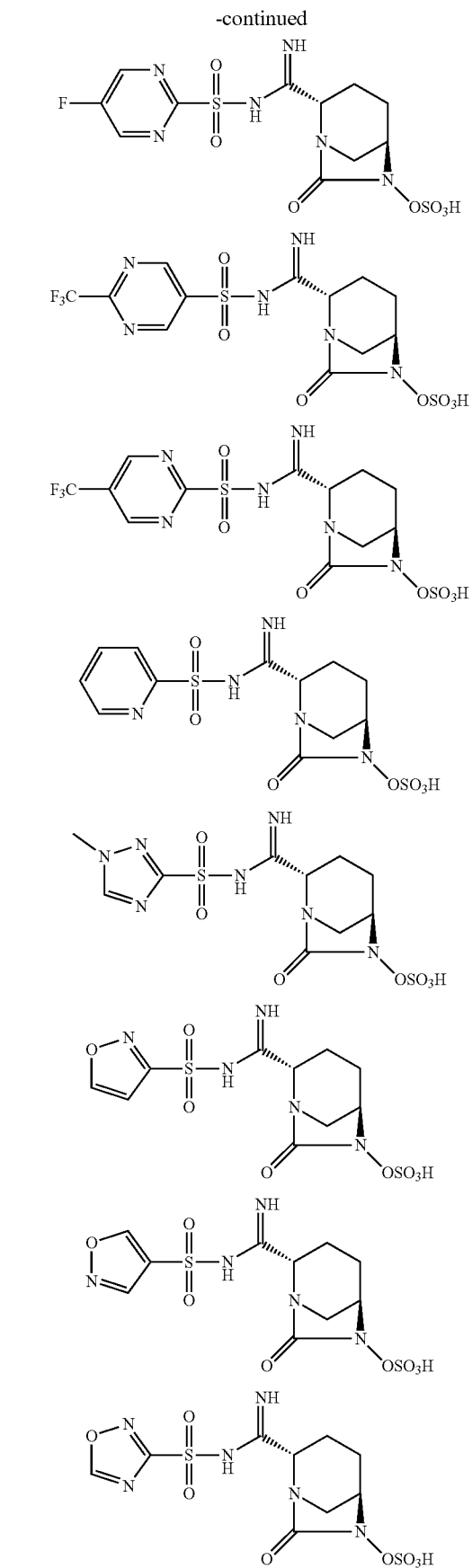

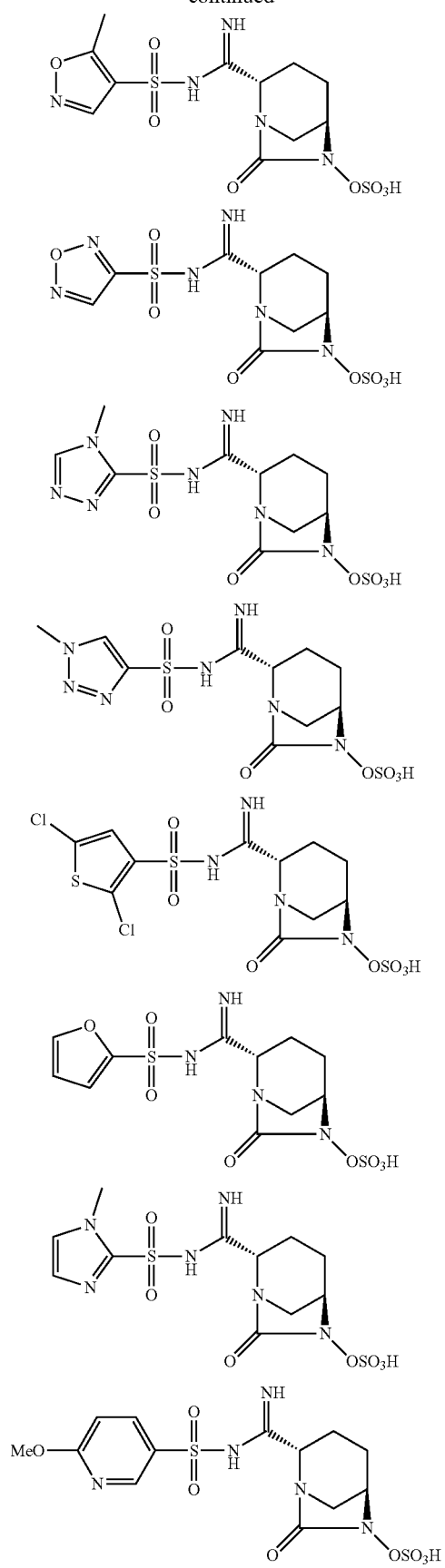
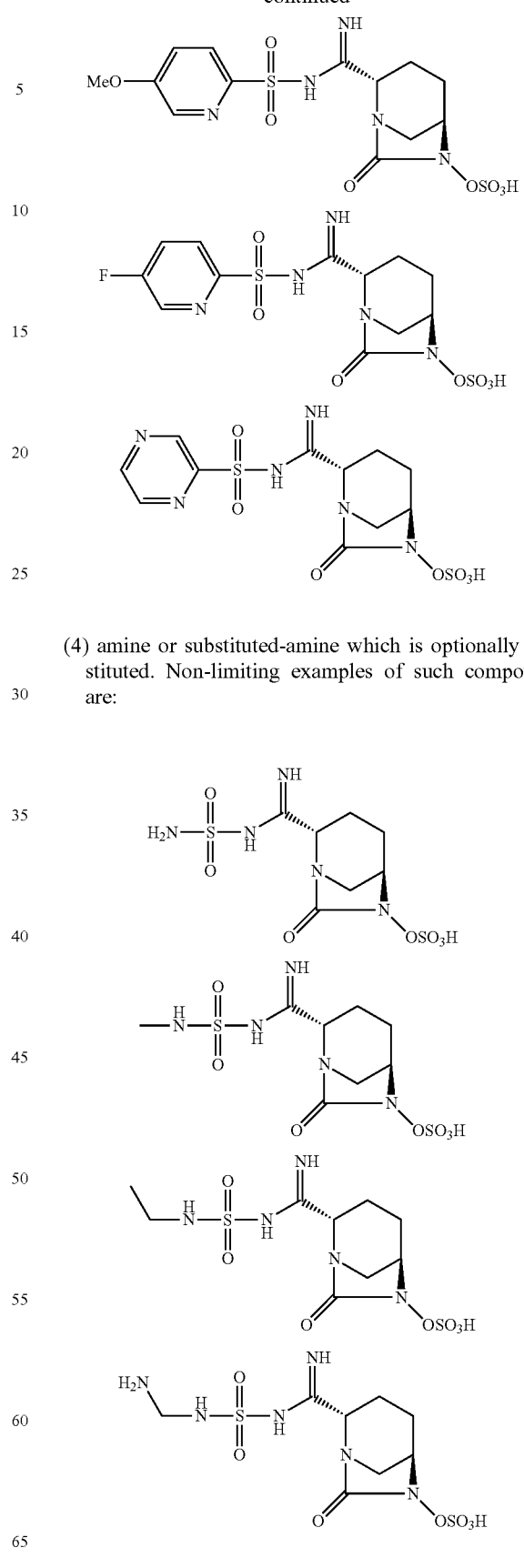
(4) amine or substituted-amine which is optionally substituted. Non-limiting examples of such compounds are:

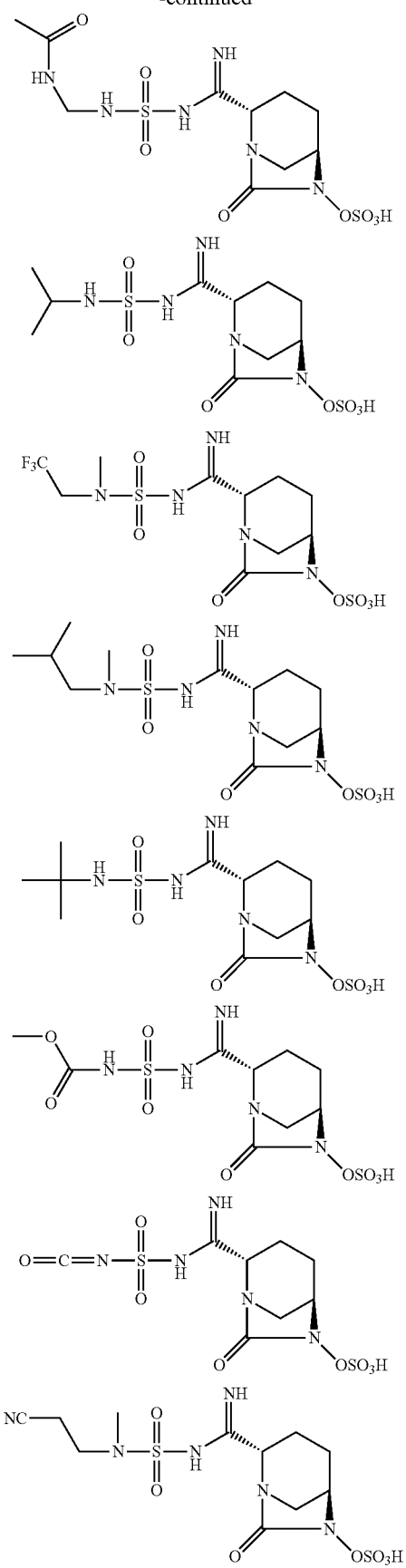
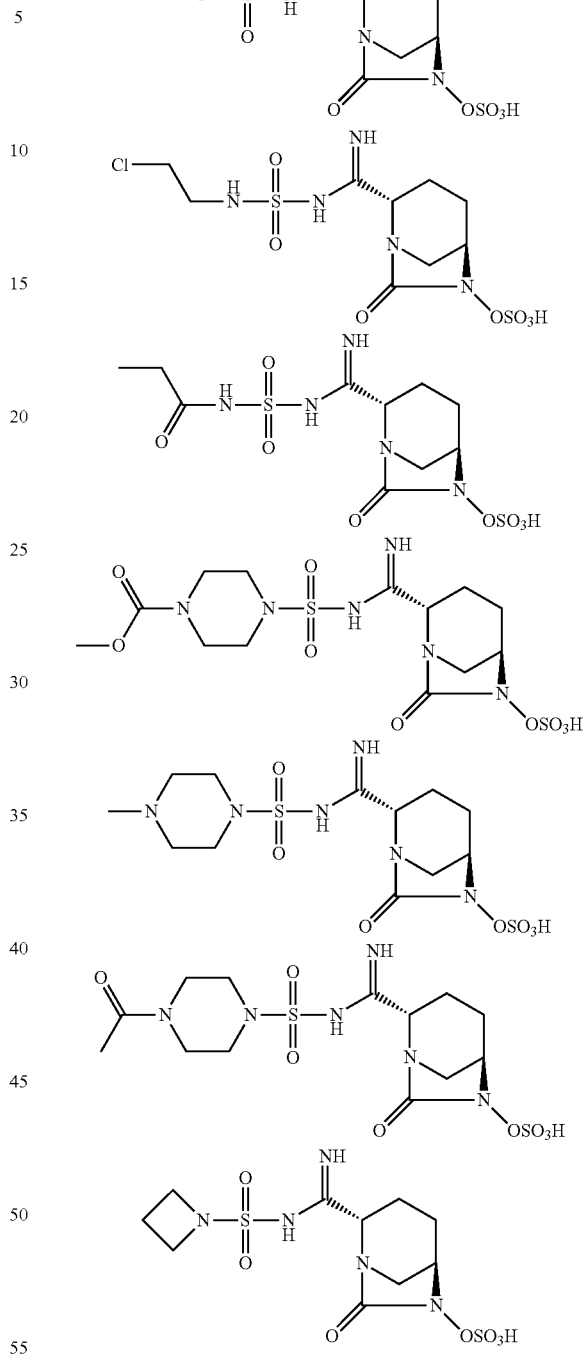

Examples of the groups for forming a pharmaceutically acceptable salt represented by M in the formula (I) include: inorganic base salts, ammonium salts, organic base salts, basic amino acid salts, inorganic acid addition salts, and organic acid addition salts. Inorganic bases that can form the inorganic base salts include alkali metals such as sodium, potassium, and lithium and alkaline earth metals such as calcium and magnesium. Organic bases that can form the organic base salts include n-propylamine, n-butylamine, cyclohexylamine, benzylamine, octylamine, ethanolamine, diethanolamine, diethylamine, triethylamine, dicyclohexylamine, procaine, choline, N-methylglucamine, morpholine, pyrrolidine, piperidine, N-ethylpiperidine and N-methylmorpholine.

Basic amino acids that can form the basic amino acid salts include lysine, arginine, ornithine and histidine. As will be appreciated by one skilled in the art, the compounds of formula (I) containing a basic nitrogen atom are capable of forming acid addition salts. Such salts with pharmaceutically acceptable acids are included in the invention. Examples of such acids are hydrochloric, hydrobromic, phosphoric, sulphuric, citric, oxalic, maleic, fumaric, glycolic, mandelic, tartaric, aspartic, succinic, malic, formic, acetic, p-toluenesulfonic, trifluoroacetic, methanesulfonic, ethanesulfonic, trifluoromethanesulfonic, benzenesulfonic and the like.

Moreover, some compounds of formula (I) when they contain a basic group such as NH, $NH_2$ or pyridine and the like may form an inner, zwitterionic salt with $OSO_3H$, such inner salts are also included in this invention.

Another aspect of the present invention is to include all possible isomers of formula (I). As used herein, the term 'isomers' refers to different compounds that have the same molecular formula but differ in arrangement and configuration of the atoms, such as geometrical isomers and optical isomers. For a given compound of the present invention, it is understood that a substituent may be attached at a chiral center of a carbon atom. Therefore the invention includes enantiomers, diastereomers or racemates of the compound. By definition, 'enantiomers' are a pair of stereoisomers that are non-superimposable mirror images of each other, and 1:1 mixture of a pair of enantiomers is a racemic mixture. By definition, 'diastereoisomers' are stereoisomers that have at least two asymmetric carbon atoms but which are not mirror-images of each other. When a compound of formula (I) is a pure enantiomer the stereochemistry at each chiral carbon may be specified by either R or S.

A variety of protecting groups conventionally used in the β-lactam field to protect a reactive functional group present in the compound of formula (I) can be used. 'Protecting group' refers to a group of atoms that when attached to a reactive functional group in a molecule masks, reduces or prevents reactivity of the functional group. Examples of protecting groups can be found in "Protective Groups in Organic Synthesis", (Theodora W. Greene and Peter G. M. Wuts, John Wiley & Sons. Inc., $3^{rd}$, 1999). Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 9-fluorenylmethyloxycarbonyl (FMOC), nitro-veratryoxycarbonyl (NVOC), and the like. Examples of hydroxy protecting groups include, but are not limited to, those where the hydroxyl group is either acylated or alkylated such as benzyl, and trityl ethers as well as alkyl ethers, tetrahydropyranyl ethers, trialkylsilyl ethers, and allyl ethers.

The term 'optionally substituted' refers to unsubstituted or substituted with one or two of the following substituents each of which is independently selected from:

Lower alkyl including from one to six carbon atoms in any arrangement, e.g., methyl, ethyl, i-propyl or t-butyl, Amino, Substituted amino such as $—NHCH_3$, $—N(CH_3)_2$, $—NHCH_2CH_3$, $—NHPr^i$, $—NHBu^t$, Alkoxy such as $—OCH_3$, $—OC_2H_5$, $—OPr^i$ (i.e., isopropyloxy), $—OBu^t$ (i.e., isobtutyloxy), Hydroxyalkyl such as $—CH_2OH$, $—CH_2CH_2OH$, Halogen such as F, Cl, Br, Hydroxy, Carboxy, Alkoxycarbonyl such as $—COOCH_3$, $—COOC_2H_5$, $—COOPr^i$, and $—COOBu^t$, Haloalkyl such as $—CH_2Cl$, $—CH_2F$, Trifluoromethyl, Trifluoromethyloxy, Alkylamine such as $—CH_2NH_2$, $—CH_2CH_2NH_2$, Substituted alkylamine such as $—CH_2CH_2NHCH_3$, $—CH_2CH_2N(CH_3)_2$, $—CH_2NHCH_3$, $—CH_2N(CH_3)_2$, Carboxamide, Thiocarboxamide, Sulfonic acid, Sulfate, Acylamino, Sulfonylamino, Sulfonamide, Substituted sulfonamide such as $—SO_2NHCH_3$, $—SO_2NHPr^i$, $—SO_2NHBu^t$, $—SO_2NHCH_2CH_3$, Urea ($—NHCONH_2$) which may be optionally substituted, Thiourea ($—NHCSNH_2$), optionally substituted, Sulfonylurea ($—NHSO_2NH_2$), optionally substituted, Oxo (=O) when oxygen is bonded through double bond to a carbon atom, Oxyimino (=N—O-A) where the nitrogen is bonded through double bond to a carbon atom which is attached to the rest of the molecule and A can be hydrogen, or optionally substituted straight or branched lower alkyl, cycloalkyl, aryl, heteroaryl and heterocyclyl, Hydroxamic acid ($—CONHOH$), Acyl ($—COCH_3$), Trifluoromethyl carbonyl ($—COCF_3$), Cyano ($—CN$), Amidino $—C(=NH)NH_2$ which may be optionally substituted, Guanidino $—NHC(=NH)NH_2$ which may be optionally substituted, Aryloxy, Heterocyclyl, Heteroaryl, Heterocyclyloxy, Heteroaryloxy, Heterocyclylalkyloxy, Trialkylammonium, The substituent mentioned above could be substituted at the carbon atom or at the free N-atom of the molecule as appropriate.

Among the compounds of formula (I), a particular subject of the invention is those in which M is hydrogen or a pharmaceutically acceptable salt forming cation.

A group of preferred examples of formula (I) are from the following Table 1

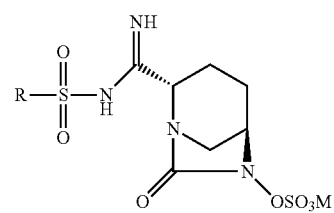

[I]

* =point of attachment with S

TABLE 1
| Compound No. | M | R |
|---|---|---|
| 1 | Na |  |
| 2 | H |  |
| 3 | Na |  |
| 4 | Na |  |
| 5 | H |  |
| 6 | H |  |
| 7 | H |  |
| 8 | H |  |
| 9 | H |  |
| 10 | H |  |
| 11 | H |  |
| 12 | H |  |
| 13 | H |  |
| 14 | H |  |
| 15 | H |  |
| 16 | H |  |
| 17 | H |  |
| 18 | H | 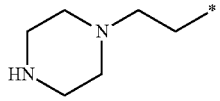 |
| 19 | Na | 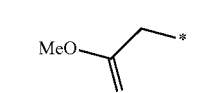 |
| 20 | Na | 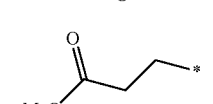 |
| 21 | Na | 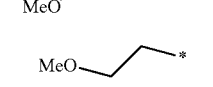 |
| 22 | H | 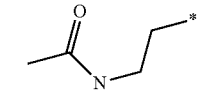 |
| 23 | H |  |
| 24 | H |  |
| 25 | Na | 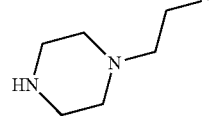 |
| 26 | H |  |
| 27 | H | 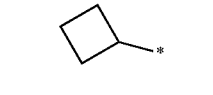 |
| 28 | H | 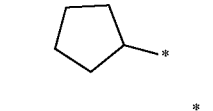 |
| 29 | H | 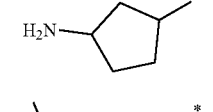 |
| 30 | H | 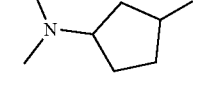 |
| 31 | H | 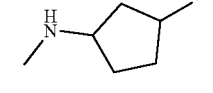 |

TABLE 1-continued

List of compounds

| Compound No. | M | R |
|---|---|---|
| 32 | H | 2-aminocyclopentyl |
| 33 | H | 2-(dimethylamino)cyclopentyl |
| 34 | H | 2-acetamidocyclopentyl |
| 35 | H | 2-acetamidocyclopropyl |
| 36 | H | 4-aminocyclohexyl |
| 37 | H | thiophen-2-yl |
| 38 | Na | 4-methylphenyl |
| 39 | H | pyridin-3-yl |
| 40 | H | 6-(trifluoromethyl)pyridin-3-yl |
| 41 | H | pyridin-4-yl |
| 42 | Na | 1-methyl-1H-imidazol-4-yl |
| 43 | H | 6-fluoropyridin-3-yl |
| 44 | H | oxazol-4-yl |
| 45 | H | oxazol-5-yl |
| 46 | H | 2-(trifluoromethyl)thiazol-4-yl |
| 47 | H | 2-aminothiazol-4-yl |
| 48 | H | thiazol-5-yl |
| 49 | H | 4-cyanophenyl |
| 50 | H | thiazol-2-yl |
| 51 | H | 5-(trifluoromethyl)pyridin-2-yl |
| 52 | H | 4-fluorophenyl |
| 53 | H | 1,1,2,2,2-pentafluoroethyl (perfluoroethyl) |
| 54 | H | 4-(trifluoromethyl)phenyl |
| 55 | H | thiazol-4-yl |

TABLE 1-continued
List of compounds
| Compound No. | M | R |
|---|---|---|
| 56 | H | 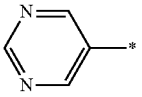 [SMILES: *c1cncnc1] |
| 57 | H | 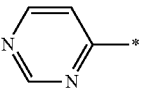 |
| 58 | H | 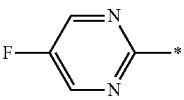 [SMILES: *c1ncc(F)cn1] |
| 59 | H | 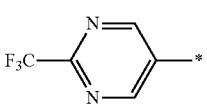 |
| 60 | H | 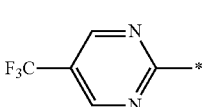 |
| 61 | H | 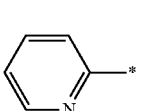 |
| 62 | H | 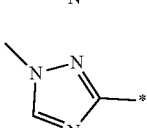 |
| 63 | H | 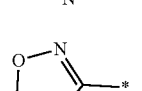 |
| 64 | H | 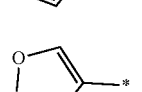 |
| 65 | H | 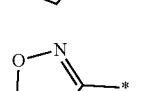 |
| 66 | H |  |
| 67 | H | 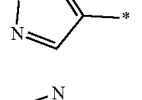 |
| 68 | H | 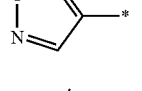 |
TABLE 1-continued
List of compounds
| Compound No. | M | R |
|---|---|---|
| 69 | H | 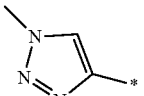 |
| 70 | H |  |
| 71 | H |  |
| 72 | H |  |
| 73 | H | 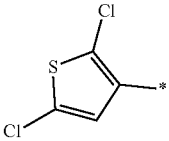 [SMILES: *c1cc(Cl)sc1Cl] |
| 74 | H | 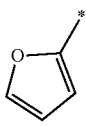 |
| 75 | H |  |
| 76 | H |  |
| 77 | H | 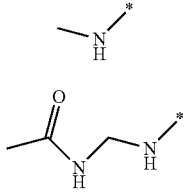 |
| 78 | H | 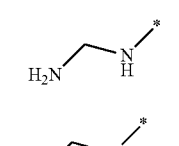 |
| 79 | H | 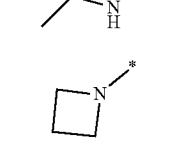 |
| 80 | H |  |
| 81 | H | 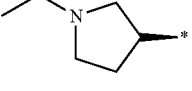 |
| 82 | H | 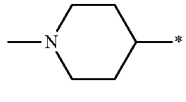 [SMILES: *C1CCN(C)CC1] |
| 83 | H | 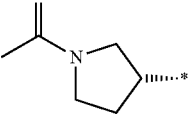 |

TABLE 1-continued

List of compounds

| Compound No. | M | R |
|---|---|---|
| 84 | H | (S)-1-methylpyrrolidin-3-yl |
| 85 | H | 1-acetylpiperidin-4-yl |
| 86 | H | (S)-1-(methylsulfonyl)pyrrolidin-3-yl |
| 87 | H | (R)-1-(methylsulfonyl)pyrrolidin-3-yl |
| 88 | H | 1-(methylsulfonyl)piperidin-4-yl |
| 89 | H | isopropylamino |
| 90 | H | 2,2,2-trifluoroethylamino |
| 91 | H | isobutylamino |
| 92 | H | tert-butylamino |
| 93 | H | methoxycarbonylamino |
| 94 | H | formamido |
| 95 | H | (2-cyanoethyl)amino |
| 96 | H | diethylamino |
| 97 | H | (2-chloroethyl)amino |
| 98 | H | propanamido |
| 99 | H | 1-(methoxycarbonyl)piperidin-4-ylamino |
| 100 | H | 1-methylpiperidin-4-ylamino |
| 101 | H | 1-acetylpiperidin-4-ylamino |
| 102 | H | 1-(methylsulfonyl)piperidin-3-ylamino |
| 103 | H | 1-methyl-1H-imidazol-2-yl |
| 104 | H | 6-methoxypyridin-3-yl |
| 105 | H | 5-methoxypyridin-2-yl |
| 106 | H | 5-fluoropyridin-2-yl |
| 107 | H | pyrazin-2-yl |

It is also an object of this invention to provide a combination of a compound of general formula (I) having antibacterial activity with another existing antibacterial agent, thus causing synergistic effect and the use of the same as drugs for the treatment of bacterial infections.

It is another object of the invention to provide methods for preparing the compounds of the invention of formula (I).

It is a further object of the invention to provide pharmaceutical compositions comprising a compound of formula (I) of this invention as an active ingredient in combination with an antibiotic (e.g., a β-lactam antibiotic or some other non β-lactam antibiotic) and a suitable amount of pharmaceutically acceptable carrier or diluent, so as to provide a form for proper administration to a patient. These compositions can be administered by parenteral, in particular intramascular route, oral, sublingual, rectal, aerosol or by local route in a topical application on the skin and the mucous membranes. Suitable pharmaceutical vehicles include excipients such as starch, glucose, lactose, sucrose, gelatin, gum arabic, malt, rice, flour, chalk, silica gel, sodium stearate, glycerol monostearate, talc, sodium chloride, dried skim milk, glycerol, propylene, glycol, water, ethanol, and the like. Other examples of suitable pharmaceutical vehicles have been described in the art (Remington's Science and Practice of Pharmacy, 21$^{st}$ Edition, 2006). Compositions of the present disclosure, if desired, can also contain minor amounts of wetting, dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen. The present pharmaceutical compositions can take the form of injectable preparations, suspensions, emulsions, sugar-coated tablets, pellets, gelatin-capsules, capsules containing liquids, powders, granules, sustained-release formulations, suppositories, aerosols, sprays, ointments, creams or any other form suitable for use.

In another aspect, the present invention also provides for the use, in the manufacture of a medicament, of a compound within formula (I) above as an active ingredient in an antibacterial composition in admixture with a carrier.

In another aspect, the present invention also provides for the use, in the manufacture of a medicament, of a compound within formula (I) above as an active ingredient.

In another aspect, the present invention also provides for the use, in the manufacture of a medicament, of a compound within formula (I) above as an active ingredient, along with one or more β-lactam antibiotics (e.g., a β-lactam antibiotic or some other non β-lactam antibiotic), in an antibacterial composition in admixture with a carrier.

In another aspect, the present invention also provides for the use, in the manufacture of a medicament, of a compound within formula (I) above as an active ingredient, along with one or more β-lactam antibiotics (e.g., a β-lactam antibiotic or some other non β-lactam antibiotic).

For the parenteral administration which includes intramuscular, intraperitonial, subcutaneous and intravenous use, sterile solutions of the active ingredient are usually prepared and the pH of the solutions are suitably adjusted and buffered. For intravenous use, the total concentration of solutes should be controlled to render the preparation isotonic. Suitable solvents include saline solution (e.g., 0.9% NaCl solution) and apyrogenic sterile water. Pharmaceutical compositions for oral delivery can be, for example, in the form of tablets, lozenges, aqueous or oily suspensions, granules, powders, emulsions, capsules, syrups, or elixirs. Orally administered compositions can contain one or more optional agents, for example, sweetening agents such as fructose, aspartame, or saccharin, flavoring agents such as peppermint, oil of wintergreen, cherry, coloring agents, and preserving agents to provide a pharmaceutically palatable preparation. Moreover, when in tablet form, the compositions can be coated to delay disintegration and absorption in the gastrointestinal tract, thereby providing a sustained action over an extended period of time. Oral compositions can include standard vehicles such as mannitol, lactose, starch, magnesium stearate, sodium saccharin, cellulose, magnesium carbonate, and the like. For oral liquid preparations, for example, suspensions, elixirs, and solutions, suitable carriers, excipients, or diluents include water, saline, alkyleneglycols (e.g. propylene glycol), polyalkylene glycols (e.g., polyethylene glycol), oils, alcohols, slightly acidic buffers ranging from about pH 4 to about pH 6 (e.g., acetate, citrate, ascorbate ranging from about 5 mM to about 50 mM), and the like. Additionally, flavoring agents, preservatives, coloring agents, bile salts, acylcarnitines, and the like can be added.

For topical formulations of compounds of the present invention, creams, gels, ointments or viscous lotions can be used as appropriate delivery forms. Topical delivery systems also include transdermal patches containing at least one compound of formula (I) to be administered.

Delivery through the skin can be achieved by diffusion or by more active energy sources such as iontophoresis or electrotransport. Formulations of a compound of the present invention, for topical use, such as in creams, ointments, and gels, can include an oleaginous or water soluble ointment base, for example, topical compositions can include vegetable oils, animal fats, and in certain embodiments, semi-solid hydrocarbons obtained from petroleum. Topical compositions can further include white ointment, yellow ointment, cetyl esters wax, oleic acid, olive oil, paraffin, petrolatum, white petrolatum, spermaceti, starch glycerite, white wax, yellow wax, lanolin, and glyceryl monostearate. Various water-soluble ointment bases can also be used, including glycol ethers and derivatives, polyethylene glycols, polyoxyl 40 stearate, and polysorbates.

In a pharmaceutical composition containing a compound of this invention, the weight ratio of active ingredient to carrier will normally be in the range of 1:30 to 30:1, for example, 1:25 to 25:1, 1:20 to 20:1, 1:15 to 15:1, 1:10 to 10:1, 1:5 to 5:1, 1:4 to 4:1, 1:3 to 3:1, 1:2 to 2:1, or 1:1. The administered daily dose varies according to the illness treated, and the administration route. However in most instances, an effective dose (e.g., in some instances, β-lactamase inhibiting dose) of a compound of formula (I) or a pharmaceutically acceptable salt thereof will be a daily dose in the range from about 1 to about 500 mg per kilogram of body weight orally, and from about 1 to about 500 mg per kilogram of body weight parenterally. The weight ratio of the compound of present invention to the antibiotic (if it is being administered with an antibiotic) will normally be in the range from 1:30 to 30:1, for example, 1:25 to 25:1, 1:15 to 15:1, 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1, or 1:1.

In some aspects of the present invention, an additional object is to provide an improved method for the treatment of bacterial infections caused by β-lactamase producing bacteria in a patient in need of such treatment comprising administering to the patient a therapeutically effective amount of at least one compound chosen from formula (I) or a pharmaceutically acceptable salt thereof in combination with a known β-lactam antibiotic. In such an aspect of the present invention, the compounds increase the antibacterial effectiveness of lactamase susceptible β-lactam antibiotics, that is, they increase the effectiveness of the antibiotic against infections caused by β-lactamase producing microorganisms in mammalian subjects, particularly in human. In these aspects of the present invention, this makes the compounds of formula (I) and pharmaceutically acceptable salts thereof, valuable for co-administration with β-lactam antibiotics. In the treatment of a bacterial infection in such an aspect of the present invention, said compounds of formula (I) or a pharmaceutically salt thereof can be mixed with the β-lactam antibiotic, and the two agents thereby administered simultaneously. When co-administered with a β-lactam antibiotic in such an aspect of the present invention, the combination of the compound of the invention and the antibiotic can provide a synergystic effect. The term 'synergystic effect' refers to the effect produced when two or more agents are co-administered is greater than the effect produced when the agents are administered individually. Alternatively, the compound of formula (I) or a salt thereof can be administered as a separate agent during a course of treatment with the antibiotic.

'Therapeutically effective amount' refers to the amount of a compound that, when administered to a subject for treating a disease, or at least one of the clinical symptoms of a disease, is sufficient to affect such treatment of the disease, disorder, or symptom. The therapeutically effective amount can vary depending, for example, on the compound, the disease, disorder, and/or symptoms of the disease, severity of the disease, disorder, and/or symptoms of the disease, the age, weight, and/or health of the patient to be treated, and the judgement of the prescribing physician.

The term 'β-lactam antibiotic' refers to a compound with antibiotic property that contains a β-lactam functionality. Examples of β-lactam antibiotics which can be used in combination with the compounds of the present invention represented by formula (I) are commonly marketed penicillins, cephalosporins, penems, carbapenems and monobactams.

Examples of β-lactam antibiotics which can be used in combination with the compounds of the present invention represented by formula (I) are commonly used penicillins, such as amoxicillin, ampicillin, azlocillin, mezlocillin, apalcillin, hetacillin, bacampicillin, carbenicillin, sulbenicillin, ticarcillin, piperacillin, methicillin, ciclacillin, talampicillin, oxacillin, cloxacillin, dicloxacillin and commonly used cephalosporins such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, cefepime, ceftazidime, cefpiramide, ceftriaxone, cefbuperazone, cefprozil, cefixime, ceftobiprole, ceftaroline, cefalonium, cefminox, ceforanide, cefuzonam, cefoxitin, cefotetan, loracarbef, cefdinir, cefditoren, cefetamet, cefcapene, cefdaloxime, ceftibuten, cefroxadine and latamoxef (moxalactam). From the carbapenem class of β-lactam antibiotics such as imipenem, meropenem, panipenem, biapenem, doripenem, ertapenem and the like could be used. From monobactam class of β-lactam antibiotics such as aztreonam, carumonam, tigemonam, and the like could be used as the combination partner of antibiotic.

Examples of antibiotics (which are not β-lactam antibiotics) which can be used in combination with the compounds of the present invention (i.e., compounds of formula (I) above, salts, thereof, solvates of such compounds and salts, and deuterated compounds of any such compounds) include aminoglycosides, quinolones, tetracyclines, glycylcyclines, glycopeptides, lipopeptides, macrolides, ketolidides, lincosamides, streptogramin, oxazolidinones, polymyxins, and other compounds known to have antibacterial properties.

'Pharmaceutically acceptable solvate' refers to a molecular complex of a compound with one or more solvent molecules in a stoichiometric or non-stoichiometric amount. Such solvent molecules are those commonly used in the pharmaceutical art, which are known to be innocuous to recipient, e.g., water, ethanol, and the like. A molecular complex of a compound or moiety of a compound and a solvent can be stabilized by non-covalent intra-molecular forces such as, for example, electrostatic forces, Van der Waals forces or hydrogen bonds. The term hydrate refers to a complex where the one or more solvent molecules are water.

Among the compounds of formula (I), a particular subject of the invention is the compounds with the following names. The following examples illustrate the invention, and are not intended to be limiting of its scope. To the contrary, the claims are intended to cover alternatives, modifications, and equivalents.

The non-limiting examples of the compounds of the present invention are:

(2S,5R)-2-(N-(methylsulfonyl)carbamimidoyl)-7-oxo-1,6-diazabicyclo[3.2.1]octan-6-yl hydrogen sulfate.

(2S,5R)-2-(N-(tert-butylsulfonyl)carbamimidoyl)-7-oxo-1,6-diazabicyclo[3.2.1]octan-6-yl hydrogen sulfate.

(2S,5R)-7-oxo-2-(N-((2,2,2-trifluoroethyl)sulfonyl)carbamimidoyl)-1,6-diazabicyclo[3.2.1]octan-6-yl hydrogen sulfate.

(2S,5R)-2-(N-(ethylsulfonyl)carbamimidoyl)-7-oxo-1,6-diazabicyclo[3.2.1]octan-6-yl hydrogen sulfate.

(2S,5R)-7-oxo-2-(N-(propylsulfonyl)carbamimidoyl)-1,6-diazabicyclo[3.2.1]octan-6-yl hydrogen sulfate.

(2S,5R)-2-(N-(isopropylsulfonyl)carbamimidoyl)-7-oxo-1,6-diazabicyclo[3.2.1]octan-6-yl hydrogen sulfate.

(2S,5R)-2-(N-((acetamidomethyl)sulfonyl)carbamimidoyl)-7-oxo-1,6-diazabicyclo[3.2.1]octan-6-yl hydrogen sulfate.

(2S,5R)-2-(N-((aminomethyl)sulfonyl)carbamimidoyl)-7-oxo-1,6-diazabicyclo[3.2.1]octan-6-yl hydrogen sulfate.

(2S,5R)-2-(N-((hydroxymethyl)sulfonyl)carbamimidoyl)-7-oxo-1,6-diazabicyclo[3.2.1]octan-6-yl hydrogen sulfate.

(2S,5R)-7-oxo-2-(N-((ureidomethyl)sulfonyl)carbamimidoyl)-1,6-diazabicyclo[3.2.1]octan-6-yl hydrogen sulfate.

2-(N-(imino((2S,5R)-7-oxo-6-(sulfooxy)-1,6-diazabicyclo[3.2.1]octan-2-yl)methyl)sulfamoyl)acetic acid.

(2S,5R)-2-(N-((methoxymethyl)sulfonyl)carbamimidoyl)-7-oxo-1,6-diazabicyclo[3.2.1]octan-6-yl hydrogen sulfate.

(2S,5R)-2-(N-((1-aminoethyl)sulfonyl)carbamimidoyl)-7-oxo-1,6-diazabicyclo[3.2.1]octan-6-yl hydrogen sulfate.

(2S,5R)-2-(N-((2-amino-2-oxoethyl)sulfonyl)carbamimidoyl)-7-oxo-1,6-diazabicyclo[3.2.1]octan-6-yl hydrogen sulfate.

(2S,5R)-2-(N-((2-morpholinoethyl)sulfonyl)carbamimidoyl)-7-oxo-1,6-diazabicyclo[3.2.1]octan-6-yl hydrogen sulfate.

(2S,5R)-2-(N-((2-acetamidoethyl)sulfonyl)carbamimidoyl)-7-oxo-1,6-diazabicyclo[3.2.1]octan-6-yl hydrogen sulfate.

(2S,5R)-7-oxo-2-(N-((2-(piperidin-1-yl)ethyl)sulfonyl)carbamimidoyl)-1,6-diazabicyclo[3.2.1]octan-6-yl hydrogen sulfate.

(2S,5R)-2-(N-((2-(412-piperazin-1-yl)ethyl)sulfonyl)carbamimidoyl)-7-oxo-1,6-diazabicyclo[3.2.1]octan-6-yl hydrogen sulfate.

(2S,5R)-2-(N-((2-ethoxy-2-oxoethyl)sulfonyl)carbamimidoyl)-7-oxo-1,6-diazabicyclo[3.2.1]octan-6-yl hydrogen sulfate.

(2S,5R)-2-(N-((3-methoxy-3-oxopropyl)sulfonyl)carbamimidoyl)-7-oxo-1,6-diazabicyclo[3.2.1]octan-6-yl hydrogen sulfate.

(2S,5R)-2-(N-((2-methoxyethyl)sulfonyl)carbamimidoyl)-7-oxo-1,6-diazabicyclo[3.2.1]octan-6-yl hydrogen sulfate.

(2S,5R)-2-(N-((2-acetamidoethyl)sulfonyl)carbamimidoyl)-7-oxo-1,6-diazabicyclo[3.2.1]octan-6-yl hydrogen sulfate.

(2S,5R)-7-oxo-2-(N-((2-(piperidin-1-yl)ethyl)sulfonyl)carbamimidoyl)-1,6-diazabicyclo[3.2.1]octan-6-yl hydrogen sulfate.

(2S,5R)-7-oxo-2-(N-((2-(piperazin-1-yl)ethyl)sulfonyl)carbamimidoyl)-1,6-diazabicyclo[3.2.1]octan-6-yl hydrogen sulfate.

(2S,5R)-2-(N-(cyclopropylsulfonyl)carbamimidoyl)-7-oxo-1,6-diazabicyclo[3.2.1]octan-6-yl hydrogen sulfate.

(2S,5R)-2-(N-(cyclobutylsulfonyl)carbamimidoyl)-7-oxo-1,6-diazabicyclo[3.2.1]octan-6-yl hydrogen sulfate.

(2S,5R)-2-(N-(cyclopentylsulfonyl)carbamimidoyl)-7-oxo-1,6-diazabicyclo[3.2.1]octan-6-yl hydrogen sulfate.

(2S,5R)-2-(N-((3-aminocyclopentyl)sulfonyl)carbamimidoyl)-7-oxo-1,6-diazabicyclo[3.2.1]octan-6-yl hydrogen sulfate.

(2S,5R)-2-(N-((3-(dimethylamino)cyclopentyl)sulfonyl)carbamimidoyl)-7-oxo-1,6-diazabicyclo[3.2.1]octan-6-yl hydrogen sulfate.

(2S,5R)-2-(N-((3-(methylamino)cyclopentyl)sulfonyl)carbamimidoyl)-7-oxo-1,6-diazabicyclo[3.2.1]octan-6-yl hydrogen sulfate.

(2S,5R)-2-(N-((3-acetamidocyclopentyl)sulfonyl)carbamimidoyl)-7-oxo-1,6-diazabicyclo[3.2.1]octan-6-yl hydrogen sulfate.

(2S,5R)-2-(N-((2-aminocyclopentyl)sulfonyl)carbamimidoyl)-7-oxo-1,6-diazabicyclo[3.2.1]octan-6-yl hydrogen sulfate.

(2S,5R)-2-(N-((2-(dimethylamino)cyclopentyl)sulfonyl)carbamimidoyl)-7-oxo-1,6-diazabicyclo[3.2.1]octan-6-yl hydrogen sulfate.

(2S,5R)-2-(N-((2-acetamidocyclopentyl)sulfonyl)carbamimidoyl)-7-oxo-1,6-diazabicyclo[3.2.1]octan-6-yl hydrogen sulfate.

(2S,5R)-2-(N-((2-acetamidocyclopropyl)sulfonyl)carbamimidoyl)-7-oxo-1,6-diazabicyclo[3.2.1]octan-6-yl hydrogen sulfate.

(2S,5R)-2-(N-((4-aminocyclohexyl)sulfonyl)carbamimidoyl)-7-oxo-1,6-diazabicyclo[3.2.1]octan-6-yl hydrogen sulfate.

(2S,5R)-7-oxo-2-(N-(thiophen-2-ylsulfonyl)carbamimidoyl)-1,6-diazabicyclo[3.2.1]octan-6-yl hydrogen sulfate.

(2S,5R)-7-oxo-2-(N-tosylcarbamimidoyl)-1,6-diazabicyclo[3.2.1]octan-6-yl hydrogen sulfate.

(2S,5R)-7-oxo-2-(N-(pyridin-3-ylsulfonyl)carbamimidoyl)-1,6-diazabicyclo[3.2.1]octan-6-yl hydrogen sulfate.

(2S,5R)-7-oxo-2-(N-((6-(trifluoromethyl)pyridin-3-yl)sulfonyl)carbamimidoyl)-1,6-diazabicyclo[3.2.1]octan-6-yl hydrogen sulfate.

(2S,5R)-7-oxo-2-(N-(pyridin-4-ylsulfonyl)carbamimidoyl)-1,6-diazabicyclo[3.2.1]octan-6-yl hydrogen sulfate.

(2S,5R)-2-(N-((1-methyl-1H-imidazol-4-yl)sulfonyl)carbamimidoyl)-7-oxo-1,6-diazabicyclo[3.2.1]octan-6-yl hydrogen sulfate.

(2S,5R)-2-(N-((6-fluoropyridin-3-yl)sulfonyl)carbamimidoyl)-7-oxo-1,6-diazabicyclo[3.2.1]octan-6-yl hydrogen sulfate.

(2S,5R)-2-(N-(oxazol-4-ylsulfonyl)carbamimidoyl)-7-oxo-1,6-diazabicyclo[3.2.1]octan-6-yl hydrogen sulfate.

(2S,5R)-2-(N-(oxazol-5-ylsulfonyl)carbamimidoyl)-7-oxo-1,6-diazabicyclo[3.2.1]octan-6-yl hydrogen sulfate.

(2S,5R)-7-oxo-2-(N-((2-(trifluoromethyl)thiazol-4-yl)sulfonyl)carbamimidoyl)-1,6-diazabicyclo[3.2.1]octan-6-yl hydrogen sulfate.

(2S,5R)-2-(N-((2-aminothiazol-4-yl)sulfonyl)carbamimidoyl)-7-oxo-1,6-diazabicyclo[3.2.1]octan-6-yl hydrogen sulfate.

(2S,5R)-7-oxo-2-(N-(thiazol-5-ylsulfonyl)carbamimidoyl)-1,6-diazabicyclo[3.2.1]octan-6-yl hydrogen sulfate.

(2S,5R)-2-(N-((4-cyanophenyl)sulfonyl)carbamimidoyl)-7-oxo-1,6-diazabicyclo[3.2.1]octan-6-yl hydrogen sulfate.

(2S,5R)-7-oxo-2-(N-(thiazol-2-ylsulfonyl)carbamimidoyl)-1,6-diazabicyclo[3.2.1]octan-6-yl hydrogen sulfate.

(2S,5R)-7-oxo-2-(N-((5-(trifluorormethyl)pyridin-2-yl)sulfonyl)carbamimidoyl)-1,6-diazabicyclo[3.2.1]octan-6-yl hydrogen sulfate.

(2S,5R)-2-(N-((4-fluorophenyl)sulfonyl)carbamimidoyl)-7-oxo-1,6-diazabicyclo[3.2.1]octan-6-yl hydrogen sulfate.

(2S,5R)-7-oxo-2-(N-((6-(perfluoroethyl)pyridin-3-yl)sulfonyl)carbamimidoyl)-1,6-diazabicyclo[3.2.1]octan-6-yl hydrogen sulfate.

(2S,5R)-7-oxo-2-(N-((4-(trifluoromethyl)phenyl)sulfonyl)carbamimidoyl)-1,6-diazabicyclo[3.2.1]octan-6-yl hydrogen sulfate.

(2S,5R)-7-oxo-2-(N-(thiazol-4-ylsulfonyl)carbamimidoyl)-1,6-diazabicyclo[3.2.1]octan-6-yl hydrogen sulfate.

(2S,5R)-7-oxo-2-(N-(pyrimidin-5-ylsulfonyl)carbamimidoyl)-1,6-diazabicyclo[3.2.1]octan-6-yl hydrogen sulfate.

(2S,5R)-7-oxo-2-(N-(pyrimidin-4-ylsulfonyl)carbamimidoyl)-1,6-diazabicyclo[3.2.1]octan-6-yl hydrogen sulfate.

(2S,5R)-2-(N-((5-fluoropyrimidin-2-yl)sulfonyl)carbamimidoyl)-7-oxo-1,6-diazabicyclo[3.2.1]octan-6-yl hydrogen sulfate.

(2S,5R)-7-oxo-2-(N-((2-(trifluoromethyl)pyrimidin-5-yl)sulfonyl)carbamimidoyl)-1,6-diazabicyclo[3.2.1]octan-6-yl hydrogen sulfate.

(2S,5R)-7-oxo-2-(N-((5-(trifluoromethyl)pyrimidin-2-yl)sulfonyl)carbamimidoyl)-1,6-diazabicyclo[3.2.1]octan-6-yl hydrogen sulfate.

(2S,5R)-7-oxo-2-(N-(pyridin-2-ylsulfonyl)carbamimidoyl)-1,6-diazabicyclo[3.2.1]octan-6-yl hydrogen sulfate.

(2S,5R)-2-(N-((1-methyl-1H-1,2,4-triazol-3-yl)sulfonyl)carbamimidoyl)-7-oxo-1,6-diazabicyclo[3.2.1]octan-6-yl hydrogen sulfate.

(2S,5R)-2-(N-(isoxazol-3-ylsulfonyl)carbamimidoyl)-7-oxo-1,6-diazabicyclo[3.2.1]octan-6-yl hydrogen sulfate.

(2S,5R)-2-(N-(isoxazol-4-ylsulfonyl)carbamimidoyl)-7-oxo-1,6-diazabicyclo[3.2.1]octan-6-yl hydrogen sulfate.

(2S,5R)-2-(N-((1,2,4-oxadiazol-3-yl)sulfonyl)carbamimidoyl)-7-oxo-1,6-diazabicyclo[3.2.1]octan-6-yl hydrogen sulfate.

(2S,5R)-2-(N-((5-methylisoxazol-4-yl)sulfonyl)carbamimidoyl)-7-oxo-1,6-diazabicyclo[3.2.1]octan-6-yl hydrogen sulfate.

(2S,5R)-2-(N-((1,2,5-oxadiazol-3-yl)sulfonyl)carbamimidoyl)-7-oxo-1,6-diazabicyclo[3.2.1]octan-6-yl hydrogen sulfate.

(2S,5R)-2-(N-((4-methyl-4H-1,2,4-triazol-3-yl)sulfonyl)carbamimidoyl)-7-oxo-1,6-diazabicyclo[3.2.1]octan-6-yl hydrogen sulfate.

(2S,5R)-2-(N-((1-methyl-1H-1,2,3-triazol-4-yl)sulfonyl)carbamimidoyl)-7-oxo-1,6-diazabicyclo[3.2.1]octan-6-yl hydrogen sulfate.

(2S,5R)-7-oxo-2-(N-((trifluoromethyl)sulfonyl)carbamimidoyl)-1,6-diazabicyclo[3.2.1]octan-6-yl hydrogen sulfate.

(2S,5R)-2-(N-((difluoromethyl)sulfonyl)carbamimidoyl)-7-oxo-1,6-diazabicyclo[3.2.1]octan-6-yl hydrogen sulfate.

(2S,5R)-2-(N-((fluoromethyl)sulfonyl)carbamimidoyl)-7-oxo-1,6-diazabicyclo[3.2.1]octan-6-yl hydrogen sulfate.

(2S,5R)-2-(N-((2,5-dichlorothiophen-3-yl)sulfonyl)carbamimidoyl)-7-oxo-1,6-diazabicyclo[3.2.1]octan-6-yl hydrogen sulfate.

(2S,5R)-2-(N-(furan-2-ylsulfonyl)carbamimidoyl)-7-oxo-1,6-diazabicyclo[3.2.1]octan-6-yl hydrogen sulfate.

(2S,5R)-7-oxo-2-(N-sulfamoylcarbamimidoyl)-1,6-diazabicyclo[3.2.1]octan-6-yl hydrogen sulfate.

(2S,5R)-2-(N—N-methylsulfamoyl)carbamimidoyl)-7-oxo-1,6-diazabicyclo[3.2.1]octan-6-yl hydrogen sulfate.

(2S,5R)-2-(N—(N-(acetamidomethyl)sulfamoyl)carbamimidoyl)-7-oxo-1,6-diazabicyclo[3.2.1]octan-6-yl hydrogen sulfate.

(2S,5R)-2-(N—(N-(aminomethyl)sulfamoyl)carbamimidoyl)-7-oxo-1,6-diazabicyclo[3.2.1]octan-6-yl hydrogen sulfate.

(2S,5R)-2-(N—(N-ethylsulfamoyl)carbamimidoyl)-7-oxo-1,6-diazabicyclo[3.2.1]octan-6-yl hydrogen sulfate.

(2S,5R)-2-(N-(azetidin-1-ylsulfonyl)carbamimidoyl)-7-oxo-1,6-diazabicyclo[3.2.1]octan-6-yl hydrogen sulfate.

(2S,5R)-2-(N—(((R)-1-acetylpyrrolidin-3-yl)sulfonyl)carbamimidoyl)-7-oxo-1,6-diazabicyclo[3.2.1]octan-6-yl hydrogen sulfate.

(2S,5R)-2-(N-((1-methylpiperidin-4-yl)sulfonyl)carbamimidoyl)-7-oxo-1,6-diazabicyclo[3.2.1]octan-6-yl hydrogen sulfate.

(2S,5R)-2-(N—(((S)-1-acetylpyrrolidin-3-yl)sulfonyl)carbamimidoyl)-7-oxo-1,6-diazabicyclo[3.2.1]octan-6-yl hydrogen sulfate.

(2S,5R)-2-(N—(((S)-1-methylpyrrolidin-3-yl)sulfonyl)carbamimidoyl)-7-oxo-1,6-diazabicyclo[3.2.1]octan-6-yl hydrogen sulfate.

(2S,5R)-2-(N-((1-acetylpiperidin-4-yl)sulfonyl)carbamimidoyl)-7-oxo-1,6-diazabicyclo[3.2.1]octan-6-yl hydrogen sulfate.

(2S,5R)-2-(N—(((S)-1-(methylsulfonyl)pyrrolidin-3-yl)sulfonyl)carbamimidoyl)-7-oxo-1,6-diazabicyclo[3.2.1]octan-6-yl hydrogen sulfate.

(2S,5R)-2-(N—(((R)-1-(methylsulfonyl)pyrrolidin-3-yl)sulfonyl)carbamimidoyl)-7-oxo-1,6-diazabicyclo[3.2.1]octan-6-yl hydrogen sulfate.

(2S,5R)-2-(N-((1-(methylsulfonyl)piperidin-3-yl)sulfonyl)carbamimidoyl)-7-oxo-1,6-diazabicyclo[3.2.1]octan-6-yl hydrogen sulfate.

(2S,5R)-2-(N—(N-isopropylsulfamoyl)carbamimidoyl)-7-oxo-1,6-diazabicyclo[3.2.1]octan-6-yl hydrogen sulfate.

(2S,5R)-2-(N—(N-methyl-N-(2,2,2-trifluoroethyl)sulfamoyl)carbamimidoyl)-7-oxo-1,6-diazabicyclo[3.2.1]octan-6-yl hydrogen sulfate.

(2S,5R)-2-(N—(N-isobutyl-N-methylsulfamoyl)carbamimidoyl)-7-oxo-1,6-diazabicyclo[3.2.1]octan-6-yl hydrogen sulfate.

(2S,5R)-2-(N—(N-(tert-butyl)sulfamoyl)carbamimidoyl)-7-oxo-1,6-diazabicyclo[3.2.1]octan-6-yl hydrogen sulfate.

(2S,5R)-2-(N—(N-(methoxycarbonyl)sulfamoyl)carbamimidoyl)-7-oxo-1,6-diazabicyclo[3.2.1]octan-6-yl hydrogen sulfate.

(2S,5R)-2-(N-(isocyanatosulfonyl)carbamimidoyl)-7-oxo-1,6-diazabicyclo[3.2.1]octan-6-yl hydrogen sulfate.

(2S,5R)-2-(N—(N-(2-cyanoethyl)-N-methylsulfamoyl)carbamimidoyl)-7-oxo-1,6-diazabicyclo[3.2.1]octan-6-yl hydrogen sulfate.

(2S,5R)-2-(N—(N-ethyl-N-methylsulfamoyl)carbamimidoyl)-7-oxo-1,6-diazabicyclo[3.2.1]octan-6-yl hydrogen sulfate.

(2S,5R)-2-(N—N-(2-chloroethyl)sulfamoyl)carbamimidoyl)-7-oxo-1,6-diazabicyclo[3.2.1]octan-6-yl hydrogen sulfate.

(2S,5R)-7-oxo-2-(N—N-propionylsulfamoyl)carbamimidoyl)-1,6-diazabicyclo[3.2.1]octan-6-yl hydrogen sulfate.

methyl 4-(N-(imino((2S,5R)-7-oxo-6-(sulfooxy)-1,6-diazabicyclo[3.2.1]octan-2-yl)methyl)sulfamoyl)piperazine-1-carboxylate.

(2S,5R)-2-(N-((4-methylpiperazin-1-yl)sulfonyl)carbamimidoyl)-7-oxo-1,6-diazabicyclo[3.2.1]octan-6-yl hydrogen sulfate.

(2S,5R)-2-(N-((4-acetylpiperazin-1-yl)sulfonyl)carbamimidoyl)-7-oxo-1,6-diazabicyclo[3.2.1]octan-6-yl hydrogen sulfate.

(2S,5R)-2-(N-((1-methyl-1H-imidazol-2-yl)sulfonyl)carbamimidoyl)-7-oxo-1,6-diazabicyclo[3.2.1]octan-6-yl hydrogen sulfate.

(2S,5R)-2-(N-((6-methoxypyridin-3-yl)sulfonyl)carbamimidoyl)-7-oxo-1,6-diazabicyclo[3.2.1]octan-6-yl hydrogen sulfate.

(2S,5R)-2-(N-((5-methoxypyridin-2-yl)sulfonyl)carbamimidoyl)-7-oxo-1,6-diazabicyclo[3.2.1]octan-6-yl hydrogen sulfate.

(2S,5R)-2-(N-((5-fluoropyridin-2-yl)sulfonyl)carbamimidoyl)-7-oxo-1,6-diazabicyclo[3.2.1]octan-6-yl hydrogen sulfate.

(2S,5R)-7-oxo-2-(N-(pyrazin-2-ylsulfonyl)carbamimidoyl)-1,6-diazabicyclo[3.2.1]octan-6-yl hydrogen sulfate.

The present invention also relates to methods for the preparation of compounds of formula (I). The compounds of the present invention of formula (I) can be readily prepared by the following reaction Scheme 1 and examples using readily available starting materials, reagents and conventional synthesis procedures known to those of ordinary skill in this art.

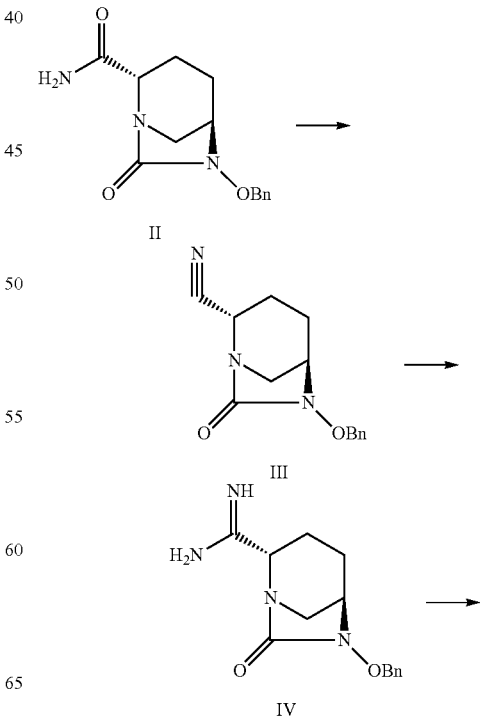

SCHEME 1

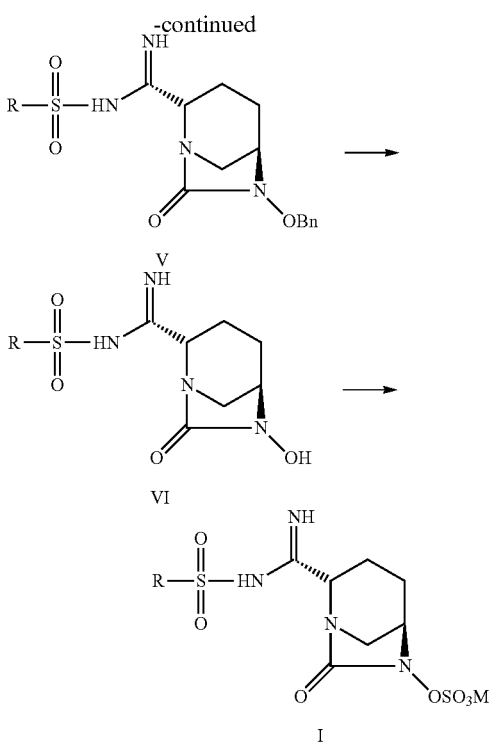

The key intermediate amide (II) may be prepared following the literature (Org. Process Res. Dev. 2016, 20, 1799-1805).

Compounds of the general of formula (I) can be prepared by converting the bicyclic amide (II) to the nitrile (III) in presence of a suitable reagents. The suitable reagents used for carrying out this step include, but are not limited to trifluoroacetic anhydride (TFAA) and triethylamine (TEA) or diisopropylethylamine (DIPEA), phosphoryl chloride (POCl$_3$) and TEA, and the like. The organic solvents useful in the reaction are not particularly limited and include any of those which do not adversely affect the reaction. Typical solvents include dichlomethane, chloroform, tetrahydrofuran and the like. The reaction is normally carried out at a temperature of from about 0° C. to 40° C., and preferably at room temperature under nitrogen. After completion of the reaction the desired product can be easily separated by conventional methods such as column chromatography, crystallization or similar methods.

The intermediate amidine (IV) can be prepared by substituting an ammonium (NH$_3$, or an appropriately ammonium salt form) to the nitrile (III) in presence of a suitable reagent. An appropriately ammonium salt such as ammonium chloride (NH$_4$Cl), ammonium bromide (NH$_4$Br), ammonium sulfate (NH$_4$SO$_4$) may be included. The suitable reagents useful for carrying out this step include, but are not limited to, trimethylaluminum, or triethylaluminum, or trifluoromethanesulfonate, or Lanthanum and the like. The organic solvents useful in the reaction are not particularly limited and include any of those which do not adversely affect the reaction. Typical solvents include dichloromethane, chloroform, toluene, dimethylformamide, tetrahydrofuran, dimethylsulfoxide, and the like. The reaction is normally carried out at a temperature of from about 0° C. to about 100° C. After completion of the reaction, the desired product can be easily separated by conventional methods such as column chromatography, crystallization or similar methods.

The intermediate amide (V) may be prepared by coupling the amidine (IV) with an appropriate sulfonyl chloride (R—SO$_2$Cl) or an appropriate sulfonic anhydride (R—SO$_2$—O—SO$_2$—R) in presence of a suitable reagent. The suitable reagents useful for carrying out this step include, but are not limited to, trimethylamine (TEA), triethylamine, N,N-diisopropylethylamine (DIPEA), and 4-dimethylaminopyridine (DMAP), N-methyl morpholine and the like. The organic solvents useful in the reaction are not particularly limited and include any of those which do not adversely affect the reaction. Typical solvents include dichloromethane, ethylacetate, dimethylformamide, tetrahydrofuran, dimethylsulfoxide, and the like. The reaction is normally carried out at a temperature of from about 0° C. to about 100° C. After completion of the reaction the desired product can be easily separated by conventional methods such as column chromatography, crystallization or similar methods.

In the following step, the intermediate amide (V) could be converted to the hydroxy compound (VI) under an atmosphere of hydrogen or hydrogen mixed with an inert diluent such as nitrogen or argon in the presence of a hydrogenation catalyst. The catalysts used in this hydrogenation reaction are the type of agents known in the art for this kind of deprotection and typical examples are the noble metals, such as nickel, palladium, platinum and rhodium. Examples of the catalysts are platinum, platinum oxide, palladium, palladium oxide and the like. The catalyst is usually present in the amount from about 1 to about 50 weight percent and preferably from about 5 to about 15 weight percent based on the compound of V. It is often convenient to suspend the catalyst on an inert support. A particularly convenient catalyst is palladium suspended on an inert support such as carbon, e.g., 5% or 10% by weight palladium on carbon. This reaction may be conveniently effected at ambient temperature from 15 psi to 60 psi until reaction is complete (2 to 72 hours). Suitable solvents for this reaction are those which substantially dissolve the starting material of the formula (V), after reaction, the suitable solvents are sufficiently volatile to be removed by evaporation and do not themselves suffer hydrogenation. Examples of such solvents include methanol, ethanol, dioxane, ethyl acetate, tetrahydrofuran or a mixture of these solvents. Upon completion, the hydroxy intermediate (VI) can be purified by silica gel column chromatography or in many cases can be directly carried out to the next step without further purification.

Finally, the compound of formula (I) can be achieved by sulfation of the hydroxy intermediate (VI) using a sulfating reagent (e.g., pyridine-SO$_3$ complex, NMe$_3$-SO$_3$ complex, DMF-SO$_3$ complex or ClSO$_3$H) in an appropriate base (e.g., pyridine, triethylamine or 2-picoline) as described in the literature (WO2017155765A1, Org. Process Res. Dev. 2016, 20, 1799-1805). Thus, pyridine-SO$_3$ complex or SO$_3$—NMe$_3$ complex can be added to a solution of the hydroxy intermediate (VI) in a solvent in excess amount, if desired, to force the reaction to completion. The organic solvents useful for this transformation are not particularly limited and include those which do not adversely affect the reaction. Typical solvents include, but are not limited to, pyridine, tertrahydrofuran, isopropyl alcohol and water, dimethyl formamide, dimethylacetamide, acetonitrile, and the like. The transformation can be carried out at from 0° C. to 40° C., and more preferably at room temperature.

The compound of formula (I) also can be achieved by treating the sulfated intermediate with an acid to remove protecting group when the intermediate (VI) containing protection group, such as Boc., and the like. The treatment is suitably conducted at a temperature in a range from about −10° C. to about 100° C. and is typically conducted at a temperature in a range of from about 0° C. to about 35° C.

Suitable purification methods for the final compound of formula (I) are normal silica gel chromatograph, preparative HPLC, HP20 chromatograph, inon exchange resin and the like.

The compounds of the present invention of formula (I) also can be readily prepared by the following reaction Scheme 2 and examples using readily available starting materials, reagents and conventional synthesis procedures known to those of ordinary skill in this art.

SCHEME 2

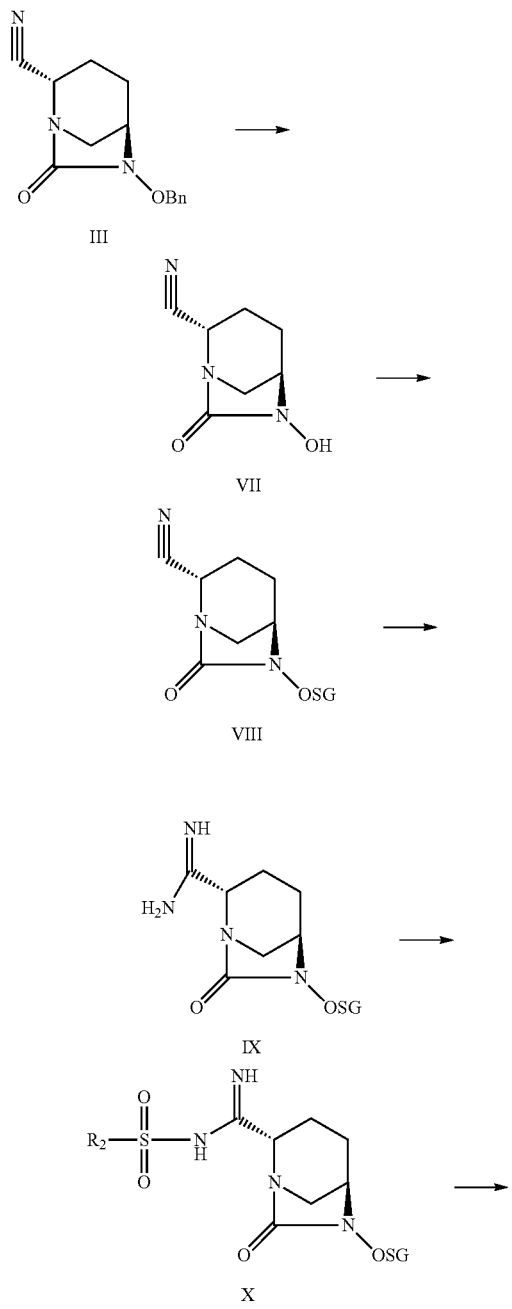

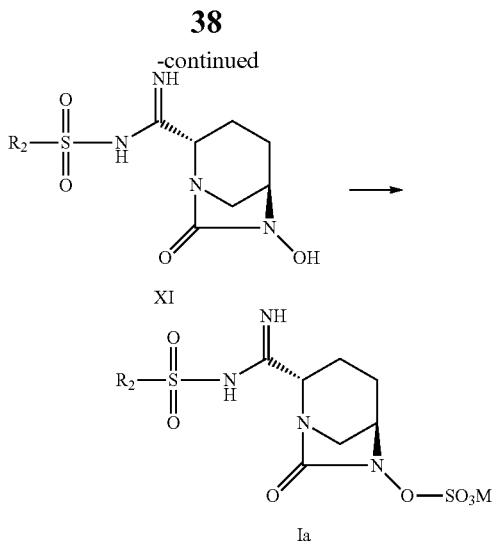

The key intermediate nitrile (III) could be converted to the hydroxy compound (VII) under an atmosphere of hydrogen or hydrogen mixed with an inert diluent such as nitrogen or argon in the presence of a hydrogenation catalyst. The catalysts used in this hydrogenation reaction are the type of agents known in the art for this kind of deprotection and typical examples are the noble metals, such as nickel, palladium, platinum and rhodium. Examples of the catalysts are platinum, platinum oxide, palladium, palladium oxide and the like. The catalyst is usually present in the amount from about 1 to about 50 weight percent and preferably from about 5 to about 15 weight percent based on the compound (III). It is often convenient to suspend the catalyst on an inert support. A particularly convenient catalyst is palladium suspended on an inert support such as carbon, e.g., 5% or 10% by weight palladium on carbon. This reaction may be conveniently effected at ambient temperature from 15 psi to 60 psi until reaction is complete (2 to 72 hours). Suitable solvents for this reaction are those which substantially dissolve the starting material of the formula (III), after reaction, the suitable solvents are sufficiently volatile to be removed by evaporation and do not themselves suffer hydrogenation. Examples of such solvents include methanol, ethanol, dioxane, ethyl acetate, tetrahydrofuran or a mixture of these solvents. Upon completion, the hydroxy intermediate (VII) can be purified by silica gel column chromatography or in many cases can be directly carried out to the next step without further purification.

The intermediate silyl ether (VIII) can be prepared by protecting the hydroxy compound (VII) with proper silane group (SG) in presence of a suitable base reagent. A proper protecting silane reagent includes, such as chlorotrimethylsilane (TMSCl), tert-butyldimethylchlorosilane (TBSCl), tert-butyldiphenylsilyl chloride (TBDPSCl) and the like. A suitable base reagent includes, such as imidazole, triethylamine and the like. The organic solvents useful in the reaction are not particularly limited and include any of those which do not adversely affect the reaction. Typical solvents include dichloromethane, chloroform, dimethylformamide, tetrahydrofuran and the like. The reaction is normally carried out at a temperature of from about 0° C. to about 100° C. After completion of the reaction the desired product can be easily separated by conventional methods such as column chromatography, crystallization or similar methods.

The intermediate amidine (IX) can be prepared by substituting an ammonium (NH₃, or an appropriately ammonium salt) to the nitrile (VIII) in presence of a suitable reagent. An appropriately ammonium salt such as ammonium chloride ($NH_4Cl$), ammonium bromide ($NH_4Br$), ammonium sulfate ($NH_4SO_4$) may be included. The suitable reagents useful for carrying out this step include, but are not limited to, trimethylaluminum, or triethylaluminum, or trifluoromethanesulfonate, or Lanthanum (III) and the like. The organic solvents useful in the reaction are not particularly limited and include any of those which do not adversely affect the reaction. Typical solvents include dichloromethane, chloroform, toluene, dimethylformamide, tetrahydrofuran, dimethylsulfoxide, and the like. The reaction is normally carried out at a temperature of from about 0° C. to about 100° C. After completion of the reaction the desired product can be easily separated by conventional methods such as column chromatography, crystallization or similar methods.

In the following step, the intermediate amide (×) may be prepared by coupling the amidine (IX) with an appropriate sulfonyl chloride ($R_2$—$SO_2Cl$) or sulfonic anhydride ($R_2$—$SO_2$—$O$—$SO_2$—$R_2$) in presence of a suitable reagent. The suitable reagents useful for carrying out this step include, but are not limited to, trimethylamine (TEA), triethylamine, N,N-diisopropylethylamine (DIPEA), and 4-dimethylaminopyridine (DMAP), N-methyl morpholine and the like. The organic solvents useful in the reaction are not particularly limited and include any of those which do not adversely affect the reaction. Typical solvents include dichloromethane, ethylacetate, dimethylformamide, tetrahydrofuran, dimethylsulfoxide, and the like. The reaction is normally carried out at a temperature of from about 0° C. to about 100° C. After completion of the reaction the desired product can be easily separated by conventional methods such as column chromatography, crystallization or similar methods.

The intermediate amide (X) could be converted to the hydroxy compound (XI) by deprotecting reaction in presence of a suitable reagent. The suitable reagents used for carrying out this step include, but are not limited to tetra-n-butylammonium fluoride (TBAF), acetic acid, hydrogen fluoride, trifluoroacetic acid and the like. The organic solvents useful in the reaction are not particularly limited and include any of those which do not adversely affect the reaction. Typical solvents include tetrahydrofuran, dichloromethane and the like. The reaction is normally carried out at a temperature of from about 0° C. to 40° C., and preferably at room temperature under nitrogen. After completion of the reaction the desired product can be easily separated by conventional methods such as column chromatography, crystallization or similar methods.

Finally, the compound of formula (Ia) can be achieved by sulfation of the hydroxy intermediate (XI) using a similar sulfating reagent above, the reaction condition and the purification methods described in Scheme 1.

EXAMPLES

Abbreviations

In the experiments the following abbreviations have been used:
δ: chemical shift in parts per million (ppm) by frequency
br s: broad single in NMR
d: doublet in NMR
dd: doublet of doublet in NMR
t: triplet in NMR
q: quartet in NMR
m: multiplet in NMR
J: coupling constant in NMR
Hz: hertz
MHz: megahertz
NMR: nuclear magnetic resonance
$ES^-$: negative ion mode in electrospray ionization mass spectrometry
$ES^+$: positive ion mode in electrospray ionization mass spectrometry
MS: mass spectrum
HPLC: high performance liquid chromatography
g: gram(s)
mg: milligram(s)
mmol: millimole(s)
mol: mole(s)
L: liter(s)
mL: milliliter(s)
M: molarity
h: hour(s)
min: minute(s)
Pd/C: palladium on carbon
DMAP: 4-dimethylaminopyridine
TEA: triethylamine
DIPEA: N,N-diisopropylethylamine
TFAA: trifluoroacetic anhydride
DCM: dichloromethane
DMF: dimethylformamide
DMSO: dimethyl sulfoxide
EtOAc: ethyl acetate
TFA: trifluoroacetic acid
THF: tertrahydrofuran
TLC: thin layer chromatography
TMS: tetramethylsilane
$CDCl_3$: deuterated chloroform
$CD_3OD$: deuterated methanol
$D_2O$: deuterium oxide
DMSO-$d_6$ deuterium dimethyl sulfoxide
pH: the negative logarithm of the hydrogen ion concentration
Boc: N-tert-butoxycarbonyl
Bn: benzyl
HPLC: high-performance liquid chromatography Analytical Methods All $^1H$ and $^{19}F$ NMR spectra were recorded on a Bruker AVANCE NEO 400 NMR operating at 400 MHz for $^1H$, and 376 MHz for $^{19}F$ respectively. NMR data was recorded in chemical shifts relative to tetramethylsilane (TMS) as internal standard. NMR spectra were run either in $CDCl_3$ containing 0.05% TMS, $CD_3OD$ containing 0.05% TMS, $D_2O$ or DMSO-$d_6$ containing 0.03% TMS.

Preparative HPLC was performed on an Agilent 1260 Infinity II System on Agilent 10 prep-C18 250×21.2 mm column, using an acetonitrile/aqueous 0.1% trifluoroacetic acid gradient, or an acetonitrile/aqueous 0.1% formic acid gradient at 22° C.

Mass spectra were performed on an Agilent 1260II-6125 Separation Module using either $ES^-$ or $ES^+$ ionization modes.

Column Chromatography was performed with using Qingdao Inc. Silica Gel: CC Grade (230-400 Mesh).

Commercial solvents and reagents were generally used without further purification. All products were dried before characterisation and use in subsequent synthetic steps.

1. General Synthetic Methods

1.1 Synthesis of (2S,5R)-6-(benzyloxy)-7-oxo-1,6-diazabicyclo[3.2.1]octane-2-carboximidamide (BB-1)

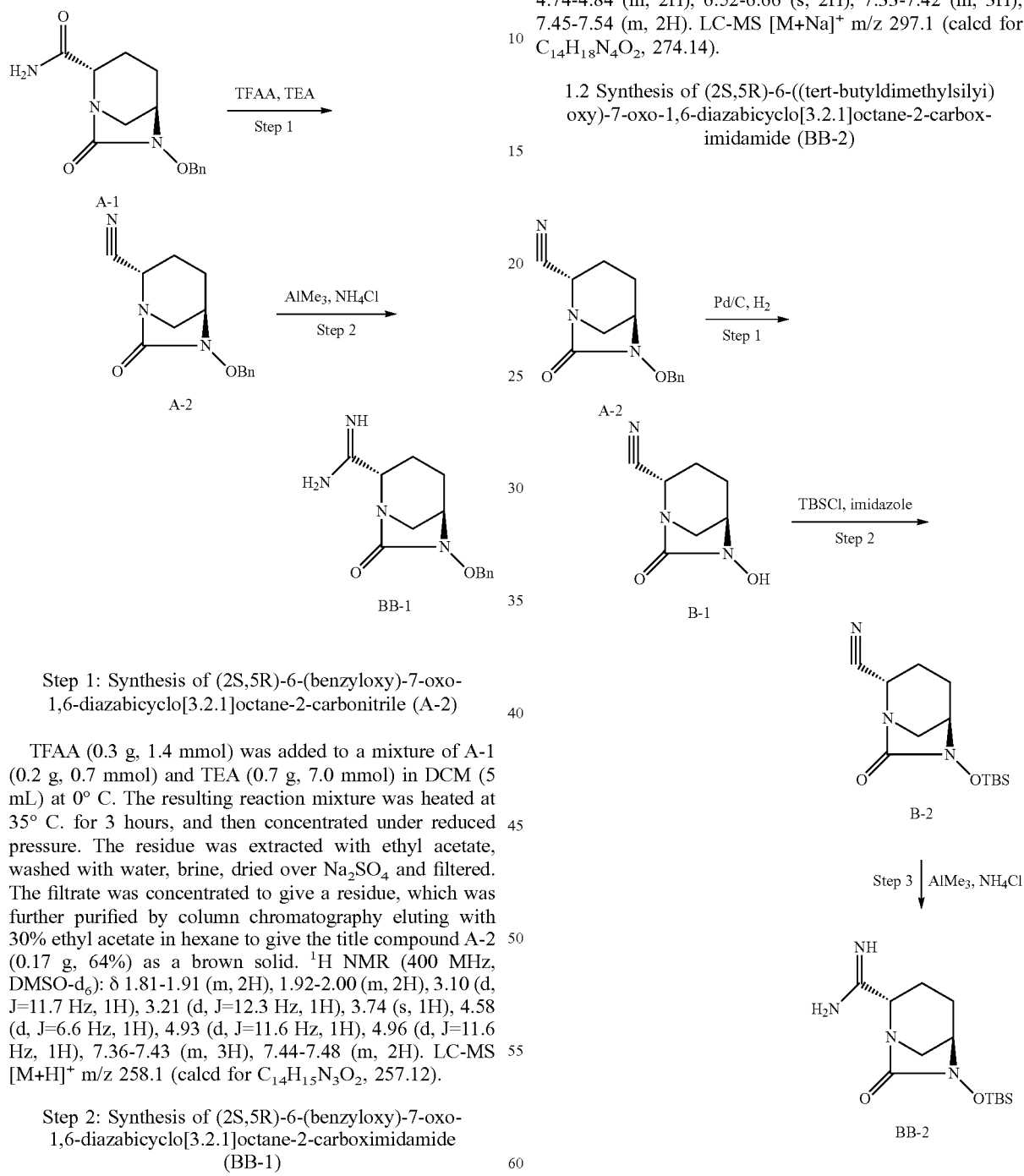

Step 1: Synthesis of (2S,5R)-6-(benzyloxy)-7-oxo-1,6-diazabicyclo[3.2.1]octane-2-carbonitrile (A-2)

TFAA (0.3 g, 1.4 mmol) was added to a mixture of A-1 (0.2 g, 0.7 mmol) and TEA (0.7 g, 7.0 mmol) in DCM (5 mL) at 0° C. The resulting reaction mixture was heated at 35° C. for 3 hours, and then concentrated under reduced pressure. The residue was extracted with ethyl acetate, washed with water, brine, dried over $Na_2SO_4$ and filtered. The filtrate was concentrated to give a residue, which was further purified by column chromatography eluting with 30% ethyl acetate in hexane to give the title compound A-2 (0.17 g, 64%) as a brown solid. $^1$H NMR (400 MHz, DMSO-$d_6$): δ 1.81-1.91 (m, 2H), 1.92-2.00 (m, 2H), 3.10 (d, J=11.7 Hz, 1H), 3.21 (d, J=12.3 Hz, 1H), 3.74 (s, 1H), 4.58 (d, J=6.6 Hz, 1H), 4.93 (d, J=11.6 Hz, 1H), 4.96 (d, J=11.6 Hz, 1H), 7.36-7.43 (m, 3H), 7.44-7.48 (m, 2H). LC-MS $[M+H]^+$ m/z 258.1 (calcd for $C_{14}H_{15}N_3O_2$, 257.12).

Step 2: Synthesis of (2S,5R)-6-(benzyloxy)-7-oxo-1,6-diazabicyclo[3.2.1]octane-2-carboximidamide (BB-1)

$AlMe_3$ in n-hexane (2 N, 9.0 mL, 18.0 mmol) and $NH_4Cl$ (0.96 g, 18.0 mmol) were added to a solution of A-2 (3.08 g, 15.0 mmol) in anhydrous DCM (45 mL) at 0° C. The reaction mixture was stirred at room temperature overnight, cooled to 0° C., quenched by addition of silica gel (8 g) and methanol (8 mL). The resulting mixture was stirred at room temperature for 20 min, filtered off, rinsed with 10% methanol in DCM (2×30 mL). The filtrate was concentrated and purified by flash column chromatography using 2-5% MeOH in DCM to give the title compound BB-1 (1.45 g, 44%) as a white solid. $^1$H NMR (400 MHz, DMSO-$d_6$): δ 1.61-1.79 (m, 2H), 1.80-1.92 (m, 2H), 2.77-2.95 (m, 2H), 3.12-3.21 (s, 1H), 3.80-3.92 (m, 1H), 4.09-4.15 (m, 1H), 4.74-4.84 (m, 2H), 6.52-6.66 (s, 2H), 7.33-7.42 (m, 3H), 7.45-7.54 (m, 2H). LC-MS $[M+Na]^+$ m/z 297.1 (calcd for $C_{14}H_{18}N_4O_2$, 274.14).

1.2 Synthesis of (2S,5R)-6-((tert-butyldimethylsilyi)oxy)-7-oxo-1,6-diazabicyclo[3.2.1]octane-2-carboximidamide (BB-2)

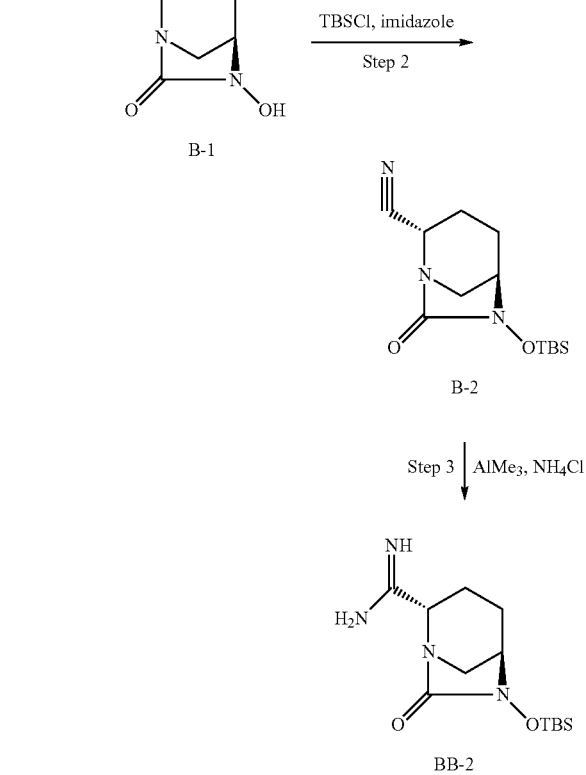

Step 1: Synthesis of (2S,5R)-6-hydroxy-7-oxo-1,6-diazabicyclo[3.2.1]octane-2-carbonitrile (B-1)

Wet 5% Pd/C (720 mg) was added to a solution of compound A-2 (3.5 g, 13.6 mmol) in EtOAc and DCM (2:1, 15 mL), and then hydrogenated at room temperature under 45 psi pressure for 2 hours. After completion of reaction, the catalyst was removed by celite filtration and washed with EtOAc. The filtrate was concentrated to obtain the pale yellow compound B-1 (2.1 g, 95%) as a crude product which was used without purification for further reaction. $^1$H NMR (400 MHz, CDCl$_3$): δ 1.68-1.70 (m, 1H), 1.87-1.93 (m, 2H), 2.05-2.18 (m, 1H), 3.14-3.25 (m, 2H), 4.01-4.14 (m, 1H), 5.21 (br s, 1H). LC-MS [M+H]$^+$ m/z 168.1 (calcd for C$_7$H$_9$N$_3$O$_2$, 167.07).

Step 2: Synthesis of (2S,5R)-6-((tert-butyldimethyl-silypoxy)-7-oxo-1,6-diazabicyclo[3.2.1]octane-2-carbonitrile (B-2)

Tert-butyldimethylsilyl chloride (2 g, 13.5 mmol) was added to a stirred solution of compound B-1 (1.5 g, 9 mmol) and imidazole (1.2 g, 18 mmol) in DCM (20 mL). The reaction mixture was stirred at room temperature overnight. The solids formed were filtered and the filtrate was washed with 0.1 N HCl followed by water and brine. The organic layer was dried over MgSO$_4$ and concentrated to furnish the crude product which was purified by column chromatography using DCM as a solvent to give the title compound B-2 (1.16 g, 46%) as a white solid. $^1$H NMR (400 MHz, CDCl$_3$): δ 0.00 (s, 3H), 0.06 (s, 3H), 0.78 (s, 9H), 1.69-1.76 (m, 2H), 2.00-2.13 (m, 2H), 3.00 (d, J=11.5 Hz, 1H), 3.19 (d, J=12.2 Hz, 1H), 3.46 (s, 1H), 4.17 (d, J=7.2 Hz, 1H). LC-MS [M+H]$^+$ m/z 282.2 (calcd for C$_{13}$H$_{23}$N$_3$O$_2$Si, 281.16).

Step 3: Synthesis of (2S,5R)-6-((tert-butyldimethyl-silypoxy)-7-oxo-1,6-diazabicyclo[3.2.1]octane-2-carboximidamide (BB-2)

Trimethylaluminum (2 M in hexane, 2.9 mL, 5.8 mmol) was added dropwise to a suspension of ammonium chloride (358 mg, 5.87 mmol) in DCM (10 mL) at room temperature. The suspension was further stirred for 30 minutes followed by the dropwise addition of compound B-2 (1.1 g, 3.9 mmol) dissolved in DCM (10 mL). The reaction mixture was stirred overnight at room temperature while the progress of reaction was monitored by LCMS. Another portion of NH$_4$Cl (358 mg, 5.87 mmol) and trimethylaluminum (2.9 mL, 5.8 mmol) was further added. The reaction mixture was further stirred at room temperature for 24 hours. Upon completion of reaction MeOH (50 mL) was added dropwise to quench the unreacted trimethylaluminum. Bulk of solid formed was filtered and the filter cake was washed with MeOH. The filtrate was concentrated to afford the white solid which was purified by column chromatography using DCM containing 2-4% MeOH to give the title product BB-2 (263 mg, 23%) as a white solid. $^1$H NMR (400 MHz, CDCl$_3$): δ 0.00 (s, 6H), 0.77 (s, 9H), 1.62-1.66 (m, 2H), 1.73-1.78 (m, 1H), 1.83-1.87 (m, 1H), 2.80 (dd, J=11.2 Hz, 3.18 Hz, 1H), 2.95 (t, J=11.2 Hz, 1H), 3.64-3.72 (m, 1H), 3.80 (d, J=2.1 Hz, 1H), 5.76 (br s, 2H). LC-MS [M+H]$^+$ m/z 299.2 (calcd for C$_{13}$H$_{26}$N$_4$O$_2$Si, 298.18).

2. Synthesis of the Final Compound

Example 1

Sodium (2S,5R)-7-oxo-2-(N-((2,2,2-trifluoroethyl)sulfonyl)caramimidoyl)-1,6-diazabicyclo[3.2.1]octan-6-yl sulfate (Compound 3 in Table 1)

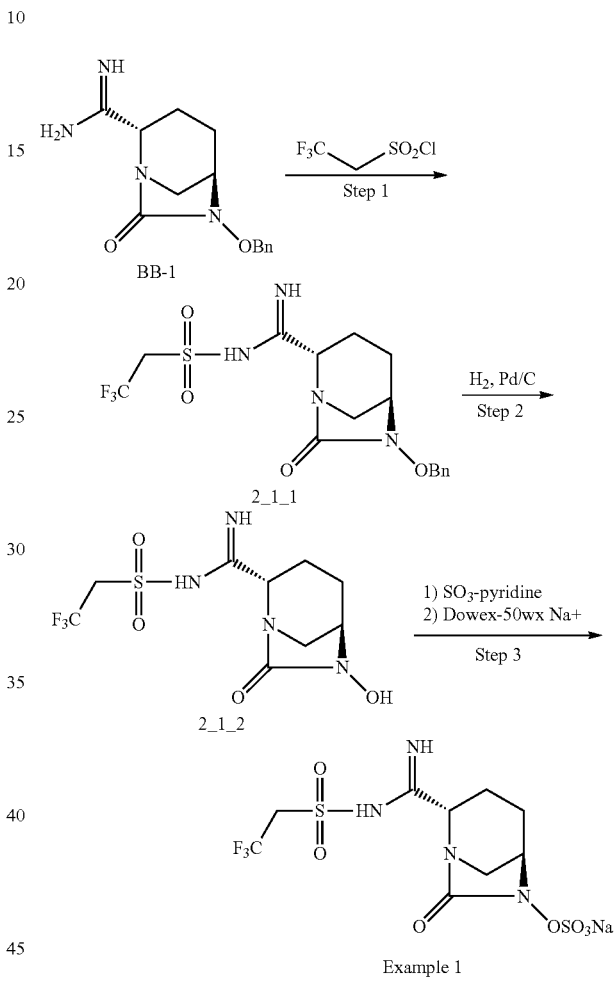

Example 1

Step 1: Synthesis of (2S,5R)-6-(benzyloxy)-7-oxo-N-((2,2,2-trifluoroethyl)-1,6-diazabicyclo[3.2.1]octane-2-carboximidamide (2_1_1)

2,2,2-Trifluoroethane-1-sulfonyl chloride (0.11 mL, 1.01 mmol) and TEA (0.31 mL, 2.22 mmol) were added to a suspension of BB-1 (205 mg, 0.75 mmol) in CH$_2$Cl$_2$ (8 mL) at 0° C. and then stirred overnight at room temperature. The reaction mixture was diluted with CH$_2$Cl$_2$ (30 mL), washed with saturated NaHCO$_3$, brine, dried over Na$_2$SO$_4$ and filtered. The organic layer was concentrated to give a residue, which was purified by silica gel column chromatography eluting with 50% ethyl acetate in petroleum ether to give the title compound 2_1_1 (252 mg, 80%) as a white foam. $^1$H NMR (400 MHz, DMSO-d$_6$): δ 1.78-1.95 (m, 3H), 2.04-2.12 (m, 1H), 3.15 (t, J=11.9 Hz, 1H), 3.67-3.78 (m, 1H), 3.91-4.01 (m, 1H), 4.64-4.76 (m, 1H), 4.77-4.91 (m, 3H), 5.15 (s, 1H), 6.76 (s, 2H), 7.33-7.43 (m, 3H), 7.45-7.54

(m, 2H). $^{19}$F NMR (376 MHz, DMSO-d$_6$): δ −60.69 (t, J=9.7 Hz, 3F). LC-MS [M+Na]$^+$ m/z 443.1 (calcd for C$_{16}$H$_{19}$F$_3$N$_4$O$_4$S, 420.11).

Step 2: Synthesis of (2S,5R)-6-hydroxy-7-oxo-N-((2,2,2,-trifluoroethyl)sulfonyl)-1,6-diazabicyclo[3.2.1]octane-2-carboximidamide (2_1_2)

10% Pd/C (200 mg) was added to a solution of compound 2_1_1 (250 mg, 0.59 mmol) in THF (10 mL) with a few drops of TEA. The mixture was stirred under H$_2$ (balloon) at room temperature for 2 hours, filtered through a pad of celite, rinsed with EtOAc (2×10 mL). The filtrate was concentrated to give a residue, which was purified by silica gel column chromatography eluting with 2-5% MeOH in CH$_2$Cl$_2$ to give the title compound 2_1_2 (160 mg, 81%) as a pale yellow solid. $^1$H NMR (400 MHz, DMSO-d$_6$): δ 1.67-1.90 (m, 3H), 2.02-2.13 (m, 1H), 3.09 (t, J=11.9 Hz, 1H), 3.63-3.71 (m, 1H), 3.95-4.03 (m, 1H), 4.70-4.92 (m, 2H), 5.14 (s, 1H), 6.51 (s, 2H), 9.30 (s, 1H). $^{19}$F NMR (376 MHz, DMSO-d$_6$): δ −60.82 (t, J=9.7 Hz, 3F). LC-MS [M+Na]$^+$ m/z 353.0 (calcd for C$_9$H$_{13}$F$_3$N$_4$O$_4$S, 330.06).

Step 3: Synthesis of sodium (2S,5R)-7-oxo-2-(N-((2,2,2-trifluoroethyl)sulfonyl)caramimidoyl)-1,6-diazabicyclo[3.2.1]octan-6-yl sulfate (Example 1)

SO$_3$-pyridine (130 mg, 0.82 mmol) was added to a solution of 2_1_2 (80 mg, 0.25 mmol) in pyridine (2 mL). The reaction mixture was stirred at room temperature overnight and concentrated under reduced pressure to provide a residue. The residue was purified by resin Dowex-50wx Na$^+$ exchange, using water as elution solvent to give example 1 (97 mg, 90%) as a white solid. $^1$H NMR (400 MHz, D$_2$O) δ 1.87-2.05 (m, 3H), 2.09-2.15 (m, 1H), 3.32-3.39 (m, 1H), 3.84-3.90 (m, 1H), 3.98-4.06 (m, 1H), 4.31-4.43 (m, 2H), 5.11 (br s, 1H). $^{19}$F NMR (376 MHz, D$_2$O): δ −61.9 (t, J=9.6 Hz). LC-MS [M−Na]$^-$ m/z 409.0 (calcd for C$_9$H$_{12}$F$_3$N$_4$NaO$_7$S$_2$, 432.00).

Example 2

Sodium (2S,5R)-2-(N-((2-methoxy-2-oxoethyl)sulfonyl)caramimidoyl)-7-oxo-1,6-diazabicyclo[3.2.1]octan-6-yl sulfate (Compound 19 in Table 1)

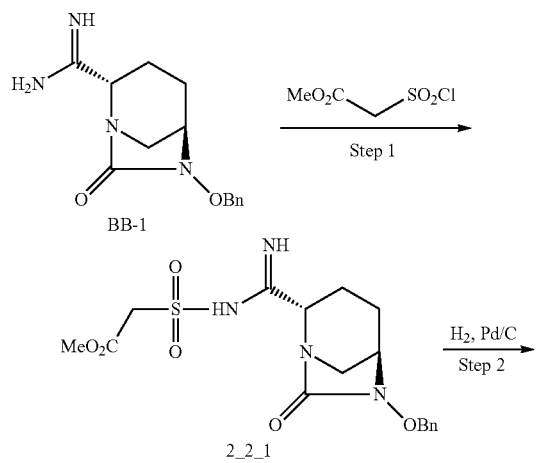

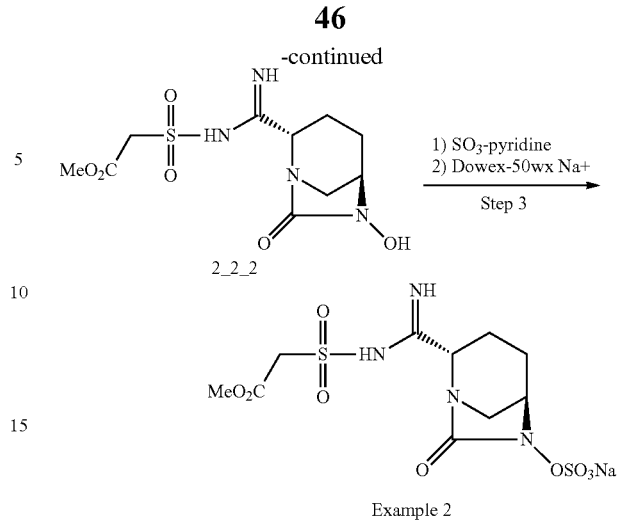

Step 1: Synthesis of methyl 2-(N-(((2S,5R)-6-(benzyloxy)-7-oxo-1,6-diazabicyclo[3.2.1]octan-2-yl)(imido)methyl)sulfamoyl)acetate (2_2_1)

Methyl 2-(chlorosulfonyl)acetate (0.08 mL, 0.70 mmol) and TEA (0.21 mL, 1.5 mmol) were added to a suspension of BB-1 (137 mg, 0.50 mmol) in CH$_2$Cl$_2$ (6 mL) at 0° C. and then stirred overnight at room temperature. The reaction mixture was diluted with CH$_2$Cl$_2$ (30 mL), washed with saturated NaHCO$_3$, brine, dried over Na$_2$SO$_4$ and filtered. The organic layer was concentrated to give a residue, which was purified by silica gel column chromatography eluting with 75% ethyl acetate in petroleum ether to give the title compound 2_2_1 (107 mg, 52%) as a white foam. $^1$H NMR (400 MHz, DMSO-d$_6$): δ 1.78-1.93 (m, 3H), 2.02-2.09 (m, 1H), 3.13 (t, J=11.9 Hz, 1H), 3.65-3.71 (m, 1H), 3.72 (s, 3H), 3.90-4.00 (m, 1H), 4.51 (d, J=15.1 Hz, 1H), 4.55 (d, J=15.1 Hz, 1H), 4.83 (s, 2H), 5.14 (s, 1H), 6.75 (s, 2H), 7.33-7.43 (m, 3H), 7.47-7.53 (m, 2H). LC-MS [M+Na]$^+$ m/z 433.1 (calcd for C$_{17}$H$_{22}$N$_4$O$_6$S, 410.13).

Step 2: Synthesis of methyl 2-(N-(((2S,5R)-6-hydroxy-7-oxo-1,6-diazabicyclo[3.2.1]octan-2-yl)(imido)methyl)sulfamoyl)acetate (2_2_2)

10% Pd/C (60 mg) was added to a solution of compound 2_2_1 (103 mg, 0.251 mmol) in EtOAc (6 mL) with a few drops of TEA. The mixture was stirred under H$_2$ (balloon) at room temperature for 3 hours, filtered through a pad of celite, rinsed with EtOAc (2×5 mL). The filtrate was concentrated to give the title compound 2_2_2 (82 mg, 95%) as a white foam, which was used for the next step without further purification. $^1$H NMR (400 MHz, DMSO-d$_6$): δ 1.68-1.86 (m, 3H), 2.02-2.09 (m, 1H), 3.07 (t, J=11.9 Hz, 1H), 3.59-3.67 (m, 1H), 3.73 (s, 3H), 3.93-4.02 (m, 1H), 4.53 (d, J=15.2 Hz, m, 1H), 4.59 (d, J=15.2 Hz, m, 1H), 5.13 (s, 1H), 6.49 (s, 2H), 9.29 (s, 1H). LC-MS [M+Na]$^+$ m/z 343.1 (calcd for C$_{10}$H$_{16}$N$_4$O$_6$S, 320.08).

Step 3: Synthesis of sodium (2S,5R)-2-(N-((2-methoxy-2-oxoethyl)sulfonyl)caramimidoyl)-7-oxo-1,6-diazabicyclo[3.2.1]octan-6-yl sulfate (Example 2)

SO$_3$-pyridine (130 mg, 0.82 mmol) was added to a solution of 2_2_2 (80 mg, 0.25 mmol) in pyridine (2.5 mL).

The reaction mixture was stirred at room temperature overnight and concentrated under reduced pressure to provide a residue. The residue was purified by resin Dowex-50wx Na+ exchange, using water as elution solvent to give example 2 (86 mg, 81%) as a white solid. $^1$H NMR (400 MHz, D$_2$O) δ 1.86-2.05 (m, 3H), 2.09-2.15 (m, 1H), 3.31-3.38 (m, 1H), 3.74 (s, 3H), 3.82-3.88 (m, 1H), 3.96-4.04 (m, 1H), 4.36-4.45 (m, 2H), 5.09 (s, 1H). LC-MS [M−Na]$^-$ m/z 399.1 (calcd for C$_{10}$H$_{15}$N$_4$NaO$_9$S$_2$, 422.02).

Example 3

Sodium (2S,5R)-2-(N-((2-methoxyethyl)sulfonyl)carbamimidoyl)-7-oxo-1,6-diazabicyclo[3.2.1]octan-6-yl sulfate (Compound 21 in Table 1)

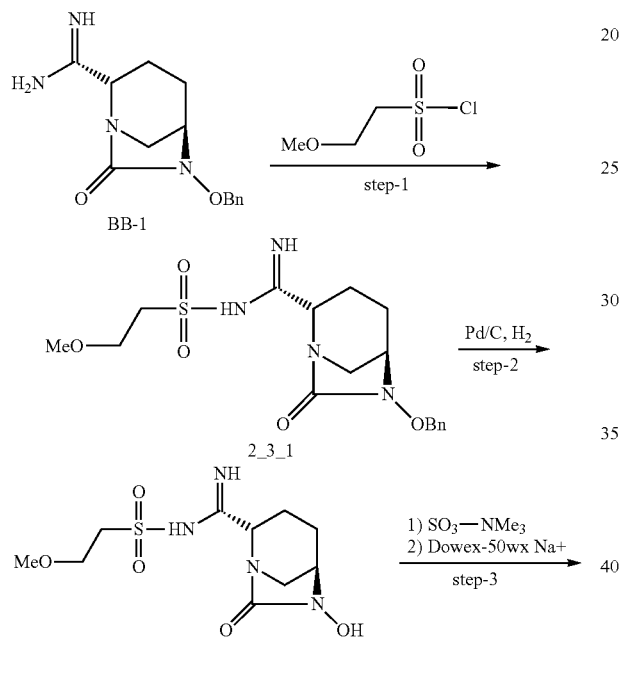

Step-1: Synthesis of (2S,5R)-6-(benzyloxy)-N-((2-methoxyethyl)sulfonyl)-7-oxo-1,6-diazabicyclo[3.2.1]octane-2-carboximidamide (2_3_1)

2-Methoxyethane-1-sulfonyl chloride (107 mg, 0.60 mmol) and TEA (0.20 mL, 1.50 mmol) were added to a solution of BB-1 (137 mg, 0.50 mmol) in DCM (8 mL) at 0° C., and then stirred overnight at room temperature. The reaction mixture was concentrated to give a residue, which was purified by silica gel column chromatography eluting with 50% ethyl acetate in hexane to give the compound 2_3_1 (158 mg, 80%) as a white solid. $^1$H NMR (400 MHz, DMSO-d$_6$): δ 1.81-1.90 (m, 3H), 1.95-2.06 (m, 1H), 3.04 (t, J=11.6 Hz, 1H), 3.26 (s, 3H), 3.43-3.50 (m, 2H), 3.57-3.66 (m, 3H), 3.90-3.99 (m, 1H), 4.83 (s, 2H), 5.05 (s, 1H), 6.74 (s, 2H), 7.38-7.41 (m, 3H), 7.47-7.51 (m, 2H). LC-MS [M+H]$^+$ m/z 397.2 (calcd for C$_{17}$H$_{24}$N$_4$O$_5$S, 396.15).

Step 2: Synthesis of (2S,5R)-6-hydroxy-N-((2-methoxyethyl)sulfonyl)-7-oxo-1,6-diazabicyclo[3.2.1]octane-2-carboximidamide (2_3_2)

10% Pd/C (wet, 55% water w/w, 80 mg) was added to a solution of compound 2_3_1 (158 mg, 0.4 mmol) in EtOAc (10 mL) with two drops of TEA. The reaction mixture was stirred under H$_2$ (balloon) at room temperature overnight, filtered through a pad of celite, rinsed with EtOAc. The filtrate was concentrated under vacuum to give the title compound 2_3_2 (158 mg, 80%) as a white solid. LC-MS [M+H]$^+$ m/z 307.1 (calcd for C$_{10}$H$_{18}$N$_4$O$_5$S, 306.10).

Step 3: Synthesis of sodium (2S,5R)-2-(N-((2-methoxyethyl)sulfonyl)carbamimidoyl)-7-oxo-1,6-diazabicyclo[3.2.1]octan-6-yl sulfate (Example 3)

A mixture of compound 2_3_2 (158 mg, 0.40 mmol), SO$_3$-pyridine (210 mg, 1.32 mmol) in pyridine (2.5 mL) was stirred at room temperature overnight. The reaction mixture was concentrated to give a residue, which was purified by preparative HPLC on an Agilent 10 prep-C18 250×21.2 mm column and lyophilized, followed by resin Dowex-50wx Na+ exchange using water as elution solvent to give example 3 (5 mg, 2%) as a white solid. $^1$H NMR (400 MHz, D$_2$O): δ 1.89-2.05 (m, 3H), 2.10-2.16 (m, 1H), 3.26-3.34 (m, 4H), 3.47-3.53 (s, 2H), 3.77-3.83 (m, 3H), 3.98-4.07 (m, 1H), 5.03 (s, 1H). LC-MS [M−Na]$^-$ m/z 385.1 (calcd for C$_{10}$H$_{17}$N$_4$NaO$_8$S, 408.04).

Example 4

Sodium (2S,5R)-2-(N-((3-methoxy-3-oxopropyl)sulfonyl)carbamimidoyl)-7-oxo-1,6-diazabicyclo[3.2.1]octan-6-ylsulfate (Compound 20 in Table 1)

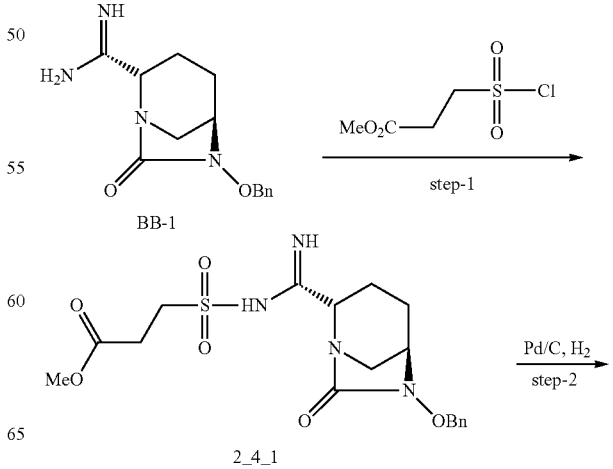

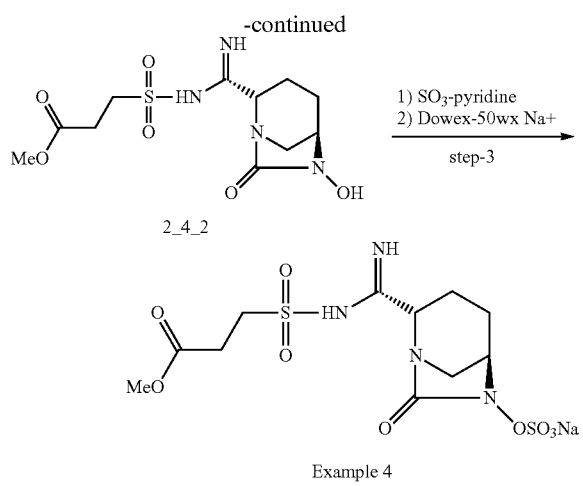

Example 4

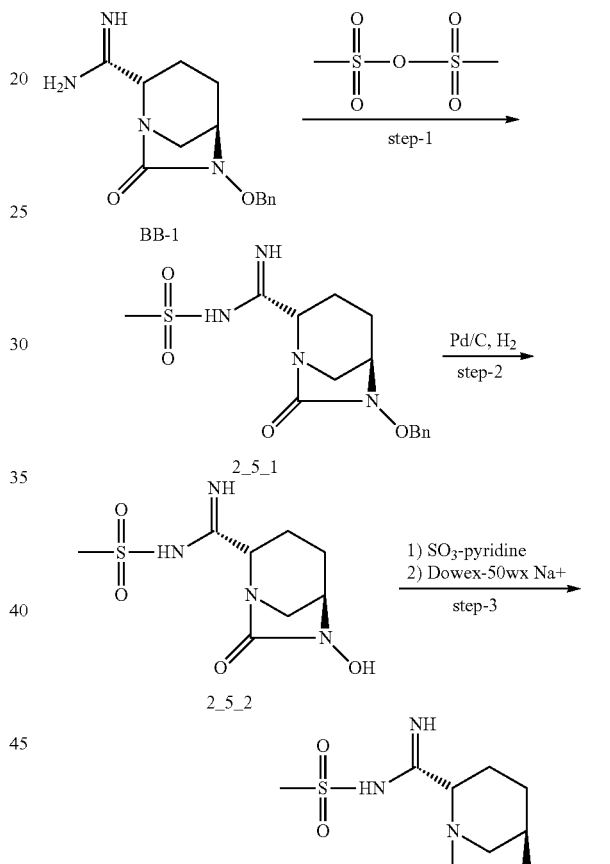

column and lyophilized, followed by resin Dowex-50wx Na+ exchange using water as elution solvent to give example 4 (5 mg, 2%) as a white solid. $^1$H NMR (400 MHz, D$_2$O): δ 1.83-2.05 (m, 3H), 2.08-2.14 (m, 1H), 2.63 (t, J=7.1 Hz, 1H), 2.79 (t, J=7.1 Hz, 1H), 3.23-3.35 (m, 1H), 3.44-3.51 (s, 1H), 3.53-3.58 (m, 1H), 3.64 (s, 3H), 3.73-3.79 (m, 1H), 3.96-4.04 (m, 1H), 5.00 (s, 1H). LC-MS [M−Na]$^-$ m/z 413.1 (calcd for C$_{11}$H$_{17}$N$_4$NaO$_9$S$_2$, 436.03).

Example 5

Sodium (2S,5R)-2-(N-(methylsulfonyl)carbamimidoyl)-7-oxo-1,6-diazabicyclo[3.2.1]octan-6-yl sulfate (Compound 1 in Table 1)

Step-1: Synthesis of methyl 3-(N-(((2S,5R)-6-(benzyloxy)-7-oxo-1,6-diazabicyclo[3.2.1]octan-2-yl)(imino)methyl)sulfamoyl)propanoate (2_4_1)

Methyl 3-(chlorosulfonyl)propanoate (112 mg, 0.6 mmol) and TEA (0.2 mL, 1.5 mmol) were added to a solution of BB-1 (137 mg, 0.5 mmol) in EtOAc (8 mL) at 0° C., and then stirred overnight at room temperature. The reaction mixture was concentrated to give a residue, which was purified by silica gel column chromatography eluting with 50% ethyl acetate in hexane to give the compound 2_4_1 (211 mg, quantitative) as a white solid. $^1$H NMR (400 MHz, DMSO-d$_6$): δ 1.81-1.89 (m, 3H), 2.02-2.06 (m, 1H), 2.72 (t, J=7.2 Hz, 2H), 3.02 (t, J=11.7 Hz, 1H), 3.42-3.53 (m, 2H), 3.54-3.59 (m, 1H), 3.64 (s, 3H), 3.90-3.99 (m, 1H), 4.83 (s, 2H), 5.07 (s, 1H), 6.76 (s, 2H), 7.35-7.41 (m, 3H), 7.48-7.51 (m, 2H). LC-MS [M+H]$^+$ m/z 425.1 (calcd for C$_{18}$H$_{24}$N$_4$O$_6$S, 424.14).

Step 2: Synthesis of methyl 3-(N-(((2S,5R)-6-hydroxy-7-oxo-1,6-diazabicyclo[3.2.1]octan-2-yl)(imino)methyl)sulfamoyl)propanoate (2_4_2)

10% Pd/C (wet, 55% water w/w, 75 mg) was added to a solution of compound 2_4_1 (210 mg, 0.5 mmol) in EtOAc (10 mL) with a few drops of TEA. The reaction mixture was stirred under H$_2$ (balloon) at room temperature for 12 hours, filtered through a pad of celite, rinsed with EtOAc. The filtrate was concentrated in vacuum to give the title compound 2_4_2 (167 mg, quantitative) as a white solid. $^1$H NMR (400 MHz, DMSO-d$_6$): δ 1.67-1.89 (m, 3H), 2.01-2.06 (m, 1H), 2.73 (t, J=7.3 Hz, 2H), 3.01 (t, J=11.6 Hz, 1H), 3.46-3.55 (m, 3H), 3.64 (s, 3H), 3.96-4.02 (m, 1H), 5.06 (s, 1H), 6.48 (s, 2H), 9.30 (s, 1H). LC-MS [M+Na]$^+$ m/z 357.1 (calcd for C$_{11}$H$_{18}$N$_4$O$_6$S, 334.09).

Step 3: Synthesis of sodium (2S,5R)-2-(N-((3-methoxy-3-oxopropyl)sulfonyl)carbamimidoyl)-7-oxo-1,6-diazabicyclo[3.2.1]octan-6-yl sulfate (Example 4)

A mixture of compound 2_4_2 (166 mg, 0.5 mmol), SO$_3$-pyridine (262 mg, 1.65 mmol) in pyridine (2.5 mL) was stirred at room temperature overnight. The reaction mixture was concentrated to give a residue, which was purified by preparative HPLC on an Agilent 10 prep-C18 250×21.2 mm Step-1: Synthesis of (2S,5R)-6-(benzyloxy)-N-(methylsulfonyl)-7-oxo-1,6-diazabicyclo[3.2.1]octane-2-carboximidamide (2_5_1)

Methanesulfonic anhydride (122 mg, 0.70 mmol) and TEA (15 mg, 1.50 mmol) were added to a solution of BB-1 (137 mg, 0.50 mmol) in DCM (6 mL) at 0° C., and then stirred overnight at room temperature. The reaction mixture was concentrated to give a residue, which was purified by silica gel column chromatography eluting with 50% ethyl acetate in hexane to give the compound 2_5_1 (110 mg, 62.5%) as a white solid. $^1$H NMR (400 MHz, DMSO-d$_6$): δ

1.81-1.91 (m, 3H), 2.01-2.09 (m, 1H), 2.93 (t, J=11.4 Hz, 1H), 3.03 (s, 3H), 3.52-3.57 (m, 1H), 3.94-4.01 (m, 1H), 4.79-4.87 (m, 2H), 5.04 (s, 1H), 6.75 (s, 2H), 7.36-7.40 (m, 3H), 7.48-7.51 (m, 2H). LC-MS [M+H]$^+$ m/z 353.1 (calcd for $C_{15}H_{20}N_4O_4S$ 352.12).

Step 2: Synthesis of (2S,5R)-6-hydroxy-N-(methylsulfonyl)-7-oxo-1,6-diazabicyclo[3.2.1]octane-2-carboximidamide (2_5_2)

10% Pd/C (wet, 55% water w/w, 55 mg) was added to a solution of compound 2_5_1 (110 mg, 0.31 mmol) in EtOAc (10 mL) with a few drops of TEA. The reaction mixture was stirred under H$_2$ (balloon) at room temperature overnight, filtered through a pad of celite, rinsed with EtOAc. The filtrate was concentrated under vacuum to give the title compound 2_5_2 (73 mg, 90%) as a white solid. $^1$H NMR (400 MHz, DMSO-d$_6$): δ 1.70-1.88 (m, 3H), 2.03-2.09 (m, 1H), 2.96 (t, J=11.4 Hz, 1H), 3.05 (s, 3H), 3.49-3.55 (m, 1H), 3.96-4.05 (m, 1H), 5.04 (s, 1H), 6.48 (s, 2H), 9.31 (br s, 1H). LC-MS [M+Na]$^+$ m/z 285.0 (calcd for $C_8H_{14}N_4O_4S$ 262.07).

Step 3: Synthesis of sodium (2S,5R)-2-(N-(methylsulfonyl)carbamimidoyl)-7-oxo-1,6-diazabicyclo[3.2.1]octan-6-yl sulfate (Example 5)

A mixture of compound 2_5_2 (120 mg, 0.31 mmol), SO$_3$-pyridine (143 mg, 0.90 mmol) in pyridine (3 mL) was stirred at room temperature overnight. The reaction mixture was concentrated to give a residue, which was purified by resin Dowex-50wx Na$^+$ exchange using water as elution solvent to give example 5 (80 mg, 71%) as a white solid. $^1$H NMR (400 MHz, D$_2$O): δ 1.91-2.06 (m, 3H), 2.12-2.18 (m, 1H), 3.08 (s, 3H), 3.26 (t, J=11.6 Hz, 1H), 3.78-3.84 (m, 1H), 4.03-4.12 (m, 1H), 5.03 (s, 1H). LC-MS [M−Na]$^−$ m/z 341.0 (calcd for $C_8H_{13}N_4NaO_7S_2$, 364.01).

Example 6

Sodium (2S,5R)-2-(N-(cyclopropylsulfonyl)carbamimidoyl)-7-oxo-1,6-diazabicyclo[3.2.1]octan-6-yl sulfate (Compound 25 in Table 1)

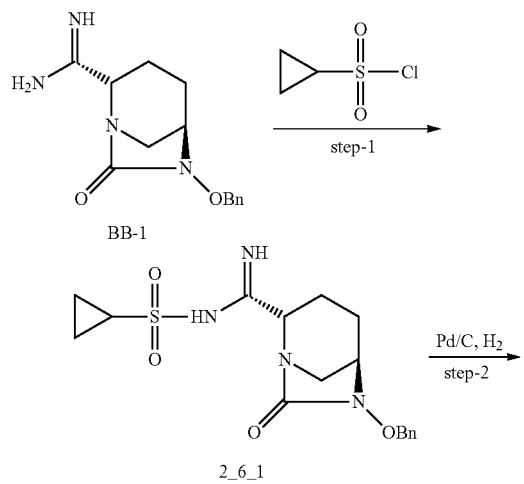

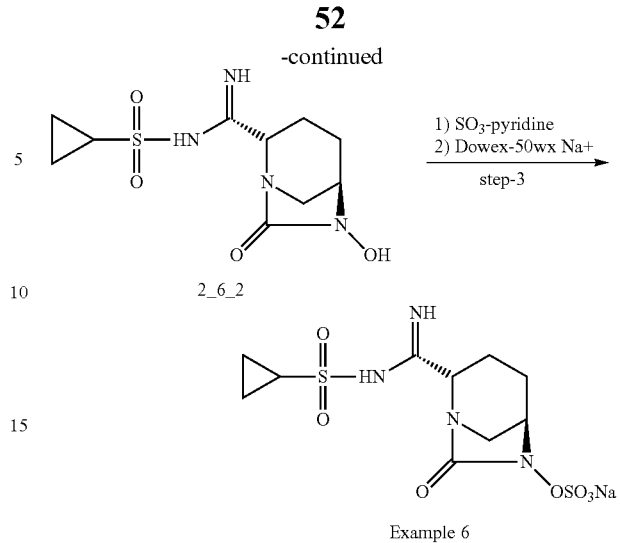

Example 6

Step-1: Synthesis of (2S,5R)-6-(benzyloxy)-N-(cyclopropylsulfonyl)-7-oxo-1,6-diazabicyclo[3.2.1]octane-2-carboximidamide (2_6_1)

Cyclopropanesulfonyl chloride (71 mg, 0.5 mmol) and TEA (0.2 mL, 1.5 mmol) were added to a solution of BB-1 (137 mg, 0.5 mmol) in DCM (8 mL) at 0° C., and then stirred overnight at room temperature. The reaction mixture was concentrated to give a residue, which was purified by silica gel column chromatography eluting with 50% ethyl acetate in hexane to give the title compound 2_6_1 (83 mg, 41.5%) as a white solid. $^1$H NMR (400 MHz, DMSO-d$_6$): δ 0.98-1.07 (m, 4H), 1.83-1.91 (m, 3H), 2.01-2.07 (m, 1H), 2.66-2.70 (m, 1H), 3.06 (t, J=11.6 Hz, 1H), 3.56-3.61 (m, 1H), 3.93-4.00 (m, 1H), 4.83 (s, 2H), 5.05 (s, 1H), 6.76 (br s, 2H), 7.35-7.42 (m, 3H), 7.47-7.52 (m, 2H). LC-MS [M+Na]$^+$ m/z 401.1 (calcd for $C_{17}H_{22}N_4O_4S$, 378.14).

Step 2: Synthesis of (2S,5R)—N-(cyclopropylsulfonyl)-6-hydroxy-7-oxo-1,6-diazabicyclo[3.2.1]octane-2-carboximidamide (2_6_2)

10% Pd/C (dry, 80 mg) was added to a solution of compound 2_6_1 (106 mg, 0.28 mmol) in EtOAc (10 mL) with a few drops of TEA. The reaction mixture was stirred under H$_2$ (balloon) at room temperature for 12 hours, filtered through a pad of celite, rinsed with EtOAc. The filtrate was concentrated under vacuum to give the title compound 2_6_2 (83 mg, quantitative) as a white solid. $^1$H NMR (400 MHz, DMSO-d$_6$): δ 0.97-1.01 (m, 4H), 1.79-1.91 (m, 3H), 2.02-2.08 (m, 1H), 2.65-2.72 (m, 1H), 3.07 (t, J=11.4 Hz, 1H), 3.51-3.57 (m, 1H), 3.98-4.06 (m, 1H), 5.06 (s, 1H), 6.50 (s, 2H), 9.32 (s, 1H). LC-MS M+Na]$^+$ m/z 311.1 ($C_{10}H_{16}N_4O_4S$, 288.09).

Step 3: Synthesis of Sodium (2S,5R)-2-(N-(cyclopropylsulfonyl)carbamimidoyl)-7-oxo-1,6-diazabicyclo[3.2.1]octan-6-yl sulfate (Example 6)

A mixture of compound 2_6_2 (83 mg, 0.28 mmol), SO$_3$-pyridine (147 mg, 0.92 mmol) in pyridine (2.5 mL) was stirred at room temperature overnight. The reaction mixture was concentrated to give a residue, which was purified by preparative HPLC on an Agilent 10 prep-C18 250×21.2 mm column and lyophilized, followed by resin Dowex-50wx Na⁺ exchange using water as elution solvent to give example 6 (48 mg, 46.6%) as a white solid. ¹H NMR (400 MHz, D₂O): δ 0.99-1.07 (m, 3H), 1.10-1.14 (m, 1H), 1.81-1.97 (m, 3H), 2.00-2.08 (m, 1H), 2.54-2.59 (m, 1H), 3.27 (t, J=11.7 Hz, 1H), 3.71-3.76 (m, 1H), 3.90-3.99 (m, 1H), 4.92 (s, 1H). LC-MS [M−Na]⁻ m/z 367.0 (calcd for $C_{10}H_{15}N_4NaO_7S_2$, 390.03).

Example 7

Sodium (2S,5R)-2-(N-((1-methyl-1H-imidazol-4-yl)sulfonyl)carbamimidoyl)-7-oxo-1,6-diazabicyclo[3.2.1]octan-6-yl sulfate (Compound 42 in Table 1)

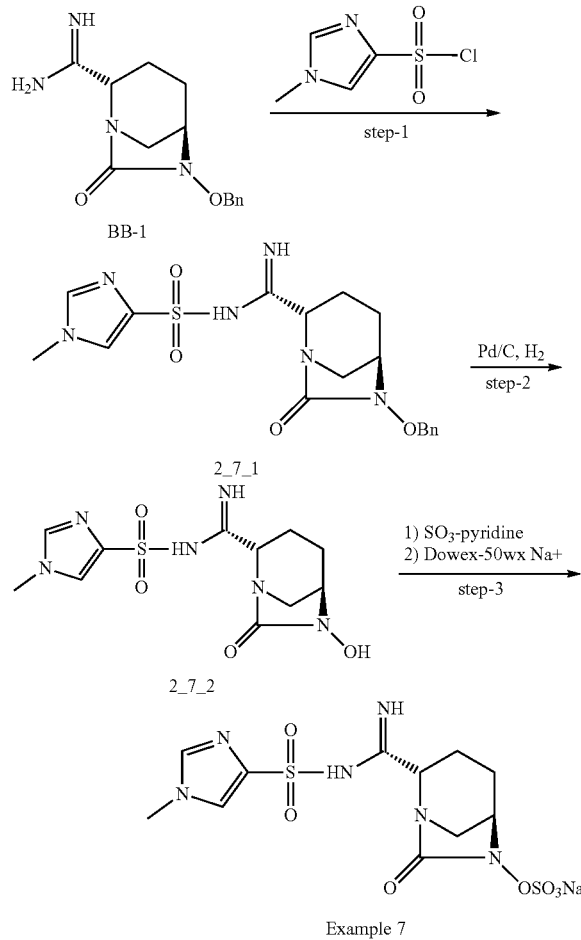

Step-1: Synthesis of (2S,5R)-6-(benzyloxy)-N-((1-methyl-1H-imidazol-4-yl)sulfonyl)-7-oxo-1,6-diazabicyclo[3.2.1]octane-2-carboximidamide (2_7_1)

1-Methyl-1H-imidazole-4-sulfonyl chloride (108 mg, 0.60 mmol) and TEA (0.2 mL, 1.50 mmol) were added to a solution of BB-1 (137 mg, 0.5 mmol) in DCM (8 mL) at 0° C., and then stirred overnight at room temperature. The reaction mixture was concentrated to give a residue, which was purified by silica gel column chromatography eluting with 50% ethyl acetate in hexane to give the title compound 2_7_1 (168 mg, 80.4%) as a white solid. ¹H NMR (400 MHz, DMSO-d₆): δ 1.75-1.93 (m, 3H), 1.96-2.04 (m, 1H), 2.96 (t, J=11.5 Hz, 1H), 3.66-3.71 (s, 4H), 3.88-3.97 (m, 1H), 4.74-4.82 (m, 2H), 4.95 (s, 1H), 6.73 (s, 2H), 7.33-7.38 (m, 3H), 7.43-7.48 (m, 2H), 7.86 (s, 1H), 7.94 (s, 1H). LC-MS [M+H]⁺ m/z 419.2 (calcd for $C_{18}H_{22}N_6O_4S$, 418.14).

Step 2: Synthesis of (2S,5R)-6-hydroxy-N-((1-methyl-1H-imidazol-4-yl)sulfonyl)-7-oxo-1,6-diazabicyclo[3.2.1]octane-2-carboximidamide (2_7_2)

10% Pd/C (dry, 60 mg) was added to a solution of compound 2_7_1 (168 mg, 0.4 mmol) in THF (3 mL) and EtOAc (7 mL). The reaction mixture was stirred under H₂ (balloon) at room temperature for 12 hours. It was filtered through a pad of celite, rinsed with EtOAc. The filtrate was concentrated under vacuum to give the title compound 2_7_2 (141 mg, quantitative) as a white solid, which was directly used for next step without further purification. ¹H NMR (400 MHz, DMSO-d₆): δ 1.62-1.96 (m, 3H), 1.96-2.03 (m, 1H), 2.91 (t, J=11.5 Hz, 1H), 3.60-3.65 (m, 1H), 3.71 (s, 3H), 3.89-3.99 (m, 1H), 4.94 (s, 1H), 6.47 (s, 2H), 7.87 (s, 1H), 7.94 (s, 1H), 9.25 (s, 1H). LC-MS [M+Na]⁺ m/z 351.1 (calcd for $C_{11}H_{16}N_6O_4S$, 328.10).

Step 3: Synthesis of sodium (2S,5R)-2-(N-((1-methyl-1H-imidazol-4-yl)sulfonyl)carbamimidoyl)-7-oxo-1,6-diazabicyclo[3.2.1]octan-6-yl sulfate (Example 7)

A mixture of compound 2_7_2 (140 mg, 0.4 mmol), SO₃-pyridine (224 mg, 1.4 mmol) in pyridine (2.5 mL) was stirred at room temperature overnight. The reaction mixture was concentrated to give a residue, which was purified by preparative HPLC on an Agilent 10 prep-C18 250×21.2 mm column and lyophilized, followed by resin Dowex-50wx Na⁺ exchange using water as elution solvent to give example 7 (105 mg, 64%) as a white solid. ¹H NMR (400 MHz, D₂O): δ 1.75-1.82 (m, 3H), 1.91-1.97 (m, 1H), 2.90 (t, J=11.1 Hz, 1H), 3.57 (s, 3H), 3.72 (d, J=11.7 Hz, 1H), 3.83-3.92 (m, 1H), 4.85 (s, 1H), 7.60 (s, 1H), 7.71 (s, 1H). LC-MS [M−Na]⁻ m/z 407.1 (calcd for $C_{11}H_{15}N_6NaO_7S_2$, 430.03).

Example 8

Sodium (2S,5R)-2-(N-(ethylsulfonyl)carbamimidoyl)-7-oxo-1,6-diazabicyclo[3.2.1]octan-6-yl sulfate (Compound 4 in Table 1)

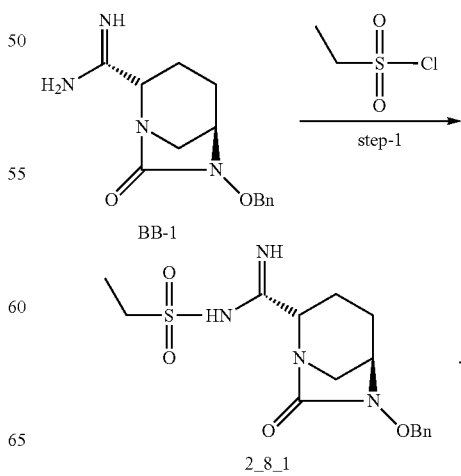

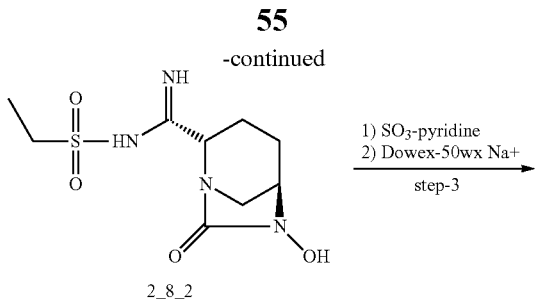

2_8_2

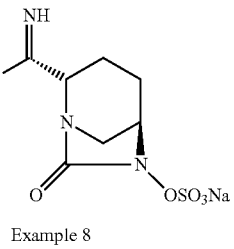

Example 8

Step-1: Synthesis of (2S,5R)-6-(benzyloxy)-N-(ethylsulfonyl)-7-oxo-1,6-diazabicyclo[3.2.1]octane-2-carboximidamide (2_8_1)

Ethanesulfonyl chloride (77 mg, 0.6 mmol) and TEA (0.2 mL, 1.5 mmol) were added to a solution of BB-1 (137 mg, 0.5 mmol) in DCM (8 mL) at 0° C., and then stirred overnight at room temperature. The reaction mixture was concentrated to give a residue, which was purified by silica gel column chromatography eluting with 50% ethyl acetate in hexane to give the title compound 2_8_1 (170 mg, 93%) as a white solid. $^1$H NMR (400 MHz, DMSO-$d_6$): δ 1.14-1.26 (m, 3H), 1.78-1.90 (m, 3H), 1.95-2.08 (m, 1H), 2.98 (t, J=11.4 Hz, 1H), 3.08-3.17 (m, 1H), 3.18-3.28 (m, 1H), 3.53-3.57 (m, 1H), 3.93 (s, 1H), 4.81 (s, 2H), 5.05 (s, 1H), 6.81 (br s, 2H), 7.34-7.40 (m, 3H), 7.46-7.51 (m, 2H). LC-MS [M+Na]$^+$ m/z 389.1 (calcd for $C_{16}H_{22}N_4O_4S$, 366.14).

Step 2: Synthesis of (2S,5R)—N-(ethylsulfonyl)-6-hydroxy-7-oxo-1,6-diazabicyclo[3.2.1]octane-2-carboximidamide (2_8_2)

10% Pd/C (dry, 80 mg) was added to a solution of compound 2_8_1 (170 mg, 0.46 mmol) in EtOAc (10 mL) with two drops of TEA. The reaction mixture was stirred under H$_2$ (balloon) at room temperature for 4 hours, filtered through a pad of celite, rinsed with EtOAc. The filtrate was concentrated under vacuum to give the title compound 2_8_2 (106 mg, 83.5%) as a white solid. $^1$H NMR (400 MHz, DMSO-$d_6$): δ 1.21 (t, J=7.3 Hz, 3H), 1.76-1.89 (m, 3H), 1.98-2.07 (m, 1H), 3.02 (t, J=11.5 Hz, 1H), 3.14-3.29 (m, 2H), 3.52-3.57 (m, 1H), 3.93-4.02 (m, 1H), 5.05 (s, 1H), 6.46 (s, 2H), 9.30 (s, 1H). LC-MS [M+Na]$^+$ m/z 299.1 (calcd for $C_9H_{16}N_4O_4S$, 276.09).

Step 3: Synthesis of sodium (2S,5R)-2-(N-(ethylsulfonyl)carbamimidoyl)-7-oxo-1,6-diazabicyclo[3.2.1]octan-6-ylsulfate (Example 8)

A mixture of compound 2_8_2 (106 mg, 0.38 mmol), SO$_3$-pyridine (202 mg, 1.27 mmol) in pyridine (2.5 mL) was stirred at room temperature overnight. The reaction mixture was concentrated to give a residue, which was purified by preparative HPLC on an Agilent 10 prep-C18 250×21.2 mm column and lyophilized, followed by resin Dowex-50wx Na$^+$ exchange using water as elution solvent to give example 8 (131 mg, 98%) as a white solid. $^1$H NMR (400 MHz, D$_2$O): δ 1.13 (t, J=7.4 Hz, 3H), 1.77-1.91 (m, 3H), 1.97-2.03 (m, 1H), 3.11 (q, J=7.4 Hz, 2H), 3.20 (t, J=11.7 Hz, 1H), 3.64-3.72 (m, 1H), 3.86-3.94 (m, 1H), 4.91 (s, 1H). LC-MS [M–Na]$^-$ m/z 355.1 (calcd for $C_9H_{15}N_4NaO_7S_2$, 378.03).

Example 9

Sodium (2S,5R)-7-oxo-2-(N-tosylcarbamimidoyl)-1,6-diazabicyclo[3.2.1]octan-6-yl sulfate (Compound 38 in Table 1)

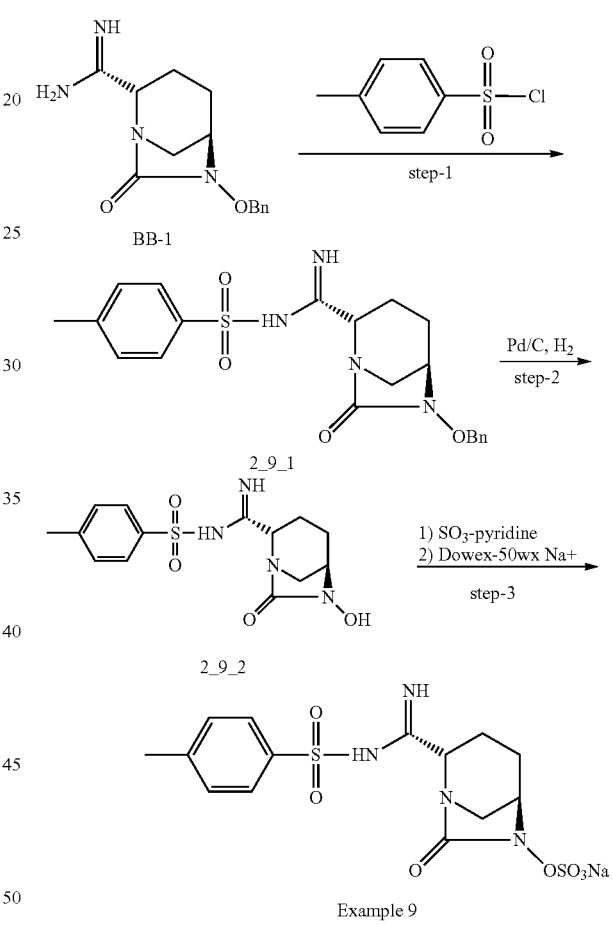

Example 9

Step-1: Synthesis of (2S,5R)-6-(benzyloxy)-7-oxo-N-tosyl-1,6-diazabicyclo[3.2.1]octane-2-carboximidamide (2_9_1)

4-Methylbenzenesulfonyl chloride (137 mg, 0.5 mmol) and TEA (0.2 mL, 1.5 mmol) were added to a solution of BB-1 (114 mg, 0.6 mmol) in DCM (3 mL) at 0° C., and then stirred overnight at room temperature. The reaction mixture was concentrated to give a residue, which was purified by silica gel column chromatography eluting with 50% ethyl acetate in hexane to give the title compound 2_9_1 (196 mg, 91%) as a white solid. $^1$H NMR (400 MHz, DMSO-$d_6$): δ 1.70-1.80 (m, 3H), 1.90-1.90 (m, 1H), 2.34 (s, 3H), 2.58 (t, J=11.2 Hz, 1H), 3.55-3.61 (m, 1H), 3.85-3.93 (m, 1H), 4.70

(s, 2H), 5.04 (s, 1H), 6.67 (br s, 2H), 7.23-7.28 (m, 3H), 7.30-7.34 (m, 2H), 7.39 (d, J=8.1 Hz, 2H), 7.62 (d, J=8.1 Hz, 2H). LC-MS [M+Na]$^+$ m/z 451.2 (calcd for $C_{21}H_{24}N_4O_4S$, 428.15).

Step 2: Synthesis of (2S,5R)-6-hydroxy-7-oxo-N-tosyl-1,6-diazabicyclo[3.2.1]octane-2-carboximidamide (2_9_2)

10% Pd/C (dry, 80 mg) was added to a solution of compound 2_9_1 (196 mg, 0.45 mmol) in EtOAc (10 mL) with two drops of TEA. The reaction mixture was stirred under $H_2$ (balloon) at room temperature for 3 hours, filtered through a pad of celite, rinsed with EtOAc. The filtrate was concentrated under vacuum to give the title compound 2_9_2 (130 mg, 84%) as a white solid. $^1$H NMR (400 MHz, DMSO-$d_6$): δ 1.56-1.70 (m, 2H), 1.74-1.84 (m, 1H), 1.90-1.97 (m, 1H), 2.60 (t, J=11.3 Hz, 1H), 3.49-3.55 (m, 1H), 3.89-3.98 (m, 1H), 5.05 (s, 1H), 6.41 (s, 2H), 7.41 (d, J=8.1 Hz, 2H), 7.63 (d, J=8.1 Hz, 2H), 9.17 (s, 1H). LC-MS [M+Na]$^+$ m/z 361.1 (calcd for $C_{14}H_{18}N_4O_4S$, 338.10).

Step 3: Synthesis of Sodium (2S,5R)-7-oxo-2-(N-tosylcarbamimidoyl)-1,6-diazabicyclo[3.2.1]octan-6-yl sulfate (Example 9)

A mixture of compound 2_9_2 (130 mg, 0.38 mmol), $SO_3$-pyridine (202 mg, 1.27 mmol) in pyridine (2.5 mL) was stirred at room temperature overnight. The reaction mixture was concentrated to give a residue, which was purified by preparative HPLC on an Agilent 10 prep-C18 250×21.2 mm column and lyophilized, followed by resin Dowex-50wx Na$^+$ exchange using water as elution solvent to give example 9 (55 mg, 38%) as a white solid. $^1$H NMR (400 MHz, $D_2O$): δ 1.76-1.89 (m, 3H), 1.96-2.02 (m, 1H), 2.87 (t, J=11.5 Hz, 1H), 3.81-3.86 (m, 1H), 3.95-4.03 (m, 1H), 4.94-4.98 (m, 1H), 7.36 (d, J=8.2 Hz, 2H), 7.63 (d, J=8.2 Hz, 2H). LC-MS [M−Na]$^-$ m/z 417.1 (calcd for $C_{14}H_{17}N_4NaO_7S_2$, 440.04).

Example 10

(2S,5R)-2-(N-((2,5-dichlorothiophen-3-yl)sulfonyl) carbamimidoyl)-7-oxo-1,6-diazabicyclo[3.2.1]octan-6-yl hydrogen sulfate (Compound 73 in Table 1)

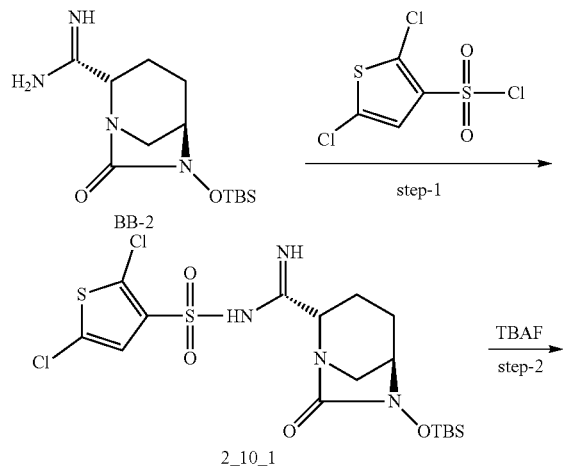

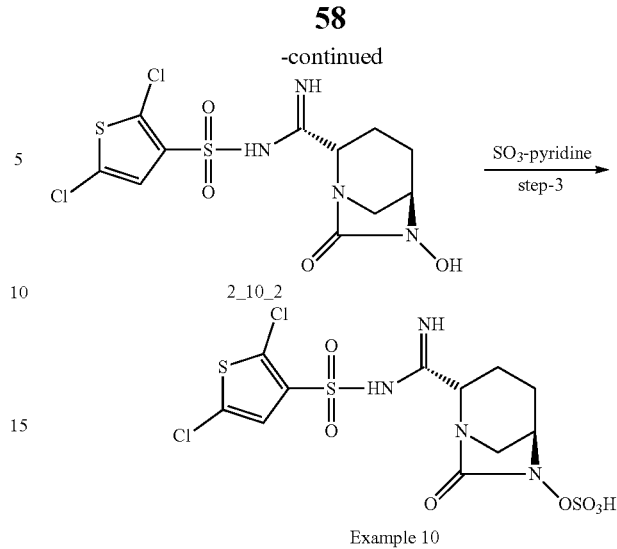

Example 10

Step-1: Synthesis of (2S,5R)-6-((tert-butyldimethylsilyl)oxy)-N-((2,5-dichlorothiophen-3yl)sulfonyl)-7-oxo-1,6-diazabicyclo[3.2.1]octane-2-carboximidamide (2_10_1)

2,5-Dichlorothiophene-3-sulfonyl chloride (298 mg, 1.2 mmol) and TEA (0.22 mL, 1.8 mmol) were added to a solution of BB-2 (164 mg, 0.6 mmol) in DCM (5 mL) at 0° C., and then stirred overnight at room temperature. The reaction mixture was concentrated to give a residue, which was purified by silica gel column chromatography eluting with 50% ethyl acetate in petroleum ether to give the title compound 2_10_1 (250 mg, 81.3%) as a orange gum. $^1$H NMR (400 MHz, DMSO-$d_6$): δ 0.00 (s, 6H), 0.76 (s, 9H), 1.65-1.77 (m, 3H), 1.89-1.94 (m, 1H), 2.93 (t, J=11.6 Hz, 1H), 3.47-3.55 (m, 1H), 3.61-3.68 (m, 1H), 5.01 (s, 1H), 6.49 (br s, 2H), 7.34 (m, 1H). LC-MS [M+Na]$^+$ m/z 535.1, 537.1, 539.1 (calcd for $C_{17}H_{26}Cl_2N_4O_4S_2Si$, 512.05).

Step 2: Synthesis of (2S,5R)—N-((2,5-dichlorothiophen-3-yl)sulfonyl)-6-hydroxy-7-oxo-1,6-diazabicyclo[3.2.1]octane-2-carboximidamide (2_10_2)

TBAF (1 M in THF, 0.73 mL, 0.73 mmol) was added to a solution of compound 2_10_1 (250 mg, 0.49 mmol) in THF (3 mL) at 0° C. and stirred for 1 hour. The reaction mixture was concentrated to give a residue, which was diluted with EtOAc, washed with brine. The organic layer was dried over $Na_2SO_4$, filtered. The filtrate was concentrated to give the title compound 2_10_2 (200 mg, quantitative) as a brown oil, which was directly used for next step without further purification. $^1$H NMR (400 MHz, DMSO-$d_6$): δ 1.71-1.89 (m, 3H), 2.08-2.14 (m, 1H), 2.94 (t, J=11.6 Hz, 1H), 3.73-3.78 (m, 1H), 4.04-4.10 (m, 1H), 5.19 (s, 1H), 6.54 (br s, 2H), 7.55 (m, 1H), 9.34 (s, 1H). LC-MS [M+Na]$^+$ m/z 420.9, 423.0, 424.9 (calcd for $C_{11}H_{12}Cl_2N_4O_4S_2$, 397.97).

Step 3: Synthesis of (2S,5R)-2-(N-((2,5-dichlorothiophen-3-yl)sulfonyl)carbamimidoyl)-7-oxo-1,6-diazabicyclo[3.2.1]octan-6-yl hydrogen sulfate (Example 10)

A mixture of compound 2_10_2 (200 mg, obtained above), $SO_3$-pyridine (500 mg, 3.14 mmol) in pyridine (5 mL) was stirred at room temperature for 5 hours. The reaction mixture was concentrated to give a residue, which was purified by preparative HPLC on an Agilent 10 prep-C18 250×21.2 mm column and lyophilized give example 10 (15.5 mg, 6.6% in two steps) as a white solid. $^1$H NMR (400 MHz, D$_2$O): δ 1.87-1.97 (m, 3H), 2.06-2.16 (m, 1H), 3.18 (t, J=11.4 Hz, 1H), 3.92-3.98 (m, 1H), 3.99-4.08 (m, 1H), 5.06 (s, 1H), 7.21 (s, 1H). LC-MS [M–H]$^-$ m/z 476.9, 478.9, 480.9 (calcd for $C_{11}H_{12}Cl_2N_4O_7S_3$, 477.92).

Example 11

(2S,5R)-7-Oxo-2-(N-((4-(trifluoromethyl)phenyl) sulfonyl)carbamimidoyl)-1,6-diazabicyclo[3.2.1] octan-6-yl hydrogen sulfate (Compound 54 in Table 1)

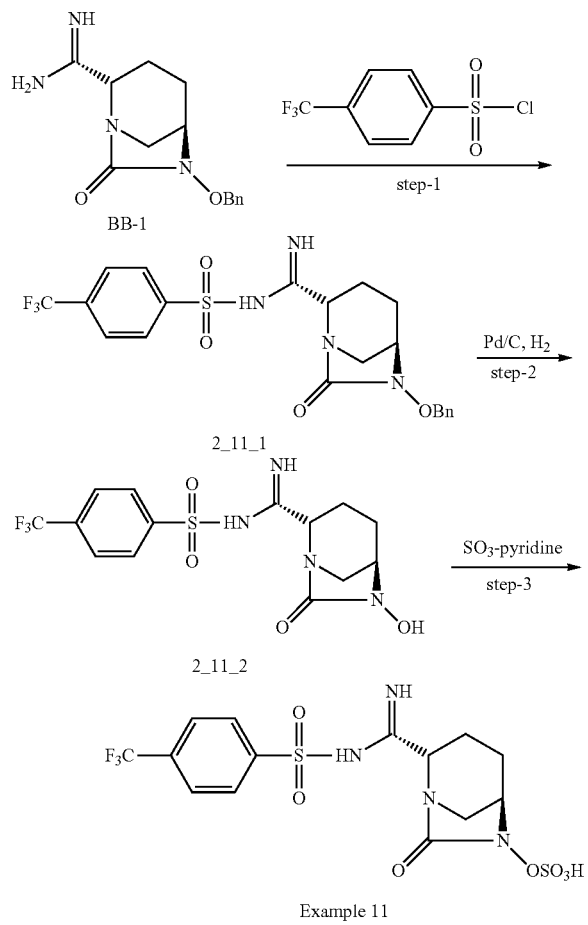

Example 11

Step-1: Synthesis of (2S,5R)-6-(benzyloxy)-7-oxo-N-((4-(trifluoromethyl)phenyl)sulfonyl)-1,6-diazabicyclo[3.2.1]octane-2-carboximidamide (2_11_1)

4-(Trifluoromethyl)benzenesulfonyl chloride (293 mg, 1.2 mmol) was added to a solution of BB-1 (164 mg, 0.6 mmol) and TEA (0.22 mL, 1.8 mmol) in CH$_2$Cl$_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_11_1 (250 mg, 86.4%) as a white solid. $^1$H NMR (400 MHz, DMSO-d$_6$): δ 1.71-1.94 (m, 3H), 1.98-2.04 (m, 1H), 2.67 (t, J=11.4 Hz, 1H), 3.71-3.77 (m, 1H), 3.95-4.02 (m, 1H), 4.78 (s, 2H), 5.20 (s, 1H), 6.78 (br s, 2H), 7.29-7.33 (m, 3H), 7.37-7.41 (m, 2H), 8.06 (s, 4H). LC-MS [M+Na]$^+$ m/z 505.1 (calcd for $C_{21}H_{21}F_3N_4O_4S$, 482.12).

Step 2: Synthesis of (2S,5R)-6-hydroxy-7-oxo-N-((4-(trifluoromethyl)phenyl)sulfonyl)-1,6-diazabicyclo[3.2.1]octane-2-carboximidamide (2_11_2)

10% Pd/C (wet, 80 mg) was added to a solution of compound 2_11_1 (250 mg, 0.52 mmol) in THF (5 mL) with a few drops of TEA. The reaction mixture was stirred under H$_2$ (balloon) at room temperature for 8 hours, filtered through a pad of celite, rinsed with EtOAc. The filtrate was concentrated under vacuum to give the title compound 2_11_2 (200 mg, 98.1%) as a white solid. $^1$H NMR (400 MHz, DMSO-d$_6$): δ 1.67-1.76 (m, 2H), 1.86-1.95 (m, 1H), 1.98-2.06 (m, 1H), 2.71 (t, J=11.4 Hz, 1H), 3.63-3.70 (m, 1H), 3.98-4.07 (m, 1H), 5.22 (s, 1H), 6.49 (s, 2H), 8.03-8.11 (m, 4H), 9.25 (s, 4H). LC-MS [M+Na]$^+$ m/z 415.1 (calcd for $C_{14}H_{15}Fe_3N_4O_4S$, 392.08).

Step 3: Synthesis of (2S,5R)-7-oxo-2-(N-((4-(trifluoromethyl)phenyl)sulfonyl)carbamimidoyl)-1,6-diazabicyclo[3.2.1]octan-6-yl hydrogen sulfate (Example 11)

A mixture of compound 2_11_2 (200 mg, 0.51 mmol), SO$_3$-pyridine (120 mg, 0.76 mmol) in pyridine (3 mL) was stirred at room temperature overnight. The reaction mixture was concentrated to give a residue, which was purified by preparative HPLC on an Agilent 10 prep-C18 250×21.2 mm column and lyophilized to give example 11 (23 mg, 9.6%) as a white solid. $^1$H NMR (400 MHz, D$_2$O): δ 1.82-1.95 (m, 3H), 2.02-2.08 (m, 1H), 2.96 (t, J=11.5 Hz, 1H), 3.91-3.97 (m, 1H), 4.00-4.09 (m, 1H), 5.09 (s, 1H), 7.89 (d, J=8.3 Hz, 2H), 7.96 (d, J=8.3 Hz, 2H). $^{19}$F NMR (376 MHz, DMSO-d$_6$)): δ –63.2 (s, 3F). LC-MS [M–H]$^-$ m/z 371.0 (calcd for $C_{14}H_{15}F_3N_4O_7S_2$, 472.03).

Example 12

(2S,5R)-7-Oxo-2-(N-(pyridin-2-ylsulfonyl)carbamimidoyl)-1,6-diazabicyclo[3.2.1]octan-6-yl hydrogen sulfate (Compound 61 in Table 1)

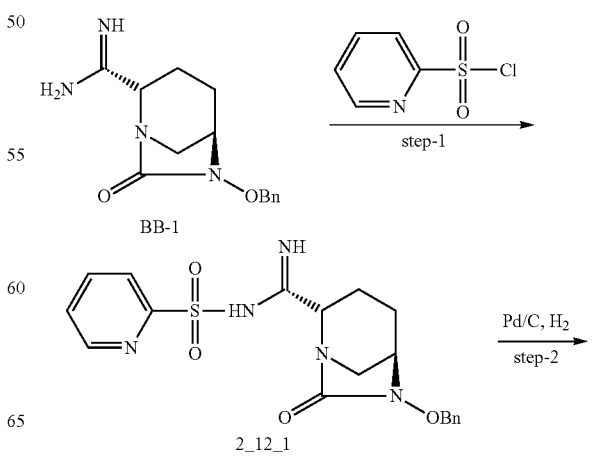

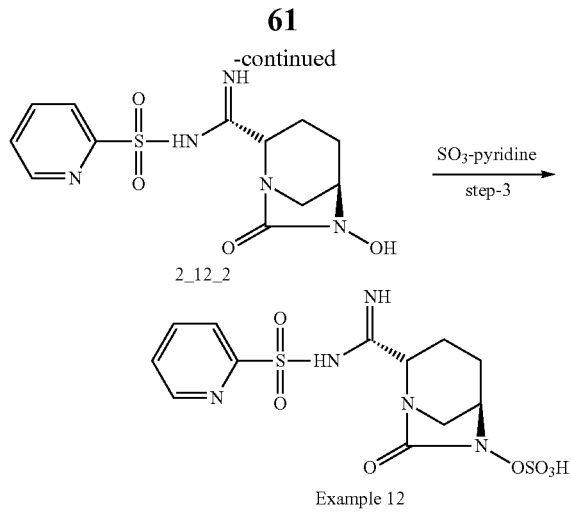

Example 12

Step-1: Synthesis of (2S,5R)-6-(benzyloxy)-7-oxo-N-(pyridin-2-ylsulfonyl)-1,6-diazabicyclo[3.2.1]octane-2-carboximidamide (2_12_1)

Pyridine-2-sulfonyl chloride (213 mg, 1.2 mmol, prepared based on ref. Journal of sulfur chemistry, 2020, vol 41, 463-473) and TEA (0.22 mL, 1.8 mmol) were added to a solution of BB-1 (164 mg, 0.6 mmol) in DCM (7 mL) at 0° C., and then stirred overnight at room temperature. The reaction mixture was concentrated to give a residue, which was purified by silica gel column chromatography eluting with 50% ethyl acetate in hexane to give the title compound 2_12_1 (248 mg, 99%) as a white gum. $^1$H NMR (400 MHz, DMSO-$d_6$): δ 1.79-1.93 (m, 3H), 1.98-2.04 (m, 1H), 3.02 (t, J=11.6 Hz, 1H), 3.78-3.84 (m, 1H), 3.91-3.99 (m, 1H), 4.78 (s, 2H), 5.13 (s, 1H), 6.77 (s, 2H), 7.31-7.35 (m, 3H), 7.41-7.45 (m, 2H), 7.75 (dd, J=7.5, 4.5 Hz, 1H), 7.99 (d, J=7.5 Hz, 1H), 8.13-8.18 (m, 1H), 8.77 (d, J=4.5 Hz, 1H). LC-MS [M+Na]$^+$ m/z 438.1 (calcd for $C_{19}H_{21}N_5O_4S$, 415.13).

Step 2: Synthesis of (2S,5R)-6-hydroxy-7-oxo-N-(pyridin-2-ylsulfonyl)-1,6-diazabicyclo[3.2.1]octane-2-carboximidamide (2_12_2)

10% Pd/C (wet, 200 mg) was added to a solution of compound 2_12_1 (250 mg, 0.6 mmol) in MeOH (5 mL). The reaction mixture was was stirred under $H_2$ (balloon) at room temperature for 18 hours, filtered through a pad of celite, rinsed with EtOAc. The filtrate was concentrated to give a residue, which was purified by silica gel column chromatography eluting with 10% MeOH in hexane to give the title compound 2_12_2 (150 mg, 76.9%) as a yellow oil. $^1$H NMR (400 MHz, DMSO-$d_6$): δ 1.68-1.79 (m, 3H), 1.86-1.95 (m, 1H), 3.02 (t, J=11.4 Hz, 1H), 3.74-3.80 (m, 1H), 3.93-4.05 (m, 1H), 5.13 (s, 1H), 6.49 (s, 2H), 7.76 (dd, J=7.5, 4.5 Hz, 1H), 8.01 (d, J=7.5 Hz, 1H), 8.13-8.18 (m, 1H), 8.80 (d, J=4.5 Hz, 1H), 9.26 (s, 1H). LC-MS [M+Na]$^+$ m/z 348.8 (calcd for $C_{12}H_{15}N_5O_4S$, 325.08).

Step 3: Synthesis of (2S,5R)-7-oxo-2-(N-(pyridin-2-ylsulfonyl)carbamimidoyl)-1,6-diazabicyclo[3.2.1]octan-6-yl hydrogen sulfate (Example 12)

A mixture of compound 2_12_2 (150 mg, 0.46 mmol), SO$_3$-pyridine (146 mg, 1.27 mmol) in pyridine (3 mL) was stirred at room temperature overnight. The reaction mixture was concentrated to give a residue, which was purified by resin Dowex-50wx Na$^+$ exchange using water as elution solvent, followed by preparative HPLC on an Agilent 10 prep-C18 250×21.2 mm column and lyophilized to give example 12 (41 mg, 22%) as a white solid. $^1$H NMR (400 MHz, D$_2$O): δ 1.86-1.99 (m, 3H), 2.04-2.11 (m, 1H), 3.10 (t, J=10.9 Hz, 1H), 3.94-4.04 (m, 2H), 5.09 (s, 1H), 7.68-7.72 (m, 1H), 8.02 (d, J=7.8 Hz, 1H), 8.07-8.13 (m, 1H), 8.67 (d, J=4.5 Hz, 1H). LC-MS [M−H]$^−$ m/z 404.1 (calcd for $C_{12}H_{15}N_5O_7S_2$, 405.04).

Example 13

Sodium (2S,5R)-7-oxo-2-(N-(pyridin-3-ylsulfonyl)carbamimidoyl)-1,6-diazabicyclo[3.2.1]octan-6-yl sulfate (Compound 39 in Table 1)

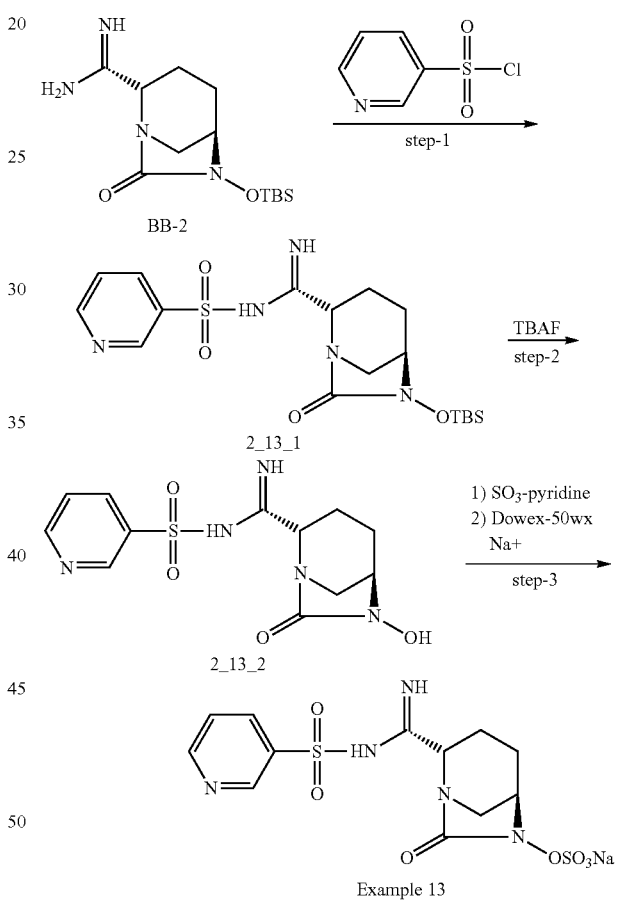

Example 13

Step-1: Synthesis of (2S,5R)-6-(benzyloxy)-7-oxo-N-(pyridin-3-ylsulfonyl)-1,6-diazabicyclo[3.2.1]octane-2-carboximidamide (2_13_1)

Pyridine-3-sulfonyl chloride (107 mg, 0.50 mmol) and TEA (0.22 mL, 1.8 mmol) were added to a solution of BB-2 (76 mg, 0.25 mmol) in CH$_2$Cl$_2$ (6 mL) at 0° C., and then stirred overnight at room temperature. The reaction mixture was concentrated to give a residue, which was purified by silica gel column chromatography eluting with 50% ethyl acetate in hexane to give the title compound 2_13_1 (100 mg, 92%) as a yellow oil. $^1$H NMR (400 MHz, DMSO-$d_6$):

δ 0.00 (s, 6H), 0.74 (s, 9H), 1.64-1.78 (m, 3H), 1.84-1.93 (m, 1H), 2.74 (t, J=11.3 Hz, 1H), 3.50-3.58 (m, 1H), 3.64 (dd, J=11.3, 4.2 Hz, 1H), 5.09 (s, 1H), 6.50 (br s, 2H), 7.60 (dd, J=7.9, 4.6 Hz, 1H), 8.13 (d, J=7.9 Hz, 1H), 8.80 (d, J=4.6 Hz, 1H), 8.87 (d, J=2.1 Hz, 1H). LC-MS [M+Na]$^+$ m/z 462.2 (calcd for $C_{18}H_{29}N_5O_4SSi$, 439.17).

Step 2: Synthesis of (2S,5R)-6-hydroxy-7-oxo-N-(pyridin-3-ylsulfonyl)-1,6-diazabicyclo[3.2.1]octane-2-carboximidamide (2_13_2)

TBAF (1 M in THF, 0.41 mL, 0.73 mmol) was added to a solution of compound 2_13_1 (100 mg, 0.23 mmol) in THF (5 mL) at 0° C. and stirred for 1 hour. The reaction mixture was concentrated to give a residue, which was diluted with EtOAc, washed with brine. The organic layer was dried over $Na_2SO_4$, filtered. The filtrate was purified by silica gel column chromatography eluting with 50% ethyl acetate in hexane to give the title compound 2_13_2 (41 mg, 54.8%) $^1$H NMR (400 MHz, DMSO-$d_6$): δ 1.71-1.78 (m, 2H), 1.90-2.10 (m, 2H), 2.74 (t, J=11.3 Hz, 1H), 3.72 (dd, J=11.3, 4.52 Hz, 1H), 4.04-4.16 (m, 1H), 5.25 (s, 1H), 6.53 (br s, 2H), 7.77 (dd, J=8.2, 4.8 Hz, 1H), 8.30 (dt, J=8.2, 1.9 Hz, 1H), 8.97 (dd, J=4.8, 1.4 Hz, 1H), 9.04 (d, J=2.3 Hz, 1H), 9.28 (s, 1H). LC-MS [M+Na]$^+$ m/z 348.8 (calcd for $C_{12}H_{15}N_5O_4S$, 325.08).

Step 3: Synthesis of sodium (2S,5R)-7-oxo-2-(N-(pyridin-3-ylsulfonyl)carbamimidoyl)-1,6-diazabicyclo[3.2.1]octan-6-yl sulfate (Example 13)

A mixture of compound 2_13_2 (40 mg, 0.12 mmol), $SO_3$-pyridine (63 mg, 0.40 mmol) in pyridine (2.5 mL) was stirred at room temperature overnight. The reaction mixture was concentrated to give a residue, which was purified by resin Dowex-50wx Na$^+$ exchange using water as elution solvent and lyophilized to give example 13 (61 mg, 14%) as a white solid. $^1$H NMR (400 MHz, $D_2O$): δ 1.84-2.01 (m, 3H), 2.05-2.12 (m, 1H), 2.96 (t, J=11.6 Hz, 1H), 3.93-3.98 (m, 1H), 4.04-4.15 (m, 1H), 5.12 (s, 1H), 7.67 (dd, J=8.1, 5.0 Hz, 1H), 8.26 (d, J=8.1 Hz, 1H), 8.78 (d, J=5.0 Hz, 1H), 8.97 (d, J=2.0 Hz, 1H). LC-MS [M−Na]$^−$ m/z 404.1 (calcd for $C_{12}H_{14}N_5NaO_7S_2$, 427.02).

Example 14

(2S,5R)-7-oxo-2-(N-((trifluoromethyl)sulfonyl)carbamimidoyl)-1,6-diazabicyclo[3.2.1]octan-6-yl hydrogen sulfate (Compound 70 in Table 1)

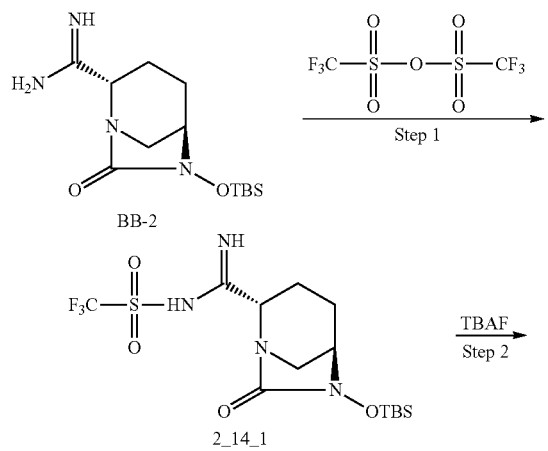

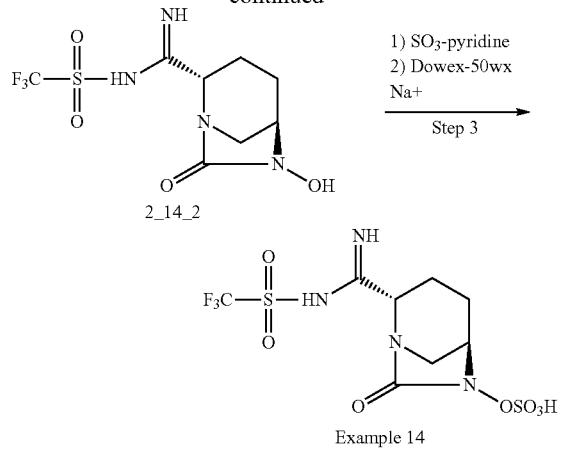

Example 14

Step 1: Synthesis of (2S,5R)-6-((tert-butyldimethylsilyl)oxy)-7-oxo-N-((trifluoromethyl)sulfonyl)-1,6-diazabicyclo[3.2.1]octane-2-carboximidamide (2_14_1)

Trifluoromethanesulfonic anhydride (0.22 mL, 0.6 mmol) was added to a solution of TEA (1.0 mL, 1.8 mmol) and BB-2 (370 mg, 1.30 mmol) in $CH_2Cl_2$ (10 mL) at −78° C. and then stirred for 18 hours at the same temperature under $N_2$. The reaction mixture was concentrated to give a residue, which was purified by silica gel column chromatography eluting with 50% ethyl acetate in petroleum ether to give the title compound 2_14_1 (150 mg, 26.8%) as a white foam. $^1$H NMR (400 MHz, DMSO-$d_6$): δ 0.15 (s, 3H), 0.17 (s, 3H), 0.94 (s, 9H), 1.92-2.03 (m, 3H), 2.10-2.17 (m, 1H), 3.49 (t, J=12.7 Hz, 1H), 3.64-3.73 (m, 1H), 3.77-3.88 (m, 1H), 5.47 (s, 1H), 6.73 (br s, 2H). $^{19}$F NMR (376 MHz, DMSO-$d_6$): δ −75.31 (s, 3F). LC-MS [M+Na]$^+$ m/z 453.1 (calcd for $C_{14}H_{25}F_3N_4O_4SSi$, 430.13).

Step 2: Synthesis of (2S,5R)-6-hydroxy-7-oxo-N-((trifluoromethyl)sulfonyl)-1,6-diazabicyclo[3.2.1]octane-2-carboximidamide (2_14_2)

TBAF (1 M in THF, 3 mL, 3.0 mmol) was added to a solution of compound 2_14_1 (150 mg, 0.34 mmol) in THF (3 mL) at 0° C. and stirred for 1 hour. The reaction mixture was concentrated to give a residue, which was diluted with EtOAc, washed with brine. The organic layer was dried over $Na_2SO_4$, filtered. The filtrate was purified by silica gel column chromatography eluting with 50% ethyl acetate in hexane to give the title compound 2_14_2 (50 mg, 15.8%) $^1$H NMR (400 MHz, DMSO-$d_6$): δ 1.78-2.05 (m, 3H), 2.10-2.17 (m, 1H), 3.28 (t, J=11.7 Hz, 1H), 3.71 (dd, J=12.6, 4.4 Hz, 1H), 4.03-4.13 (m, 1H), 5.47 (s, 1H), 6.56 (s, 2H), 9.39 (s, 1H). $^{19}$F NMR (376 MHz, DMSO-$d_6$): δ −75.03 (s, 3F). LC-MS [M+Na]$^+$ m/z 339.1 (calcd for $C_8H_{11}F_3N_4O_4S$, 316.05).

Step 3: Synthesis of (2S,5R)-7-oxo-2-(N-((trifluoromethyl)sulfonyl)carbamimidoyl)-1,6-diazabicyclo[3.2.1]octan-6-yl hydrogen sulfate (Example 14)

$SO_3$-pyridine (76 mg, 0.48 mmol) was added to a solution of 2_14_2 (50 mg, 0.16 mmol) in pyridine (1 mL). The reaction mixture was stirred at room temperature overnight and concentrated under reduced pressure to provide a residue. The residue was purified by resin Dowex-50wx Na⁺ exchange using water as elution solvent, followed by preparative HPLC on an Agilent 10 prep-C18 250×21.2 mm column and lyophilized to give to give example 14 (18 mg, 28%) as a white solid. 1H NMR (400 MHz, D$_2$O): δ 1.89-2.15 (m, 4H), 3.51 (t, J=11.6 Hz, 1H), 3.92-4.06 (m, 2H), 5.19-5.23 (m, 1H). $^{19}$F NMR (376 MHz, D$_2$O): δ −75.18 (s, 3 F). LC-MS [M−H]⁻ m/z 395.0 (calcd for C$_8$H$_{11}$F$_3$N$_4$O$_7$S$_2$, 396.00).

Example 15

(2S,5R)-2-(N-(azetidin-1-ylsulfonyl)carbamimidoyl)-7-oxo-1,6-diazabicyclo[3.2.1]octan-6-yl hydrogen sulfate (Compound 80 in Table 1)

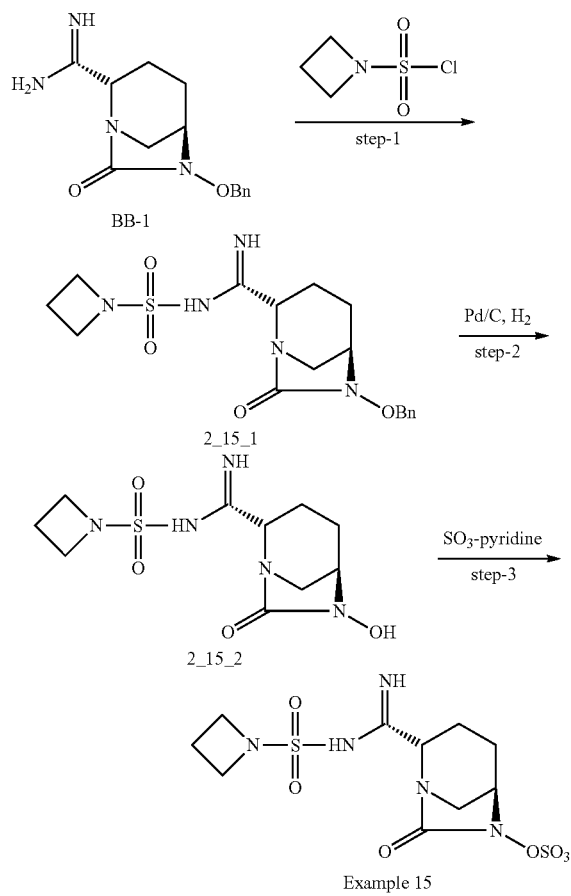

Step-1: Synthesis of (2S,5R)—N-(azetidin-1-ylsulfonyl)-6-(benzyloxy)-7-oxo-1,6-diazabicyclo[3.2.1]octane-2-carboximidamide (2_15_1)

Azetidine-1-sulfonyl chloride (187 mg, 2.0 mmol) and TEA (0.22 mL, 1.8 mmol) were added to a solution of BB-1 (164 mg, 0.6 mmol) in DCM (5 mL) at 0° C., and then stirred overnight at room temperature. The reaction mixture was concentrated to give a residue, which was purified by silica gel column chromatography eluting with 50% ethyl acetate in hexane to give the title compound 2_15_1 (113 mg, 48%) as a white gum. ¹H NMR (400 MHz, DMSO-d$_6$): δ 1.81-1.91 (m, 3.5H), 1.97-2.08 (m, 1.5H), 2.13-2.22 (m, 1H), 2.91-3.01 (m, 1.5H), 3.06-3.12 (m, 0.5H), 3.44-3.51 (m, 1H), 3.67 (t, J=10.9 Hz, 1H), 3.77-3.84 (m, 2H), 3.91-4.01 (m, 1H), 4.81 (s, 2H), 4.84 (s, 0.5H), 4.93 (s, 0.5H), 6.78 (s, 2H), 7.34-7.40 (m, 3H), 7.46-7.51 (m, 2H). LC-MS [M+Na]⁺ m/z 416.1 (calcd for C$_1$H$_{24}$N$_5$O$_4$S, 393.15).

Step 2: Synthesis of (2S,5R)—N-(azetidin-1-ylsulfonyl)-6-hydroxy-7-oxo-1,6-diazabicyclo[3.2.1]octane-2-carboximidamide (2_15_2)

10% Pd/C (wet, 90 mg) was added to a solution of compound 2_15_1 (113 mg, 0.29 mmol) in MeOH (5 mL) with a few drops of TEA. The reaction mixture was was stirred under H$_2$ (balloon) at room temperature for 18 hours, filtered through a pad of celite, rinsed with EtOAc. The filtrate was concentrated to give a residue, which was purified by silica gel column chromatography eluting with 10% MeOH in hexane to give the title compound 2_15_2 (45 mg, 76.9%) as a white gum. ¹H NMR (400 MHz, DMSO-d$_6$): δ 1.65-1.92 (m, 4H), 2.00-2.06 (m, 1H), 2.16-2.23 (m, 1H), 2.88-3.01 (m, 2H), 3.39-3.49 (m, 1H), 3.67 (t, J=6.4 Hz, 1H), 3.84 (t, J=7.7 Hz, 2H), 3.94-4.02 (m, 1H), 4.83 (s, 0.5H), 4.96 (s, 0.5H), 6.49 (s, 1H), 6.50 (s, 1H), 9.26 (s, 0.5H), 9.27 (s, 0.5H). LC-MS [M+Na]⁺ m/z 326.1 (calcd for C$_{10}$H$_{17}$N$_5$O$_4$S, 303.10).

Step 3: Synthesis of (2S,5R)-2-(N-(azetidin-1-ylsulfonyl)carbamimidoyl)-7-oxo-1,6-diazabicyclo[3.2.1]octan-6-yl hydrogen sulfate (Example 15)

A mixture of compound 2_15_2 (45 mg, 0.15 mmol), SO$_3$-pyridine (72 mg, 0.45 mmol) in pyridine (3 mL) was stirred at room temperature overnight. The reaction mixture was concentrated to give a residue, which was purified by resin Dowex-50wx Na⁺ exchange using water as elution solvent, followed by preparative HPLC on an Agilent 10 prep-C18 250×21.2 mm column and lyophilized to give example 15 (12 mg, 20%) as a white solid. ¹H NMR (400 MHz, D$_2$O): δ 1.86-2.03 (m, 3H), 2.09-2.15 (m, 1H), 2.17-2.26 (m, 2H), 3.12-3.18 (m, 1H), 3.27 (t, J=11.1 Hz, 1H), 3.59-3.64 (m, 1H), 3.76-3.82 (m, 1H), 3.90 (s, J=7.6 Hz, 2H), 3.98-4.06 (m, 1H), 4.93 (m, 1H). LC-MS [M−H]⁻ m/z 382.1 (calcd for C$_{10}$H$_{17}$N$_5$O$_7$S$_2$, 383.06).

Example 16

(2S,5R)-7-oxo-2-(N-Sulfamoylcarbamimidoyl)-1,6-diazabicyclo[3.2.1]octan-6-yl hydrogen sulfate (Compound 75 In Table 1)

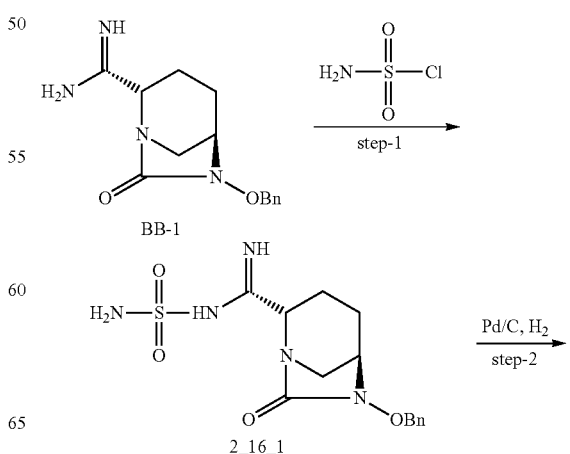

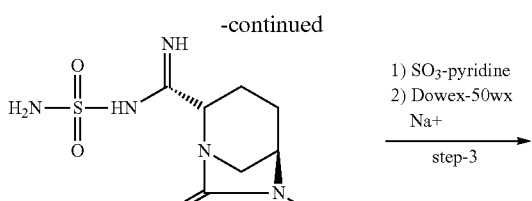

Step-1: Synthesis of (2S,5R)-6-(benzyloxy)-7-oxo-N-sulfamoyl-1,6-diazabicyclo[3.2.1]octane-2-carboximidamide (2_16_1)

Sulfamoyl chloride (139 mg, 1.2 mmol) and TEA (0.23 mL, 1.8 mmol) were added to a solution of BB-1 (164 mg, 0.6 mmol) in $CH_2Cl_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_16_1 (150 mg, 70%) as a white foam. $^1H$ NMR (400 MHz, DMSO-$d_6$): δ 1.78-1.93 (m, 3H), 2.01-2.07 (m, 1H), 2.96 (t, J=11.3 Hz, 1H), 3.54 (d, J=9.8 Hz, 1H), 3.97-4.06 (m, 1H), 4.77-4.86 (m, 3H), 6.71 (br s, 2H), 7.32 (s, 2H), 7.34-7.40 (m, 3H), 7.47-7.52 (m, 2H). LC-MS [M+Na]$^+$ m/z 376.1 (calcd for $C_{14}H_{19}N_5O_4S$, 353.12).

Step 2: Synthesis of (2S,5R)-6-hydroxy-7-oxo-N-sulfamoyl-1,6-diazabicyclo[3.2.1]octane-2-carboximidamide (2_16_2)

10% Pd/C (wet, 100 mg) was added to a solution of compound 2_16_1 (150 mg, 0.42 mmol) in THF (5 mL) with three drops of TEA. The reaction mixture was stirred under $H_2$ (balloon) at room temperature for 18 hours, filtered through a pad of celite, rinsed with EtOAc. The filtrate was concentrated to give the title compound 2_16_2 (97 mg, 87.8%) as an oil, which was directly used for next step without further purification. $^1H$ NMR (400 MHz, DMSO-$d_6$): δ 1.71-1.85 (m, 3H), 2.00-2.05 (m, 1H), 2.88 (t, J=11.4 Hz, 1H), 3.46 (dd, J=11.5, 4.3 Hz, 1H), 3.97-4.05 (m, 1H), 4.81 (s, 1H), 6.45 (s, 2H), 7.30 (br s, 2H), 9.25 (s, 1H). LC-MS [M+Na]$^+$ m/z 286.0 (calcd for $C_7H_{13}N_5O_4S$, 263.07).

Step 3: Synthesis of (2S,5R)-7-oxo-2-(N-sulfamoyl-carbamimidoyl)-1,6-diazabicyclo[3.2.1]octan-6-yl hydrogen sulfate (Example 16)

A mixture of compound 2_16_2 (40 mg, 0.12 mmol), $SO_3$-pyridine (63 mg, 0.40 mmol) in pyridine (2.5 mL) was stirred at room temperature overnight. The reaction mixture was concentrated to give a residue, which was purified by resin Dowex-50wx Na$^+$ exchange using water as elution solvent and lyophilized, followed by preparative HPLC on an Agilent 10 prep-C18 250×21.2 mm column and lyophilized to afford example 16 (15 mg, 34%) as a white solid. $^1H$ NMR (400 MHz, $D_2O$): δ 1.82-1.93 (m, 3H), 2.01-2.07 (m, 1H), 3.07 (t, J=11.4 Hz, 1H), 3.63-3.69 (m, 1H), 3.95-4.03 (m, 1H), 4.81 (s, 1H) LC-MS [M–H]$^-$ m/z 342.1 (calcd for $C_7H_{13}N_5O_7S$, 343.03).

Example 17

(2S,5R)-2-(N—(N-Methylsulfamoyl)carbamimidoyl)-7-oxo-1,6-diazabicyclo[3.2.1]octan-6-yl hydrogen sulfate (Compound 76 in Table 1)

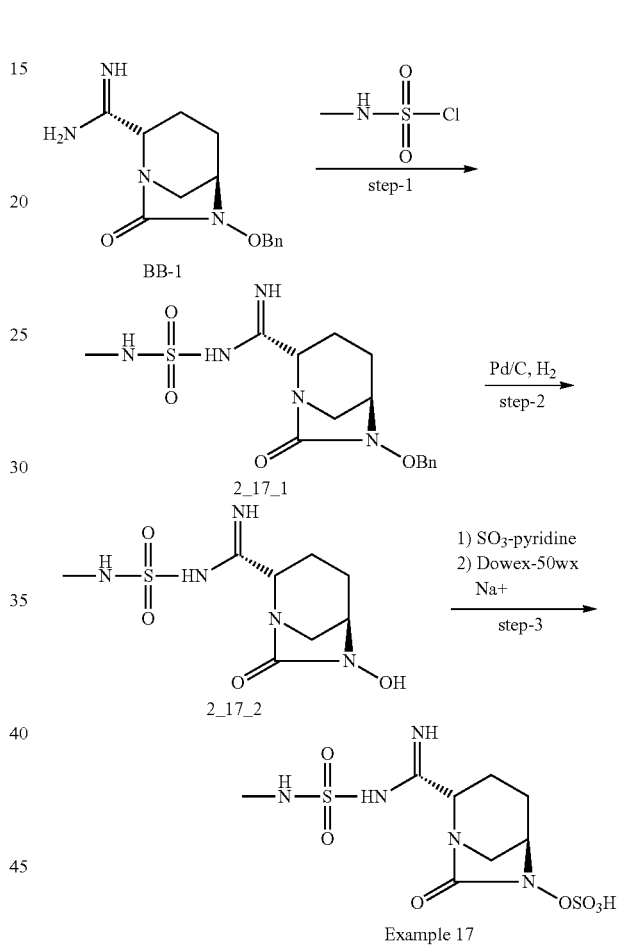

Step-1: Synthesis of (2S,5R)-6-(benzyloxy)-N—(N-methylsulfamoyl)-7-oxo-1,6-diazabicyclo[3.2.1]octane-2-carboximidamide (2_17_1)

Methylsulfamoyl chloride (156 mg, 1.2 mmol) and TEA (0.23 mL, 1.8 mmol) were added to a solution of BB-1 (164 mg, 0.60 mmol) in $CH_2Cl_2$ (6 mL) at 0° C., and then stirred overnight at room temperature. The reaction mixture was concentrated to give a residue, which was purified by silica gel column chromatography eluting with 50% ethyl acetate in petroleum ether to give the title compound 2_17_1 (157 mg, 72%) as a white foam. $^1H$ NMR (400 MHz, DMSO-$d_6$): δ 1.80-1.91 (m, 3H), 2.02-2.07 (m, 1H), 2.48 (d, J=4.9 Hz, 3H), 2.96 (t, J=11.4 Hz, 1H), 3.45-3.51 (m, 1H), 3.93-4.01 (m, 1H), 4.82 (s, 3H), 6.75 (br s, 2H), 7.35-7.50 (m, 3H), 7.47-7.50 (m, 2H), 7.62 (q, J=4.9 Hz, 1H). LC-MS [M+Na]$^+$ m/z 390.1 (calcd for $C_{15}H_{21}N_5O_4S$, 367.13).

Step 2: Synthesis of (2S,5R)-6-hydroxy-N—(N-methylsulfamoyl)-7-oxo-1,6-diazabicyclo[3.2.1]octane-2-carboximidamide (2_17_2)

10% Pd/C (wet, 110 mg) was added to a solution of compound 2_17_1 (157 mg, 0.43 mmol) in THF (5 mL) with three drops of TEA. The reaction mixture was stirred under $H_2$ (balloon) at room temperature for 18 hours, filtered through a pad of celite, rinsed with EtOAc. The filtrate was concentrated to give the title compound 2_17_2 (110 mg, 92%) as an oil, which was directly used for next step without further purification. $^1$H NMR (400 MHz, DMSO-$d_6$): δ 1.76-1.87 (m, 3H), 2.01-2.06 (m, 1H), 2.49 (d, J=3.5 Hz, 3H), 2.92 (t, J=11.3 Hz, 1H), 3.40 (dd, J=11.4, 4.2 Hz, 1H), 3.95-4.08 (m, 1H), 4.81 (s, 1H), 6.43 (s, 2H), 7.60 (br s, 1H), 9.26 (s, 1H). LC-MS [M+Na]$^+$ m/z 300.1 (calcd for $C_8H_{15}N_5O_4S$, 277.08).

Step 3: Synthesis of (2S,5R)-2-(N—(N-methylsulfamoyl)carbamimidoyl)-7-oxo-1,6-diazabicyclo[3.2.1]octan-6-yl hydrogen sulfate (Example 17)

A mixture of compound 2_17_2 (40 mg, 0.12 mmol), SO$_3$-pyridine (63 mg, 0.40 mmol) in pyridine (2.5 mL) was stirred at room temperature overnight. The reaction mixture was concentrated to give a residue, which was purified by resin Dowex-50wx Na$^+$ exchange using water as elution solvent and lyophilized, followed by preparative HPLC on an Agilent 10 prep-C18 250×21.2 mm column and lyophilized to afford example 17 (19 mg, 45%) as a white solid. $^1$H NMR (400 MHz, DMSO-$d_6$): δ 1.83-1.95 (m, 3H), 2.02-2.08 (m, 1H), 2.52 (s, 3H), 3.15 (t, J=11.6 Hz, 1H), 3.58-3.64 (m, 1H), 3.93-4.00 (m, 1H), 4.81 (s, 1H). LC-MS [M−Na]$^-$ m/z 356.0 (calcd for $C_8H_{15}N_5O_7S_2$, 357.04).

Example 18

(2S,5R)-2-(N—(N-Ethylsulfamoyl)carbamimidoyl)-7-oxo-1,6-diazabicyclo[3.2.1]octan-6-yl hydrogen sulfate (Compound 79 in Table 1)

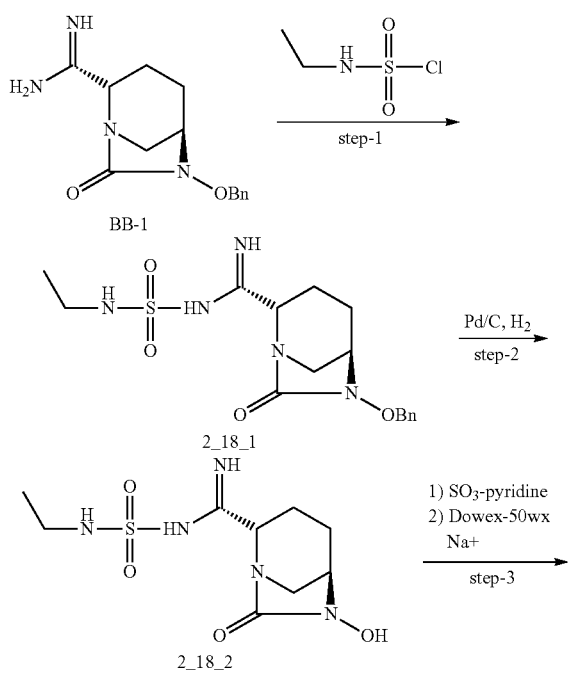

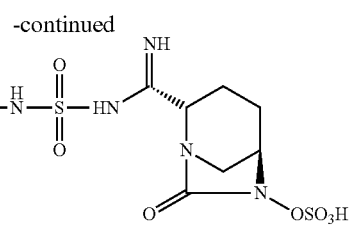

Example 18

Step-1: Synthesis of (2S,5R)-6-(benzyloxy)-N—(N-ethylsulfamoyl)-7-oxo-1,6-diazabicyclo[3.2.1]octane-2-carboximidamide (2_18_1)

Ethylsulfamoyl chloride (172 mg, 1.2 mmol) and TEA (0.23 mL, 1.8 mmol) were added to a solution of BB-1 (164 mg, 0.6 mmol) in CH$_2$Cl$_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_18_1 (197 mg, 87%) as a white foam. $^1$H NMR (400 MHz, DMSO-$d_6$): δ 1.05 (t, J=7.2 Hz, 3H), 1.76-1.90 (m, 3H), 2.01-2.07 (m, 1H), 2.88-2.91 (m, 2H), 2.94 (t, J=11.4 Hz, 1H), 3.46-3.52 (m, 1H), 3.92-4.00 (m, 1H), 4.82 (s, 3H), 6.75 (br s, 2H), 7.33-7.40 (m, 3H), 7.47-7.50 (m, 2H), 7.72 (t, J=5.4 Hz, 1H). LC-MS [M+Na]$^+$ m/z 404.1 (calcd $C_{16}H_{23}N_5O_4S$, 381.15).

Step 2: Synthesis of (2S,5R)—N—(N-ethylsulfamoyl)-6-hydroxy-7-oxo-1,6-diazabicyclo[3.2.1]octane-2-carboximidamide (2_18_2)

10% Pd/C (wet, 130 mg) was added to a solution of compound 2_18_1 (197 mg, 0.52 mmol) in THF (5 mL) with four drops of TEA. The reaction mixture was stirred under $H_2$ (balloon) at room temperature for 18 hours, filtered through a pad of celite, rinsed with EtOAc. The filtrate was concentrated to give the title compound 2_18_2 (145 mg, 95%) as an oil, which was directly used for next step without further purification. $^1$H NMR (400 MHz, DMSO-$d_6$): δ 1.04 (t, J=7.2 Hz, 3H), 1.72-1.90 (m, 3H), 2.01-2.07 (m, 1H), 2.80-2.89 (m, 2H), 2.90 (t, J=11.6 Hz, 1H), 3.48-3.55 (m, 1H), 3.95-4.04 (m, 1H), 4.81 (s, 1H), 6.35 (s, 1H), 6.46 (s, 1H), 7.12 (s, 1H), 9.08 (t, J=5.4 Hz, 1H). LC-MS [M+Na]$^+$ m/z 314.1 (calcd for $C_9H_{17}N_5O_4S$, 291.10).

Step 3: Synthesis of (2S,5R)-2-(N—(N-ethylsulfamoyl)carbamimidoyl)-7-oxo-1,6-diazabicyclo[3.2.1]octan-6-yl hydrogen sulfate (Example 18)

A mixture of compound 2_18_2 (160 mg, 0.55 mmol), SO$_3$-pyridine (350 mg, 2.2 mmol) in pyridine (5 mL) was stirred at room temperature overnight. The reaction mixture was concentrated to give a residue, which was purified by resin Dowex-50wx Na$^+$ exchange using water as elution solvent and lyophilized, followed by preparative HPLC on an Agilent 10 prep-C18 250×21.2 mm column and lyophilized to afford example 18 (9 mg, 4.4%) as a white solid. $^1$H NMR (400 MHz, DMSO-$d_6$): δ 1.00 (t, J=7.2 Hz, 3H), 1.83-1.95 (m, 3H), 2.02-2.07 (m, 1H), 2.93 (q, J=7.2 Hz, 2H), 3.12 (t, J=11.6 Hz, 1H), 3.58-3.65 (m, 1H), 3.91-3.99 (m, 1H), 4.81 (s, 1H). LC-MS [M−H]$^-$ m/z 370.0 (calcd for $C_9H_{17}N_5O_7S_2$, 371.0).

Example 19

(2S,5R)-2-(N-((1-methyl-1H-imidazol-2-yl)sulfonyl)carbamimidoyl)-7-oxo-1,6-diazabicyclo[3.2.1]octan-6-yl hydrogen sulfate (Compound 103 in Table 1)

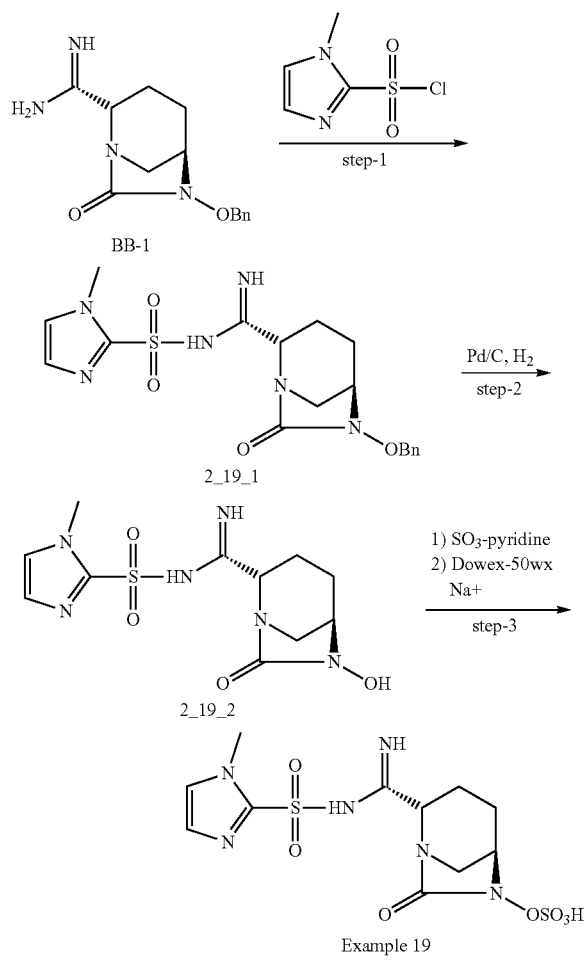

Step-1: Synthesis of (2S,5R)-6-(benzyloxy)-N-((1-methyl-1H-imidazol-2-yl)sulfonyl)-7-oxo-1,6-diazabicyclo[3.2.1]octane-2-carboximidamide (2_19_1)

1-Methyl-1H-imidazole-2-sulfonyl chloride (500 mg, 1.2 mmol) and TEA (0.23 mL, 1.8 mmol) were added to a solution of BB-1 (164 mg, 0.6 mmol) in CH$_2$Cl$_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_19_1 (60 mg, 23%) as a white foam. $^1$H NMR (400 MHz, DMSO-d$_6$): δ 1.80-2.05 (m, 4H), 3.07 (t, J=11.6 Hz, 1H), 3.70-3.77 (m, 1H), 3.89 (s, 3H), 3.95-4.02 (m, 1H), 4.77 (d, J=11.3 Hz, 1H), 4.81 (d, J=11.3 Hz, 1H), 5.18 (br s, 1H), 6.75 (br s, 2H), 7.15 (s, 1H), 7.32-7.39 (m, 3H), 7.43-7.48 (m, 2H), 7.52 (s, 1H). LC-MS [M+Na]$^+$ m/z 441.1 (calcd C$_{18}$H$_{22}$N$_6$O$_4$S, 418.14).

Step 2: Synthesis of (2S,5R)-6-hydroxy-N-((1-methyl-1H-imidazol-2-yl)sulfonyl)-7-oxo-1,6-diazabicyclo[3.2.1]octane-2-carboximidamide (2_19_2)

10% Pd/C (wet, 45 mg) was added to a solution of compound 2_19_1 (60 mg, 0.14 mmol) in THF (5 mL) with two drops of TEA. The reaction mixture was stirred under H$_2$ (balloon) at room temperature for 18 hours, filtered through a pad of celite, rinsed with EtOAc. The filtrate was concentrated to give the title compound 2_19_2 (47 mg, 99%) as an oil, which was directly used for next step without further purification. $^1$H NMR (400 MHz, DMSO-d$_6$): δ 1.70-2.05 (m, 2H), 1.91-2.06 (m, 2H), 3.04 (t, J=11.7 Hz, 1H), 3.66-3.71 (m, 1H), 3.90 (s, 3H), 3.97-4.05 (m, 1H), 5.18 (br s, 1H), 6.48 (br s, 2H), 7.15 (s, 1H), 7.53 (s, 1H), 9.27 (s, 1H). LC-MS [M+Na]$^+$ m/z 441.1 (calcd C$_{18}$H$_{22}$N$_6$O$_4$S, 418.14). LC-MS [M+Na]$^+$ m/z 351.1 (calcd for C$_{11}$H$_{16}$N$_6$O$_4$S, 328.09).

Step 3: Synthesis of (2S,5R)-2-(N-((1-methyl-1H-imidazol-2-yl)sulfonyl)carbamimidoyl)-7-oxo-1,6-diazabicyclo[3.2.1]octan-6-yl hydrogen sulfate (Example 19)

A mixture of compound 2_19_2 (57 mg, 0.17 mmol), SO$_3$-pyridine (43 mg, 0.27 mmol) in pyridine (3 mL) was stirred at room temperature overnight. The reaction mixture was concentrated to give a residue, which was purified by resin Dowex-50wx Na$^+$ exchange using water as elution solvent and lyophilized, followed by preparative HPLC on an Agilent 10 prep-C18 250×21.2 mm column and lyophilized to afford example 19 (12 mg, 17%) as a white solid. $^1$H NMR (400 MHz, DMSO-d$_6$): δ 1.90-1.98 (m, 1H), 2.02-2.15 (m, 3H), 3.18 (t, J=11.5 Hz, 1H), 3.90 (s, 3H), 3.96-4.08 (m, 2H), 5.09 (s, 1H), 7.15 (s, 1H), 7.32 (s, 1H). LC-MS [M−H]$^-$ m/z 407.1 (calcd for C$_{11}$H$_{16}$N$_6$O$_7$S$_1$, 408.0). LC-MS [M−H]$^-$ 407.1 (calcd for C$_{11}$H$_{16}$N$_6$O$_7$S$_2$, 408.40).

Example 20

(2S,5R)-7-oxo-2-(N-((5-(trifluoromethyl)pyridin-2-yl)sulfonyl)carbamimidoyl)-1,6-diazabicyclo[3.2.1]octan-6-yl hydrogen sulfate (Compound 51 in Table 1)

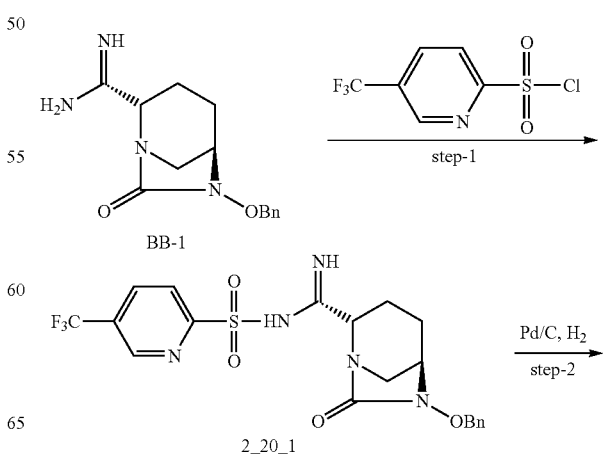

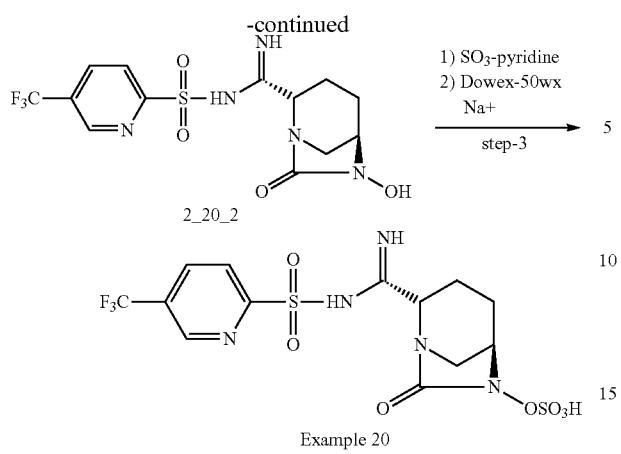

was concentrated to give a residue, which was purified by resin Dowex-50wx Na+ exchange using water as elution solvent and lyophilized, followed by preparative HPLC on an Agilent 10 prep-C18 250×21.2 mm column and lyophilized to afford example 20 (51 mg, 20%) as a white solid. $^1$H NMR (400 MHz, D$_2$O): δ 1.83-1.91 (m, 3H), 2.01-2.07 (m, 1H), 3.08 (t, J=11.8 Hz, 1H), 3.89-4.00 (m, 2H), 5.09 (s, 1H), 8.15 (d, J=8.4 Hz, 1H), 8.38 (d, J=8.4 Hz, 1H), 8.97 (s, 1H). $^{19}$F NMR (376 MHz, D$_2$O): δ −63.0 (s, 3 F). LC-MS [M−H]$^−$ m/z 472.0 (calcd for C$_{13}$H$_{14}$F$_3$N$_5$O$_7$S$_2$, 473.02).

Example 21

(2S,5R)-2-(N-((6-methoxypyridin-3-yl)sulfonyl) carbamimidoyl)-7-oxo-1,6-diazabicyclo[3.2.1]octan-6-yl hydrogen sulfate (Compound 104 in Table 1)

Step-1: Synthesis of (2S,5R)-6-(benzyloxy)-7-oxo-N-((5-(trifluoromethyl)pyridin-2-yl)sulfonyl)-1,6-diazabicyclo[3.2.1]octane-2-carboximidamide (2_20_1)

5-(Trifluoromethyl)pyridine-2-sulfonyl chloride (300 mg, 1.2 mmol) and TEA (0.26 mL, 1.8 mmol) were added to a solution of BB-1 (164 mg, 0.6 mmol) in CH$_2$Cl$_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_20_1 (280 mg, 96%) as a white foam. $^1$H NMR (400 MHz, DMSO-d$_6$): δ 1.79-2.05 (m, 4H), 3.00 (t, J=11.8 Hz, 1H), 3.82 (dd, J=11.8, 4.1 Hz, 1H), 3.92-4.00 (m, 1H), 4.79 (s, 2H), 5.19 (s, 1H), 6.78 (br s, 2H), 7.31-7.34 (m, 3H), 7.41-7.46 (m, 2H), 8.22 (d, J=8.1 Hz, 1H), 8.62 (dd, J=8.1, 2.2 Hz, 1H), 9.22 (s, 1H). $^{19}$F NMR (376 MHz, DMSO-d$_6$): δ −61.22 (s, 3F). LC-MS [M+Na]$^+$ m/z 506.1 (calcd C$_{20}$H$_{20}$F$_3$N$_5$O$_4$S, 483.11).

Step 2: Synthesis of (2S,5R)-6-hydroxy-7-oxo-N-((5-(trifluoromethyl)pyridin-2-yl)sulfonyl)-1,6-diazabicyclo[3.2.1]octane-2-carboximidamide (2_20_2)

10% Pd/C (dry, 310 mg) was added to a solution of compound 2_20_1 (280 mg, 0.58 mmol) in THF (5 mL) with two drops of TEA. The reaction mixture was stirred under H$_2$ (balloon) at room temperature for 3 hours, filtered through a pad of celite, rinsed with EtOAc. The filtrate was concentrated to give the title compound 2_20_2 (210 mg, 92%) as an oil, which was directly used for next step without further purification. $^1$H NMR (400 MHz, DMSO-d$_6$): δ 1.70-1.80 (m, 2H), 1.88-1.98 (m, 1H), 2.00-2.07 (m, 1H), 3.04 (t, J=11.6 Hz, 1H), 3.81 (dd, J=11.6, 4.5 Hz, 1H), 3.96-4.05 (m, 1H), 5.19 (s, 1H), 6.51 (br s, 2H), 8.24 (d, J=8.2 Hz, 1H), 8.63 (dd, J=8.2, 1.9 Hz, 1H), 9.28 (d, J=1.9 Hz, 1H), 9.29 (s, 1H). LC-MS [M+Na]$^+$ m/z 416.1 (calcd for C$_{13}$H$_{14}$F$_3$N$_6$O$_4$S, 393.07).

Step 3: Synthesis of (2S,5R)-7-oxo-2-(N-((5-(trifluoromethyl)pyridin-2-yl)sulfonyl)carbamimidoyl)-1,6-diazabicyclo[3.2.1]octan-6-yl hydrogen sulfate (Example 20)

A mixture of compound 2_20_2 (210 mg, 0.53 mmol), SO$_3$-pyridine (315 mg, 1.98 mmol) in pyridine (5 mL) was stirred at room temperature overnight. The reaction mixture

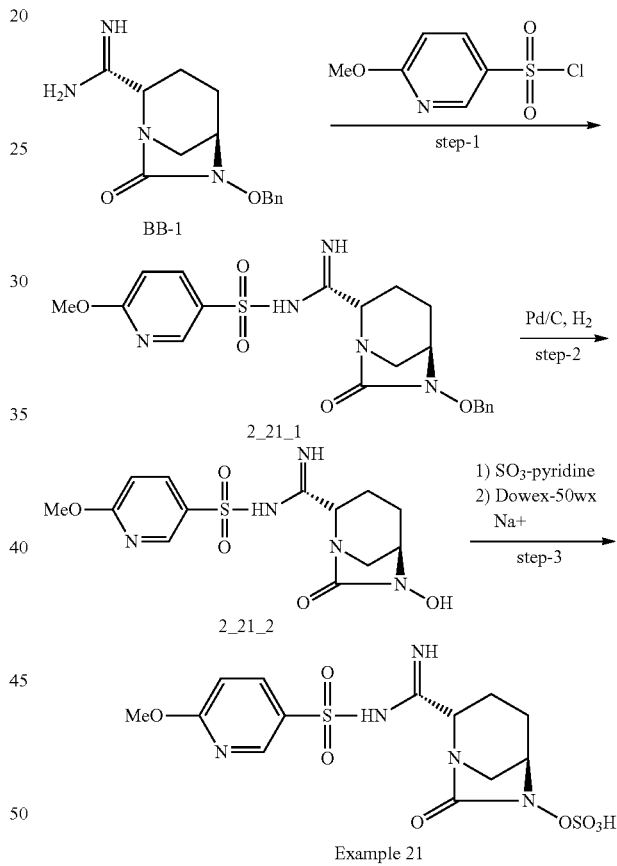

Step-1: Synthesis of (2S,5R)-6-(benzyloxy)-N-((6-methoxypyridin-3-yl)sulfonyl)-7-oxo-1,6-diazabicyclo[3.2.1]octane-2-carboximidamide (2_21_1)

6-Methoxypyridine-3-sulfonyl chloride (250 mg, 1.2 mmol) and TEA (0.26 mL, 1.8 mmol) were added to a solution of BB-1 (164 mg, 0.6 mmol) in CH$_2$Cl$_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_21_1 (260 mg, 97%) as a white foam. $^1$H NMR (400 MHz, DMSO-d$_6$): δ 1.69-1.93 (m, 3H), 1.95-2.03 (m, 1H), 2.64 (t, J=11.2 Hz, 1H), 3.71 (d, J=11.2 Hz, 1H), 3.96 (s, 3H), 3.97-4.05 (m, 1H), 4.79 (s, 2H), 5.14 (s, 1H), 6.78 (br s, 2H), 7.06 (d, J=8.7 Hz, 1H), 7.29-7.35 (m, 3H), 7.36-7.43 (m, 2H), 8.07 (dd, J=8.7, 2.4 Hz, 1H), 8.64 (d, J=2.4 Hz, 1H). LC-MS [M+Na]$^+$ m/z 468.1 (calcd $C_{20}H_{23}N_5O_5S$, 445.14).

Step 2: Synthesis of (2S,5R)-6-hydroxy-N-((6-methoxypyridin-3yl)sulfonyl)-7-oxo-1,6-diazabicyclo[3.2.1]octane-2-carboximidamide (2_21_2)

10% Pd/C (dry, 240 mg) was added to a solution of compound 2_21_1 (260 mg, 0.58 mmol) in THF (5 mL) with two drops of TEA. The reaction mixture was stirred under $H_2$ (balloon) at room temperature for 3 hours, filtered through a pad of celite, rinsed with EtOAc. The filtrate was concentrated to give the title compound 2_21_2 (180 mg, 92%) as an oil, which was directly used for next step without further purification. $^1$H NMR (400 MHz, DMSO-$d_6$): δ 1.74-1.84 (m, 2H), 1.91-2.00 (m, 1H), 2.05-2.12 (m, 1H), 2.76 (t, J=11.2 Hz, 1H), 3.69 (dd, J=11.2, 4.7 Hz, 1H), 4.03 (s, 3H), 4.06-4.16 (m, 1H), 5.21 (s, 1H), 6.52 (br s, 2H), 7.14 (d, J=8.8 Hz, 1H), 8.14 (dd, J=8.8, 2.4 Hz, 1H), 8.70 (d, J=2.4 Hz, 1H), 9.30 (s, 1H). LC-MS [M+Na]$^+$ m/z 468.1 (calcd $C_{20}H_{23}N_5O_5S$, 445.14). LC-MS [M+Na]$^+$ m/z 378.1 (calcd for $C_{13}H_{17}N_5O_5S$, 355.09).

Step 3: Synthesis of (2S,5R)-2-(N-((6-methoxypyridin-3-yl)sulfonyl)carbamimidoyl)-7-oxo-1,6-diazabicyclo[3.2.1]octan-6-yl hydrogen sulfate (Example 21)

A mixture of compound 2_21_2 (180 mg, 0.58 mmol), SO$_3$-pyridine (240 mg, 1.50 mmol) in pyridine (3 mL) was stirred at room temperature overnight. The reaction mixture was concentrated to give a residue, which was purified by resin Dowex-50wx Na$^+$ exchange using water as elution solvent and lyophilized, followed by preparative HPLC on an Agilent 10 prep-C18 250×21.2 mm column and lyophilized to afford example 21 (27 mg, 11%) as a white solid. $^1$H NMR (400 MHz, D$_2$O): δ 1.87-2.01 (m, 3H), 2.09-2.15 (m, 1H), 2.98 (t, J=11.4 Hz, 1H), 3.90-3.94 (m, 1H), 3.95 (s, 3H), 4.06-4.15 (m, 1H), 5.09 (s, 1H), 7.04 (d, J=8.8 Hz, 1H), 8.08 (d, J=8.8, 2.1 Hz, 1H), 8.59 (s, 1H). LC-MS [M−H]$^−$ m/z 434.1 (calcd for $C_{13}H_{17}N_5O_8S$, 435.05).

Example 22

(2S,5R)-2-(N-((5-methoxypyridin-2-yl)sulfonyl)carbamimidoyl)-7-oxo-1,6-diazabicyclo[3.2.1]octan-6-yl hydrogen sulfate (Compound 105 in Table 1)

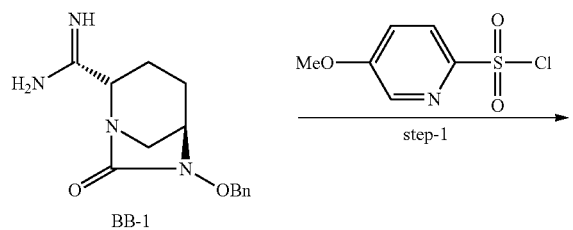

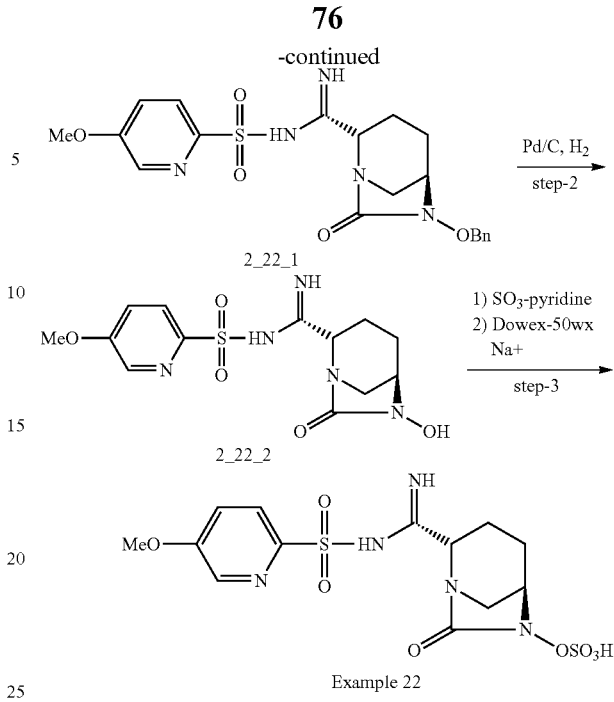

Example 22

Step-1: Synthesis of (2S,5R)-6-(benzyloxy)-N-((5-methoxypyridin-2-yl)sulfonyl)-7-oxo-1,6-diazabicyclo[3.2.1]octane-2-carboximidamide (2_22_1)

5-Methoxypyridine-2-sulfonyl chloride (248 mg, 1.2 mmol) and TEA (0.26 mL, 1.8 mmol) were added to a solution of BB-1 (164 mg, 0.6 mmol) in CH$_2$Cl$_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_22_1 (26 mg, 97%) as a white foam. $^1$H NMR (400 MHz, DMSO-$d_6$): δ 1.79-1.93 (m, 3H), 1.98-2.04 (m, 1H), 2.97 (t, J=11.7 Hz, 1H), 3.78 (dd, J=11.7, 4.1 Hz, 1H), 3.92 (s, 3H), 3.93-3.98 (m, 1H), 4.76 (d, J=10.2 Hz, 1H), 4.80 (d, J=10.2 Hz, 1H), 5.09 (s, 1H), 6.79 (br s, 2H), 7.32-7.37 (m, 3H), 7.41-7.46 (m, 2H), 7.64 (dd, J=8.8, 2.8 Hz, 1H), 7.96 (d, J=8.8 Hz, 1H), 8.45 (d, J=2.8 Hz, 1H). LC-MS [M+H]$^+$ m/z 446.1 (calcd $C_{20}H_{23}FN_5O_4S$, 445.14).

Step 2: Synthesis of (2S,5R)-6-hydroxy-N-((5-methoxypyridin-2yl)sulfonyl)-7-oxo-1,6-diazabicyclo[3.2.1]octane-2-carboximidamide (2_22_2)

10% Pd/C (dry, 318 mg) was added to a solution of compound 2_22_1 (277 mg, 0.60 mmol) in THF (5 mL) with two drops of TEA. The reaction mixture was stirred under H$_2$ (balloon) at room temperature for 3 hours, filtered through a pad of celite, rinsed with EtOAc. The filtrate was concentrated to give the title compound 2_22_2 (170 mg, 80%) as an oil, which was directly used for next step without further purification. $^1$H NMR (400 MHz, DMSO-$d_6$): δ 1.74-1.83 (m, 2H), 1.90-1.99 (m, 1H), 2.04-2.11 (m, 1H), 3.04 (t, J=11.5 Hz, 1H), 3.80 (dd, J=11.5, 4.3 Hz, 1H), 3.99 (s, 3H), 4.00-4.07 (m, 1H), 5.14 (s, 1H), 6.52 (s, 2H), 7.71 (dd, J=8.8, 2.8 Hz, 1H), 8.03 (d, J=8.8 Hz, 1H), 8.54 (d, J=2.8 Hz, 1H), 9.31 (s, 1H). LC-MS [M+Na]$^+$ m/z 378.1 (calcd for $C_{13}H_{17}N_5O_5S$, 355.09).

Step 3: Synthesis of (2S,5R)-2-(N-((5-methoxypyridin-2-yl)sulfonyl)carbamimidoyl)-7-oxo-1,6-diazabicyclo[3.2.1]octan-6-yl hydrogen sulfate (Example 22)

A mixture of compound 2_22_2 (170 mg, 0.48 mmol), $SO_3$-pyridine (228 mg, 1.44 mmol) in pyridine (5 mL) was stirred at room temperature overnight. The reaction mixture was concentrated to give a residue, which was purified by resin Dowex-50wx $Na^+$ exchange using water as elution solvent and lyophilized, followed by preparative HPLC on an Agilent 10 prep-C18 250×21.2 mm column and lyophilized to afford example 22 (30 mg, 14%) as a white solid. $^1$H NMR (400 MHz, $D_2O$): δ 1.77-1.90 (m, 3H), 1.97-2.04 (m, 1H), 2.99 (t, J=11.5 Hz, 1H), 3.82 (s, 3H), 3.86 (d, J=11.5 Hz, 1H), 3.90-3.98 (m, 1H), 4.99 (s, 1H), 7.49 (d, J=8.8 Hz, 1H), 7.93 (d, J=8.8 Hz, 1H), 8.25 (s, 1H). LC-MS [M−H]⁻ m/z 434.1 (calcd for $C_{13}H_{17}N_5O_8S_2$, 435.05).

Example 23

(2S,5R)-2-(N-((5-fluoropyridin-2-yl)sulfonyl)carbamimidoyl)-7-oxo-1,6-diazabicyclo[3.2.1]octan-6-yl hydrogen sulfate (Compound 106 in Table 1)

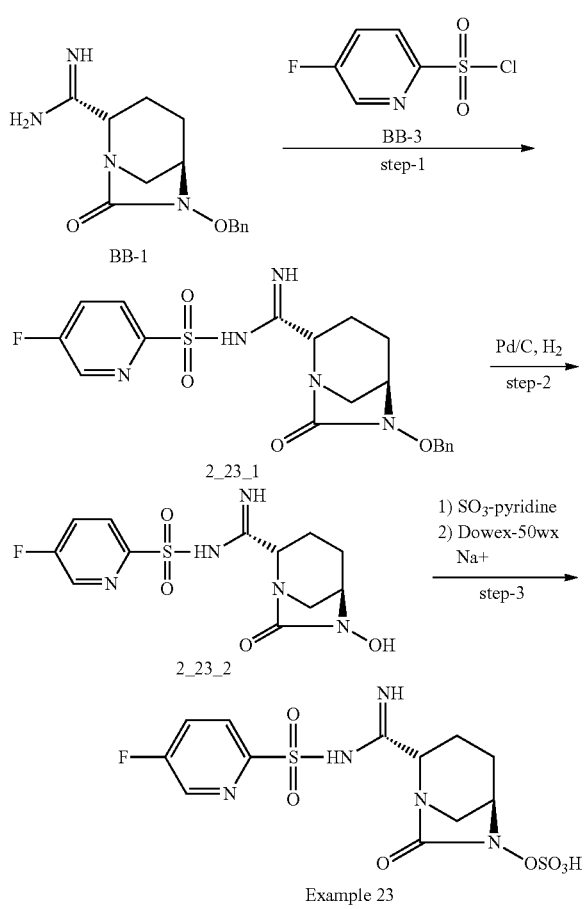

Example 23

Step-1: Synthesis of (2S,5R)-6-(benzyloxy)-N-((5-fluoropyridin-2-yl)sulfonyl)-7-oxo-1,6-diazabicyclo[3.2.1]octane-2-carboximidamide (2_23_1)

5-Fluoropyridine-2-sulfonyl chloride (BB-3, 234 mg, 1.2 mmol) and TEA (0.26 mL, 1.8 mmol) were added to a solution of BB-1 (164 mg, 0.6 mmol) in $CH_2Cl_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_23_1 (237 mg, 91%) as a white foam. $^1$H NMR (400 MHz, DMSO-$d_6$): δ 1.95-1.96 (m, 3H), 1.99-2.05 (m, 1H), 2.97 (t, J=11.6 Hz, 1H), 3.79 (dd, J=11.6, 3.7 Hz, 1H), 3.92-4.01 (m, 1H), 4.79 (s, 2H), 5.10 (s, 1H), 6.80 (br s, 2H), 7.32-7.37 (m, 3H), 7.41-7.46 (m, 2H), 8.06-8.51 (m, 2H), 8.83 (d, J=2.3 Hz, 1H). $^{19}$F NMR (376 MHz, DMSO-$d_6$): δ −118.93 (dd, J=8.2, 5.4 Hz, 1F). LC-MS [M+H]⁺ m/z 434.1 (calcd $C_{13}H_{20}FN_5O_4S$, 433.12).

Step 2: Synthesis of (2S,5R)—N-((5-fluoropyridin-2-yl)sulfonyl)-6-hydroxy-7-oxo-1,6-diazabicyclo[3.2.1]octane-2-carboximidamide (2_23_2)

10% Pd/C (wet, 45 mg) was added to a solution of compound 2_23_1 (222 mg, 0.51 mmol) in THF (5 mL) with two drops of TEA. The reaction mixture was stirred under $H_2$ (balloon) at room temperature for 3 hours, filtered through a pad of celite, rinsed with EtOAc. The filtrate was concentrated to give the title compound 2_23_2 (170 mg, 97%) as an oil, which was directly used for next step without further purification. $^1$H NMR (400 MHz, DMSO-$d_6$): δ 1.75-1.84 (m, 2H), 1.92-2.02 (m, 1H), 2.05-2.11 (m, 1H), 3.06 (t, J=11.7 Hz, 1H), 3.83 (dd, J=11.7, 4.0 Hz, 1H), 4.01-4.09 (m, 1H), 5.19 (s, 1H), 6.54 (br s, 2H), 8.12-8.21 (m, 2H), 8.92 (s, 1H), 9.34 (s, 1H). $^{19}$F NMR (376 MHz, DMSO-$d_6$): δ −119.09 (dd, J=8.2, 4.1 Hz, 1F). LC-MS [M+Na]⁺ m/z 366.1 (calcd for $C_{12}H_{14}FN_5O_4S$, 343.07).

Step 3: Synthesis of (2S,5R)-2-(N-((5-fluoropyridin-2-yl)sulfonyl)carbamimidoyl)-7-oxo-1,6-diazabicyclo[3.2.1]octan-6-yl hydrogen sulfate (Example 23)

A mixture of compound 2_23_2 (200 mg, 0.58 mmol), $SO_3$-pyridine (286 mg, 1.8 mmol) in pyridine (5 mL) was stirred at room temperature overnight. The reaction mixture was concentrated to give a residue, which was purified by resin Dowex-50wx $Na^+$ exchange using water as elution solvent and lyophilized, followed by preparative HPLC on an Agilent 10 prep-C18 250×21.2 mm column and lyophilized to afford example 23 (27 mg, 11%) as a white solid. $^1$H NMR (400 MHz, $D_2O$): δ 1.79-1.90 (m, 3H), 1.97-2.03 (m, 1H), 3.02 (t, J=11.5 Hz, 1H), 3.84-3.98 (m, 2H), 5.02 (s, 1H), 7.76 (t, J=8.4 Hz, 1H), 8.04 (dd, J=8.7, 3.8 Hz, 1H), 8.49 (s, 1H). $^{19}$F NMR (376 MHz, $D_2O$): δ −117.03 (dd, J=7.1, 4.1 Hz, 1F). LC-MS [M−H]⁻ 422.0 (calcd for $C_{12}H_{14}FN_5O_7S_2$, 423.03).

Example 24

(2S,5R)-7-oxo-2-(N-(pyrazin-2-ylsulfonyl)carbamimidoyl)-1,6-diazabicyclo[3.2.1]octan-6-yl hydrogen sulfate (Compound 107 in Table 1)

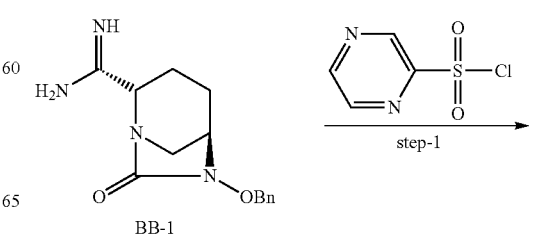

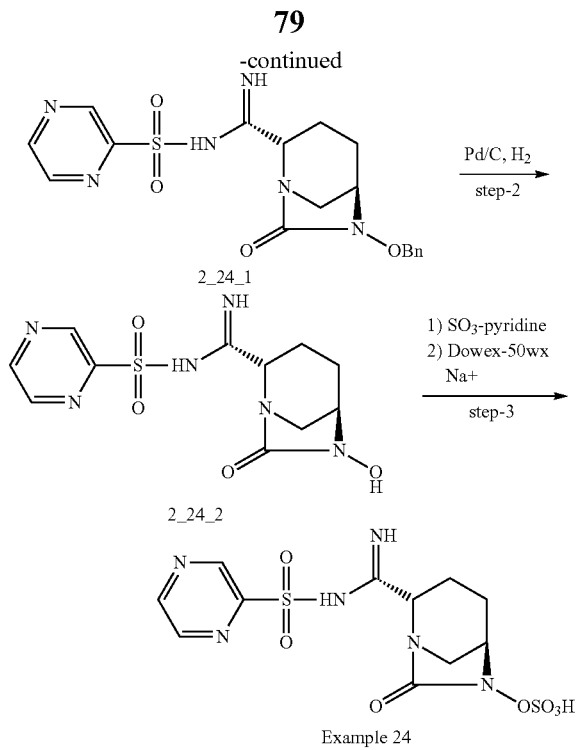

Example 24

Step-1: Synthesis of (2S,5R)-6-(benzyloxy)-7-oxo-N-(pyrazin-2-ylsulfonyl)-1,6-diazabicyclo[3.2.1]octane-2-carboximidamide (2_24_1)

Pyrazine-2-sulfonyl chloride (213 mg, 1.2 mmol) and TEA (0.26 mL, 1.8 mmol) were added to a solution of BB-1 (164 mg, 0.6 mmol) in $CH_2Cl_2$ (5 mL) at 0° C., and then stirred overnight at room temperature. The reaction mixture was concentrated to give a residue, which was purified by silica gel column chromatography eluting with 50% ethyl acetate in petroleum ether to give the title compound 2_24_1 (248 mg, 99%) as a white foam. $^1H$ NMR (400 MHz, DMSO-$d_6$): δ 1.96-1.96 (m, 3H), 2.00-2.06 (m, 1H), 2.98 (t, J=11.7 Hz, 1H), 3.82 (dd, J=11.7, 4.1 Hz, 1H), 3.92-4.01 (m, 1H), 4.79 (s, 2H), 5.21 (s, 1H), 6.79 (br s, 2H), 7.32-7.36 (m, 3H), 7.40-7.45 (m, 2H), 8.92 (dd, J=8.9, 1.4 Hz, 1H), 9.05 (d, J=2.4 Hz, 1H), 9.21 (d, J=1.4 Hz, 1H). LC-MS $[M+H]^+$ m/z 417.1 (calcd $C_{18}H_{20}N_6O_4S$, 416.12).

Step 2: Synthesis of (2S,5R)-6-hydroxy-7-oxo-N-(pyrazin-2-ylsulfonyl)-1,6-diazabicyclo[3.2.1]octane-2-carboximidamide (2_24_2)

10% Pd/C (dry, 191 mg) was added to a solution of compound 2_24_1 (250 mg, 0.60 mmol) in THF (5 mL) with two drops of TEA. The reaction mixture was stirred under $H_2$ (balloon) at room temperature for 3 hours, filtered through a pad of celite, rinsed with EtOAc. The filtrate was concentrated to give the title compound 2_24_2 (190 mg, not pure) as an oil, which was directly used for next step without further purification. LC-MS $[M+Na]^+$ m/z 349.1 (calcd for $C_{11}H_{14}N_6O_4S$, 326.07).

Step 3: Synthesis of (2S,5R)-7-oxo-2-(N-(pyrazin-2-ylsulfonyl)carbamimidoyl)-1,6-diazabicyclo[3.2.1]octan-6-yl hydrogen sulfate (Example 24)

A mixture of compound 2_24_2 (190 mg obtained above), $SO_3$-pyridine (120 mg, 0.75 mmol) in pyridine (5 mL) was stirred at room temperature overnight. The reaction mixture was concentrated to give a residue, which was purified by resin Dowex-50wx $Na^+$ exchange using water as elution solvent and lyophilized, followed by preparative HPLC on an Agilent 10 prep-C18 250×21.2 mm column and lyophilized to afford example 24 (10 mg, 4%) as a white solid. $^1H$ NMR (400 MHz, $D_2O$): δ 1.83-1.94 (m, 3H), 2.02-2.07 (m, 1H), 3.12 (t, J=11.9 Hz, 1H), 3.92-4.01 (m, 2H), 5.12 (s, 1H), 8.75 (dd, J=2.4, 1.4 Hz, 1H), 8.82 (d, J=2.4 Hz, 1H), 9.11 (d, J=1.4, 1H). LC-MS $[M-H]^-$ 405.0 (calcd for $C_{11}H_{14}N_6O_7S_2$, 406.03).

PHARMACOLOGICAL METHODS

Antibacterial Activity and Synergistic Activity

Compounds of the present invention alone, avibactam (AVI) alone, relebactam (REL) alone, meropenem (MER) alone, imipenem (IMI) alone, and as a combination of compounds of the present invention, or avibactam or relebactam with test antibiotic (meropenem or imipenem) was tested for antimicrobial activity by determining minimum inhibitory concentration (MIC, mg/L) using the broth microdilution method according to the guidelines of the Clinical Laboratories and Standards Institute ("Methods for Dilution Antimicrobial Susceptibility Tests for Bacterial that Grow Aerobically", Approved standard, 7th ed., Clinical and Laboratories Standards Institute (CLSI) Document M7-A8, Wayne, Pa., USA, 2009). Meropenem or imipenem as a test antibiotic compound was dissolved in DMSO, and then diluted in microbial growth medium (Mueller-Hinton Broth II, cation adjusted) resulting in a final concentration range of 0.031-64 mg/L in serial two-fold dilution. In all cases the final DMSO concentration was less than 0.5%. Bacteria were added to 96-well microtitre plates containing the serial two-fold dilutions of the compounds; the final cell density was approximately $5×10^5$ colony forming units/mL (CFU/mL). Plates were incubated at 37° C. for 18-24 hours and read visually. The MIC, i.e. the lowest concentration of the test compound that inhibited visible growth of the bacteria, was recorded. The same assay conditions were used when the compounds of present invention alone, avibactam or relebactam alone (as a control), and as a combination of the present invention each compound, or avibactam or relebactam with test meropenem or imipenem antibiotic compound was tested for minimum inhibitory concentration (MIC, mg/L). While test meropenem or imipenem was serially diluted as described above, a constant concentration of avibactam, or relebactam or the present invention each compound of 4 mg/L was used.

The antimicrobial activity by determining minimum inhibitory concentration (MIC, mg/L) against bacteria listed in table 2, table 3 and table 4.

Bacterial strains that were used to evaluate the antimicrobial activity using the MIC determination included but were not limited to E. coli clinical isolate (strain 1, TEM-1), E. coli 8739 (strain 2, CTX-M15), K. pneumoniae clinical isolate (strain 3, SHV-1), K. pneumoniae 700603 (strain 4, KPC-3, TEM-1), E. cloacae clinical isolate (strain 5, P99), E. cloacae 700323 (strain 6, AmpC), A. baumannii clinical isolate (strain 7, OXA-23, OXA-40), A. baumannii 19606 (strain 8, OXA-24), P. aeruginosa clinical isolate (strain 9, KPC-2), P. aeruginosa 9027 (strain 10, AmpC).

TABLE 2

Synergy of the inhibitor example 1 to example 24 (4 mg/L) in combination with meropenem (MER, AVI, REL and Ex. 1 to Ex. 4, MIC, mg/L)

| Organism | MER Alone | MER + AVI | MER + REL | MER + Ex. 1 | MER + Ex. 2 | MER + Ex. 3 | MER + Ex. 4 |
|---|---|---|---|---|---|---|---|
| strain 1 (TEM-1) | 4.0 | <0.125 | <0.031 | <0.125 | <0.125 | <0.125 | <0.125 |
| strain 2 (CTX-M15) | 4.0 | <0.125 | <0.031 | <0.125 | <0.125 | <0.125 | <0.125 |
| strain 3 (SHV-1) | 4.0 | 0.25 | <0.031 | 0.125 | 0.125 | 0.25 | <0.125 |
| strain 4 (KPC-3, TEM-1) | 2.0 | <0.125 | <0.031 | <0.125 | <0.125 | <0.125 | <0.125 |
| strain 5 (P99) | 4.0 | 0.5 | <0.031 | <0.125 | <0.125 | 0.25 | 0.25 |
| strain 6 (AmpC) | 4.0 | <0.125 | <0.031 | <0.125 | <0.125 | <0.125 | <0.125 |
| strain 7 (OXA-23/40) | 4.0 | 0.25 | 0.125 | <0.125 | <0.125 | 0.25 | <0.125 |
| strain 8 (OXA-24) | 2.0 | 0.5 | 0.5 | 0.5 | 0.5 | 0.5 | 0.5 |
| strain 9 (KPC-2) | 4.0 | 0.5 | 0.5 | 0.125 | 0.125 | 0.5 | 1.0 |
| strain 10 (AmpC) | 4.0 | <0.125 | 0.0625 | 0.125 | <0.125 | <0.125 | <0.125 |

Synergy of the inhibitor example 1 to example 24 (4 mg/L) in combination with meropenem (Ex. 5 to Ex. 10, MIC, mg/L)

| Organism | MER + Ex 5 | MER + Ex. 6 | MER + Ex. 7 | MER + Ex. 8 | MER + Ex. 9 | MER + Ex. 10 |
|---|---|---|---|---|---|---|
| strain 1 (TEM-1) | <0.125 | <0.125 | <0.125 | 0.25 | <0.031 | 0.0625 |
| strain 2 (CTX-M15) | <0.125 | <0.125 | <0.125 | <0.125 | 0.0625 | 0.125 |
| strain 3 (SHV-1) | <0.125 | 0.25 | 0.25 | 0.5 | <0.031 | <0.031 |
| strain 4 (KPC-3, TEM-1) | <0.125 | <0.125 | <0.125 | <0.125 | <0.031 | <0.031 |
| strain 5 (P99) | <0.125 | <0.125 | <0.125 | 1.0 | 0.0625 | 0.125 |
| strain 6 (AmpC) | <0.125 | <0.125 | <0.125 | <0.125 | <0.031 | <0.031 |
| strain 7 (OXA-23/40) | <0.125 | <0.125 | <0.125 | 0.25 | 0.125 | 0.125 |
| strain 8 (OXA-24) | 0.5 | 1.0 | 0.5 | 0.5 | 1.0 | 0.5 |
| strain 9 (KPC-2) | <0.125 | 0.5 | 0.5 | 1.0 | 0.5 | 0.5 |
| strain 10 (AmpC) | <0.125 | <0.125 | <0.125 | 0.125 | 0.062 | 0.125 |

Synergy of the inhibitor example 1 to example 24 (4 mg/L) in combination with meropenem (Ex. 11 to Ex. 16, MIC, mg/L)

| Organism | MER + Ex 11 | MER + Ex. 12 | MER + Ex. 13 | MER + Ex. 14 | MER + Ex. 15 | MER + Ex. 16 |
|---|---|---|---|---|---|---|
| strain 1 (TEM-1) | <0.031 | <0.031 | 0.0625 | <0.031 | <0.031 | <0.031 |
| strain 2 (CTX-M15) | 0.125 | <0.031 | 0.0625 | <0.031 | <0.031 | <0.031 |
| strain 3 (SHV-1) | <0.031 | <0.031 | <0.031 | <0.031 | <0.031 | <0.031 |
| strain 4 (KPC-3, TEM-1) | <0.031 | <0.031 | <0.031 | <0.031 | <0.031 | <0.031 |
| strain 5 (P99) | 0.125 | 0.0625 | 0.125 | 0.0625 | 0.0625 | 0.0625 |
| strain 6 (AmpC) | <0.031 | <0.031 | <0.031 | <0.031 | <0.031 | <0.031 |
| strain 7 (OXA-23/40) | 0.125 | 0.0625 | 0.0625 | 0.125 | 0.125 | 0.125 |

TABLE 2-continued

| | | | | | | |
|---|---|---|---|---|---|---|
| strain 8 (OXA-24) | 0.5 | 0.125 | 0.5 | 0.25 | 0.5 | 0.5 |
| strain 9 (KPC-2) | 1.0 | 0.5 | 0.5 | 0.5 | 0.25 | 0.25 |
| strain 10 (AmpC) | 0.25 | 0.125 | 0.125 | 0.062 | 0.125 | 0.0625 |

Synergy of the inhibitor example 1 to example 24 (4 mg/L) in combination with meropenem (Ex. 17 to Ex. 22, MIC, mg/L)

| Organism | MER + Ex 17 | MER + Ex. 18 | MER + Ex. 19 | MER + Ex. 20 | MER + Ex. 21 | MER + Ex. 22 |
|---|---|---|---|---|---|---|
| strain 1 (TEM-1) | <0.031 | 0.0625 | 0.0625 | 0.5 | <0.031 | <0.031 |
| strain 2 (CTX-M15) | 0.125 | <0.031 | <0.031 | 0.5 | <0.031 | <0.031 |
| strain 3 (SHV-1) | <0.031 | 0.0625 | 0.0625 | 4.0 | 0.0625 | 0.0625 |
| strain 4 (KPC-3, TEM-1) | <0.031 | 0.0625 | 0.0625 | 0.5 | <0.031 | <0.031 |
| strain 5 (P99) | 0.0625 | 0.125 | 0.0625 | 4.0 | 0.0625 | 0.0625 |
| strain 6 (AmpC) | <0.031 | <0.031 | <0.031 | 0.25 | <0.031 | <0.031 |
| strain 7 (OXA-23/40) | 0.125 | 0.5 | 0.25 | 0.5 | 0.25 | 0.25 |
| strain 8 (OXA-24) | 0.5 | 1.0 | 0.25 | 1.0 | 2.0 | 1.0 |
| strain 9 (KPC-2) | 0.5 | 2.0 | 2.0 | 4.0 | 1.0 | 1.0 |
| strain 10 (AmpC) | 0.25 | 1.0 | 0.25 | 4.0 | 0.25 | 0.25 |

Synergy of the inhibitor example 1 to example 24 (4 mg/L) in combination with meropenem (Ex. 23 to Ex. 24, MIC, mg/L)

| Organism | MER + Ex 23 | MER + Ex. 24 |
|---|---|---|
| strain 1 (TEM-1) | 0.0625 | 0.0625 |
| strain 2 (CTX-M15) | <0.031 | <0.031 |
| strain 3 (SHV-1) | 0.0625 | 0.0625 |
| strain 4 (KPC-3, TEM-1) | 0.0625 | <0.031 |
| strain 5 (P99) | 0.0625 | 0.0625 |
| strain 6 (AmpC) | 0.0625 | <0.031 |
| strain 7 (OXA-23/40) | 0.5 | 0.25 |
| strain 8 (OXA-24) | 2.0 | 0.5 |
| strain 9 (KPC-2) | 2.0 | 0.25 |
| strain 10 (AmpC) | 0.25 | 0.25 |

TABLE 3

Synergy of the inhibitor example 1 to example 24 (4 mg/L) in combination with imipenem (IMI, AVI, REL and Ex. 1 to Ex. 4, MIC, mg/L)

| Organism | IMI Alone | IMI + AVI | IMI + REL | IMI + Ex. 1 | IMI + Ex. 2 | IM + Ex. 3 | IMI + Ex. 4 |
|---|---|---|---|---|---|---|---|
| strain 1 (TEM-1) | 0.50 | 0.125 | 0.125 | 0.125 | <0.125 | <0.125 | 0.5 |
| strain 2 (CTX-M15) | 0.50 | 0.0625 | 0.125 | 0.0625 | <0.125 | <0.125 | <0.125 |
| strain 3 (SHV-1) | 2.0 | 1.0 | 0.5 | 0.25 | 0.25 | 0.25 | 0.25 |
| strain 4 (KPC-3, TEM-1) | 4.0 | 0.125 | 0.25 | 0.25 | <0.125 | <0.125 | <0.125 |
| strain 5 (P99) | 4.0 | 0.25 | 0.125 | 1 | <0.125 | 0.25 | 0.5 |

TABLE 3-continued

| | | | | | | | |
|---|---|---|---|---|---|---|---|
| strain 6 (AmpC) | 0.5 | 0.125 | 0.125 | 0.0625 | 0.5 | <0.125 | <0.125 |
| strain 7 (OXA-23/40) | 0.5 | 0.125 | 0.125 | 0.0625 | 0.25 | 0.25 | 0.5 |
| strain 8 (OXA-24) | 2.0 | 0.125 | 0.125 | 0.062 | <0.125 | 0.5 | 0.5 |
| strain 9 (KPC-2) | 2.0 | 0.25 | 0.25 | 0.25 | 1.0 | 0.5 | 1.0 |
| strain 10 (AmpC) | 4.0 | 0.25 | 0.25 | 0.5 | 1.0 | 0.125 | 1.0 |

Synergy of the inhibitor example 1 to example 24 (4 mg/L) in combination with imipenem (Ex. 5 to Ex. 10, MIC, mg/L)

| Organism | IMI + Ex 5 | IMI + Ex. 6 | IMI + Ex. 7 | IMI + Ex. 8 | IMI + Ex. 9 | IMI + Ex. 10 |
|---|---|---|---|---|---|---|
| strain 1 (TEM-1) | <0.125 | <0.125 | <0.125 | 0.5 | 0.25 | 0.125 |
| strain 2 (CTX-M15) | <0.125 | <0.125 | <0.125 | <0.125 | 0.125 | 0.0625 |
| strain 3 (SHV-1) | <0.125 | 0.25 | 0.5 | 0.5 | 0.5 | 0.5 |
| strain 4 (KPC-3, TEM-1) | <0.125 | <0.125 | <0.125 | <0.125 | 1.0 | 0.5 |
| strain 5 (P99) | 0.25 | 1.0 | 0.5 | 0.5 | 1.0 | 1.0 |
| strain 6 (AmpC) | <0.125 | <0.125 | <0.125 | <0.125 | 0.125 | 0.0625 |
| strain 7 (OXA-23/40) | 0.5 | 0.5 | 0.5 | 0.5 | 0.25 | 0.125 |
| strain 8 (OXA-24) | 0.5 | 0.5 | 0.5 | 0.5 | 0.125 | 0.0625 |
| strain 9 (KPC-2) | 0.5 | 0.5 | 0.5 | 1.0 | 1.0 | 1.0 |
| strain 10 (AmpC) | 0.5 | 1.0 | 1.0 | 0.5 | 1.0 | 0.5 |

Synergy of the inhibitor example 1 to example 24 (4 mg/L) in combination with imipenem (Ex. 11 to Ex. 16, MIC, mg/L)

| Organism | IMI + Ex 11 | IMI + Ex. 12 | IMI + Ex. 13 | IMI + Ex. 14 | IMI + Ex. 15 | IMI + Ex. 16 |
|---|---|---|---|---|---|---|
| strain 1 (TEM-1) | 0.125 | <0.031 | 0.062 | 0.25 | 0.125 | 0.125 |
| strain 2 (CTX-M15) | 0.25 | 0.25 | 0.0625 | 0.25 | 0.125 | 0.0625 |
| strain 3 (SHV-1) | 0.25 | <0.031 | 0.125 | 0.5 | 0.5 | 0.5 |
| strain 4 (KPC-3, TEM-1) | 0.0625 | <0.031 | 0.0625 | 0.125 | 0.125 | 0.25 |
| strain 5 (P99) | 0.5 | <0.031 | 0.5 | 2.0 | 0.5 | 0.5 |
| strain 6 (AmpC) | 0.0625 | <0.031 | <0.031 | 0.125 | 0.125 | 0.125 |
| strain 7 (OXA-23/40) | 0.125 | 0.5 | 0.125 | 0.25 | 0.125 | 0.125 |
| strain 8 (OXA-24) | 0.125 | <0.031 | 0.0625 | 0.125 | 0.25 | 0.125 |
| strain 9 (KPC-2) | 0.5 | 0.5 | 0.5 | 1.0 | 0.5 | 0.5 |
| strain 10 (AmpC) | 0.5 | 1.0 | 1.0 | 1.0 | 1.0 | 1.0 |

Synergy of the inhibitor example 1 to example 24 (4 mg/L) in combination with imipenem (Ex. 17 to Ex. 22, MIC, mg/L)

| Organism | IMI + Ex 17 | IMI + Ex. 18 | IMI + Ex. 19 | IMI + Ex. 20 | IMI + Ex. 21 | IMI + Ex. 22 |
|---|---|---|---|---|---|---|
| strain 1 (TEM-1) | 0.125 | 0.5 | 0.5 | 0.5 | 0.5 | 0.5 |
| strain 2 (CTX-M15) | 0.125 | 0.5 | 0.5 | 0.5 | 0.25 | 1.0 |
| strain 3 (SHV-1) | 0.5 | 2.0 | 2.0 | 4.0 | 1.0 | 1.0 |
| strain 4 (KPC-3, TEM-1) | 0.5 | 0.5 | 2.0 | 0.5 | 0.5 | 0.5 |
| strain 5 (P99) | 0.5 | 1.0 | 2.0 | 4.0 | 1.0 | 1.0 |
| strain 6 (AmpC) | 0.0625 | 0.25 | 0.5 | 0.25 | 0.5 | 0.25 |

TABLE 3-continued

| | | | | | | |
|---|---|---|---|---|---|---|
| strain 7 (OXA-23/40) | 0.125 | 0.5 | 0.5 | 0.5 | 0.5 | 0.5 |
| strain 8 (OXA-24) | 0.25 | 1.0 | 1.0 | 1.0 | 0.5 | 0.5 |
| strain 9 (KPC-2) | 0.5 | 2.0 | 2.0 | 2.0 | 2.0 | 2.0 |
| strain 10 (AmpC) | 1.0 | 4.0 | 4.0 | 4.0 | 2.0 | 4.0 |

Synergy of the inhibitor example 1 to example 24 (4 mg/L) in combination with imipenem (Ex. 23 to Ex. 24, MIC, mg/L)

| Organism | IMI + Ex 23 | IMI + Ex. 24 |
|---|---|---|
| strain 1 (TEM-1) | 0.5 | 0.5 |
| strain 2 (CTX-M15) | 0.5 | 0.25 |
| strain 3 (SHV-1) | 2.0 | 1.0 |
| strain 4 (KPC-3, TEM-1) | 2.0 | 0.25 |
| strain 5 (P99) | 4.0 | 1.0 |
| strain 6 (AmpC) | 0.5 | 0.25 |
| strain 7 (OXA-23/40) | 0.5 | 0.5 |
| strain 8 (OXA-24) | 1.0 | 0.5 |
| strain 9 (KPC-2) | 2.0 | 2.0 |
| strain 10 (AmpC) | 4.0 | 4.0 |

TABLE 4

Antibacterial activity of example 1 to example 24 (AVI, REL and Ex. 1 to 6, MIC, mg/L)

| Organism | AVI | REL | Ex. 1 Alone | Ex. 3 Alone | Ex. 4 Alone | Ex. 5 Alone | Ex. 6 Alone |
|---|---|---|---|---|---|---|---|
| strain 1 (TEM-1) | >64 | >64 | >64 | >64 | >64 | >64 | >64 |
| strain 2 (CTX-M15) | >64 | >64 | >64 | >64 | >64 | >64 | >64 |
| strain 3 (SHV-1) | >64 | >64 | >64 | >64 | >64 | >64 | >64 |
| strain 4 (KPC-3, TEM-1) | >64 | >64 | >64 | >64 | >64 | >64 | >64 |
| strain 5 (P99) | >64 | >64 | >64 | >64 | >64 | >64 | >64 |
| strain 6 (AmpC) | >64 | >64 | >64 | >64 | >64 | >64 | >64 |
| strain 7 (OXA-23/40) | >64 | >64 | >64 | >64 | >64 | >64 | >64 |
| strain 8 (OXA-24) | >64 | >64 | >64 | >64 | >64 | >64 | >64 |
| strain 9 (KPC-2) | >64 | >64 | >64 | >64 | >64 | >64 | >64 |
| strain 10 (AmpC) | >64 | >64 | >64 | >64 | >64 | >64 | >64 |

Antibacterial activity of example 1 to example 24 (Ex. 7 to 15, MIC, mg/L)

| Organism | Ex. 7 Alone | Ex. 8 Alone | Ex. 9 Alone | Ex. 12 Alone | Ex. 13 Alone | Ex. 14 Alone | Ex. 15 Alone |
|---|---|---|---|---|---|---|---|
| strain 1 (TEM-1) | >64 | >64 | >64 | >64 | >64 | >64 | >64 |
| strain 2 (CTX-M15) | >64 | >64 | >64 | >64 | >64 | >64 | >64 |
| strain 3 (SHV-1) | >64 | >64 | >64 | >64 | >64 | >64 | >64 |
| strain 4 (KPC-3, TEM-1) | >64 | >64 | >64 | >64 | >64 | >64 | >64 |

TABLE 4-continued

| | | | | | | | |
|---|---|---|---|---|---|---|---|
| strain 5 (P99) | >64 | >64 | >64 | >64 | >64 | >64 | >64 |
| strain 6 (AmpC) | >64 | >64 | >64 | >64 | >64 | >64 | >64 |
| strain 7 (OXA-23/40) | >64 | >64 | >64 | >64 | >64 | >64 | >64 |
| strain 8 (OXA-24) | >64 | >64 | >64 | >64 | >64 | >64 | >64 |
| strain 9 (KPC-2) | Ex.7 Alone | >64 | >64 | >64 | >64 | >64 | >64 |
| strain 10 (AmpC) | >64 | >64 | >64 | >64 | >64 | >64 | >64 |

Antibacterial activity of example 1 to example 24 (Ex. 16 to 22, MIC, mg/L)

| Organism | Ex. 16 Alone | Ex. 17 Alone | Ex. 18 Alone | Ex. 19 Alone | Ex. 20 Alone | Ex. 21 Alone | Ex. 22 Alone |
|---|---|---|---|---|---|---|---|
| strain 1 (TEM-1) | >64 | >64 | >64 | >64 | >64 | >64 | >64 |
| strain 2 (CTX-M15) | >64 | >64 | >64 | >64 | >64 | >64 | >64 |
| strain 3 (SHV-1) | >64 | >64 | >64 | >64 | >64 | >64 | >64 |
| strain 4 (KPC-3, TEM-1) | >64 | >64 | >64 | >64 | >64 | >64 | >64 |
| strain 5 (P99) | >64 | >64 | >64 | >64 | >64 | >64 | >64 |
| strain 6 (AmpC) | >64 | >64 | >64 | >64 | >64 | >64 | >64 |
| strain 7 (OXA-23/40) | >64 | >64 | >64 | >64 | >64 | >64 | >64 |
| strain 8 (OXA-24) | >64 | >64 | >64 | >64 | >64 | >64 | >64 |
| strain 9 (KPC-2) | >64 | >64 | >64 | >64 | >64 | >64 | >64 |
| strain 10 (AmpC) | >64 | >64 | >64 | >64 | >64 | >64 | >64 |

Antibacterial activity of example 1 to example 24 (Ex. 23 to 24, MIC, mg/L)

| Organism | Ex. 23 Alone | Ex. 24 Alone |
|---|---|---|
| strain 1 (TEM-1) | >64 | >64 |
| strain 2 (CTX-M15) | >64 | >64 |
| strain 3 (SHV-1) | >64 | >64 |
| strain 4 (KPC-3, TEM-1) | >64 | >64 |
| strain 5 (P99) | >64 | >64 |
| strain 6 (AmpC) | >64 | >64 |
| strain 7 (OXA-23/40) | >64 | >64 |
| strain 8 (OXA-24) | >64 | >64 |
| strain 9 (KPC-2) | >64 | >64 |
| strain 10 (AmpC) | >64 | >64 |

Test for Lactamase Inhibitory Activity

The inhibitory activities of present compounds against various enzymes are measured by spectrophotometric assay using 490 nM and using nitrocefin as a substrate [J. Antimicrob. Chemother., 28, pp 775-776 (1991)]. The concentration of inhibitor ($IC_{50}$) which inhibits by 50% the reaction of hydrolysis of nitrocefin by the enzyme is determined.

In light of the data described herein, persons of skill in the art would expect that all of the compounds within the scope of formula (I), salts of such compounds, solvates of such compounds, and salts thereof, and deuterated compounds of all such compounds, salts and solvates (i.e., compounds of formula (I) modified in that they have been deuterated, salts of compounds of formula (I) modified in that they have been deuterated, and solvates of compounds of formula (I) modified in that they have been deuterated) would be effective on their own as antibacterial compounds, and in combination with ß-lactam antibiotics.

Efficacy of the ß-lactamase inhibitors can be evaluated in combination with ceftazidime aztreonam, meropenem, imipenem and other class of carbapenems and cephalosporins in murine infection models such as septicemia, pneumonia and thigh infection models (Ref: Andrea Endimiani et. al. *Antimicrobial Agents and Chemotherapy*, January 2011, page 82-85). For murine acute lethal septicemia model, mice were infected by the intraperitoneal injection of the clinical strains resulting in death of the untreated controls within 24-48 hours. In particular, a fresh predetermined bacterial inoculum of approximately $3.3 \times 10^5$ to $3.6 \times 10^5$ CFU in 5% hog gastric mucin grown overnight. Thirty minutes post infection, a single subcutaneous dose of meropenem with and without ß-lactamase inhibitor was initiated and the survival ratio monitored for 5 days twice daily. For each strain tested, the dosing regimen used are meropenem alone (doses of 512, 1024 & 2048 mg/kg of body weight) and meropenem plus ß-lactamase inhibitor at ratio of 2:1, 4:1, 8:1, 16:1 & 32:1 (meropenem doses were 4, 8, 16, 32 & 64 mg/kg for each ratio). The median effective dose for 50% protective dose ($ED_{50}$) of animals was determined by a computerized program of Probit analysis. Survival rates stratified for different dosing regimen were also obtained. For experimental pneumoniae model, immunocompromised mice were used and intratracheally infected with *Klebsiella pneumoniae* strains. Mice in this model developed bacteraemia pneumoniae and fatal disease within 2 to 4 days with lung bacterial burden at 16-18 hours post infection of $10^{11}$ to $10^{13}$ CFU/gm lung. Treatment with meropenem and inhibitor at a ratio of 2/1 & 4/1 demonstrated efficacy with significant 3 to 6 log reduction in lung counts compared to meropenem alone and was relevant to the clinical situation. Human testing of the ß-lactamase inhibitor can be conducted in combination with partner antibiotic at a set ratio utilizing standard clinical development practice.

What we claim is:

1. A compound of formula (I):

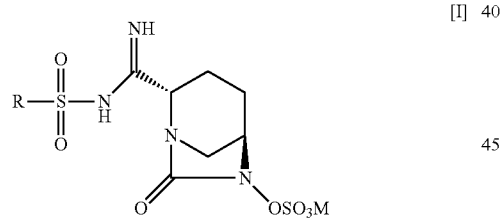

[I]

wherein:

M is hydrogen or a pharmaceutically acceptable salt forming cation,

R is a radical selected from any of the following groups:
(1) $C_{1-6}$ straight or branched chain alkyl or amino which is optionally substituted;
(2) $C_{3-6}$ cycloalkyl or heterocycle which is optionally substituted;
(3) $C_{5-6}$ membered aryl or heteroaryl which is optionally substituted;
(4) amine or substituted-amine which is optionally substituted;
or a deuterated compound of any such compound.

2. The compound as recited in claim 1, wherein R is optionally substituted with one or two substituents independently selected from the following:

Lower alkyl, amine, substituted amine, alkoxy, hydroxyalkyl, halogen, hydroxy, carboxy, alkoxycarbonyl, haloalkyl, trifluoromethyl, trifluoromethyloxy, alkylamine, substituted alkylamine, carboxamide, thiocarboxamide, sulfonic acid, sulphate, acylamino, sulfonylamino, substituted or unsubstituted sulfonamide, substituted or unsubstituted urea, substituted or unsubstituted thiourea, oxyimino, hydroxamic acid, acyl, trifluoromethyl carbonyl, cyano, amidino, guanidino, aryloxy, heterocyclylalkyloxy, and heteroaryloxy.

3. The compound as recited in claim 1, which is selected from the following group of compounds:

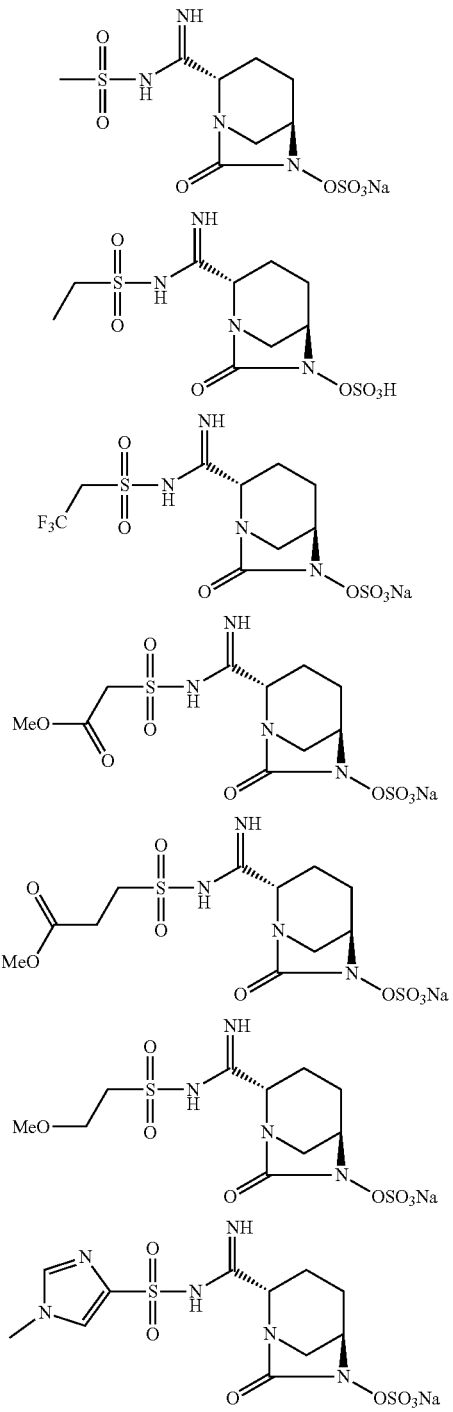

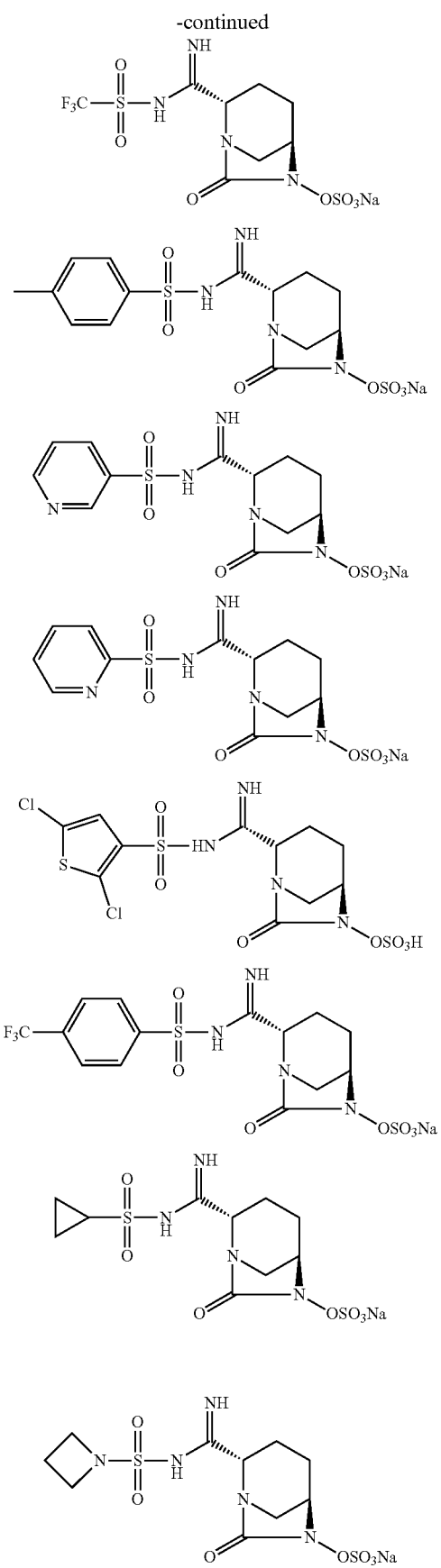
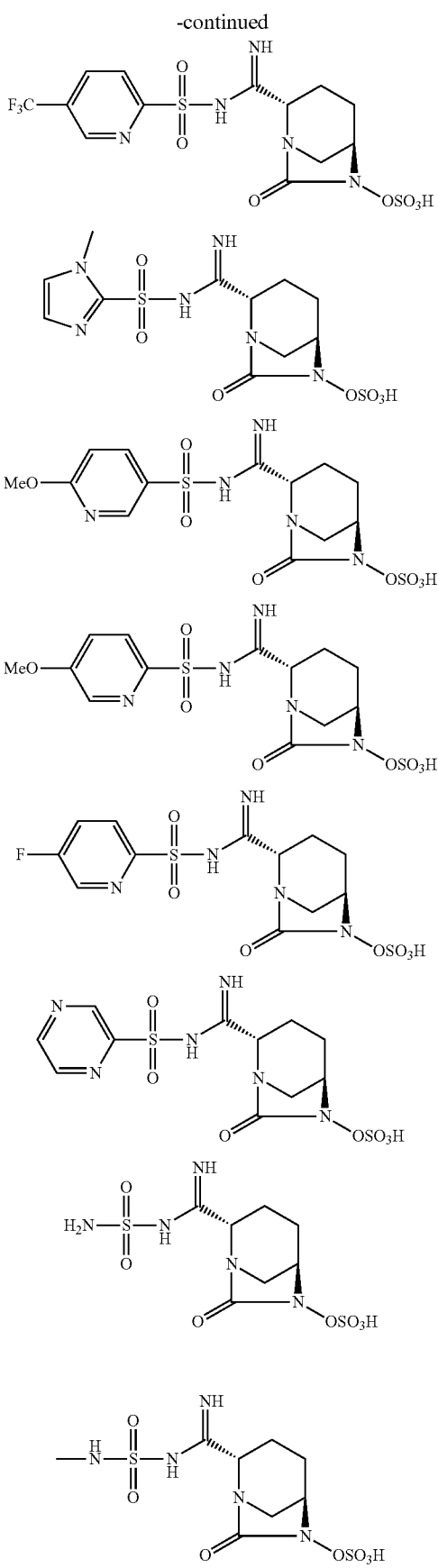

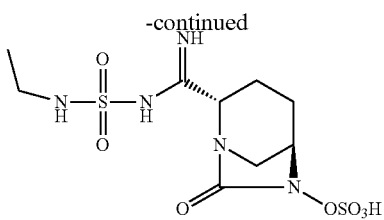

and pharmaceutically acceptable salts of such compounds, or deuterated compounds of such compounds and salts.

4. The compound as defined in claim 1, wherein the compound is selected from the group consisting of:
- (2S,5R)-2-(N-(methylsulfonyl)carbamimidoyl)-7-oxo-1,6-diazabicyclo[3.2.1]octan-6-yl hydrogen sulfate,
- (2S,5R)-2-(N-(tert-butylsulfonyl)carbamimidoyl)-7-oxo-1,6-diazabicyclo[3.2.1]octan-6-yl hydrogen sulfate,
- (2S,5R)-7-oxo-2-(N-((2,2,2-trifluoroethyl)sulfonyl)carbamimidoyl)-1,6-diazabicyclo[3.2.1]octan-6-yl hydrogen sulfate,
- (2S,5R)-2-(N-(ethylsulfonyl)carbamimidoyl)-7-oxo-1,6-diazabicyclo[3.2.1]octan-6-yl hydrogen sulfate,
- (2S,5R)-7-oxo-2-(N-(propylsulfonyl)carbamimidoyl)-1,6-diazabicyclo[3.2.1]octan-6-yl hydrogen sulfate,
- (2S,5R)-2-(N-(isopropylsulfonyl)carbamimidoyl)-7-oxo-1,6-diazabicyclo[3.2.1]octan-6-yl hydrogen sulfate,
- (2S,5R)-2-(N-((acetamidomethyl)sulfonyl)carbamimidoyl)-7-oxo-1,6-diazabicyclo[3.2.1]octan-6-yl hydrogen sulfate,
- (2S,5R)-2-(N-((aminomethyl)sulfonyl)carbamimidoyl)-7-oxo-1,6-diazabicyclo[3.2.1]octan-6-yl hydrogen sulfate,
- (2S,5R)-2-(N-((hydroxymethyl)sulfonyl)carbamimidoyl)-7-oxo-1,6-diazabicyclo[3.2.1]octan-6-yl hydrogen sulfate,
- (2S,5R)-7-oxo-2-(N-((ureidomethyl)sulfonyl)carbamimidoyl)-1,6-diazabicyclo[3.2.1]octan-6-yl hydrogen sulfate,
- 2-(N-(imino ((2S,5R)-7-oxo-6-(sulfooxy)-1,6-diazabicyclo[3.2.1]octan-2-yl)methyl)sulfamoyl) acetic acid,
- (2S,5R)-2-(N-((methoxymethyl)sulfonyl)carbamimidoyl)-7-oxo-1,6-diazabicyclo[3.2.1]octan-6-yl hydrogen sulfate,
- (2S,5R)-2-(N-((1-aminoethyl)sulfonyl)carbamimidoyl)-7-oxo-1,6-diazabicyclo[3.2.1]octan-6-yl hydrogen sulfate,
- (2S,5R)-2-(N-((2-amino-2-oxoethyl)sulfonyl)carbamimidoyl)-7-oxo-1,6-diazabicyclo[3.2.1]octan-6-yl hydrogen sulfate,
- (2S,5R)-2-(N-((2-morpholinoethyl)sulfonyl)carbamimidoyl)-7-oxo-1,6-diazabicyclo[3.2.1]octan-6-yl hydrogen sulfate,
- (2S,5R)-2-(N-((2-acetamidoethyl)sulfonyl)carbamimidoyl)-7-oxo-1,6-diazabicyclo[3.2.1]octan-6-yl hydrogen sulfate,
- (2S,5R)-7-oxo-2-(N-((2-(piperidin-1-yl)ethyl)sulfonyl)carbamimidoyl)-1,6-diazabicyclo[3.2.1]octan-6-yl hydrogen sulfate,
- (2S,5R)-2-(N-((2-(412-piperazin-1-yl)ethyl)sulfonyl)carbamimidoyl)-7-oxo-1,6-diazabicyclo[3.2.1]octan-6-yl hydrogen sulfate,
- (2S,5R)-2-(N-((2-methoxy-2-oxoethyl)sulfonyl)carbamimidoyl)-7-oxo-1,6-diazabicyclo[3.2.1]octan-6-yl hydrogen sulfate,
- (2S,5R)-2-(N-((3-methoxy-3-oxopropyl)sulfonyl)carbamimidoyl)-7-oxo-1,6-diazabicyclo[3.2.1]octan-6-yl hydrogen sulfate,
- (2S,5R)-2-(N-((2-methoxyethyl)sulfonyl)carbamimidoyl)-7-oxo-1,6-diazabicyclo[3.2.1]octan-6-yl hydrogen sulfate,
- (2S,5R)-2-(N-((2-acetamidoethyl)sulfonyl)carbamimidoyl)-7-oxo-1,6-diazabicyclo[3.2.1]octan-6-yl hydrogen sulfate,
- (2S,5R)-7-oxo-2-(N-((2-(piperidin-1-yl)ethyl)sulfonyl)carbamimidoyl)-1,6-diazabicyclo[3.2.1]octan-6-yl hydrogen sulfate,
- (2S,5R)-7-oxo-2-(N-((2-(piperazin-1-yl)ethyl)sulfonyl)carbamimidoyl)-1,6-diazabicyclo[3.2.1]octan-6-yl hydrogen sulfate,
- (2S,5R)-2-(N-(cyclopropylsulfonyl)carbamimidoyl)-7-oxo-1,6-diazabicyclo[3.2.1]octan-6-yl hydrogen sulfate,
- (2S,5R)-2-(N-(cyclobutylsulfonyl)carbamimidoyl)-7-oxo-1,6-diazabicyclo[3.2.1]octan-6-yl hydrogen sulfate,
- (2S,5R)-2-(N-(cyclopentylsulfonyl)carbamimidoyl)-7-oxo-1,6-diazabicyclo[3.2.1]octan-6-yl hydrogen sulfate,
- (2S,5R)-2-(N-((3-aminocyclopentyl)sulfonyl)carbamimidoyl)-7-oxo-1,6-diazabicyclo[3.2.1]octan-6-yl hydrogen sulfate,
- (2S,5R)-2-(N-((3-(dimethylamino)cyclopentyl)sulfonyl)carbamimidoyl)-7-oxo-1,6-diazabicyclo[3.2.1]octan-6-yl hydrogen sulfate,
- (2S,5R)-2-(N-((3-(methylamino)cyclopentyl)sulfonyl)carbamimidoyl)-7-oxo-1,6-diazabicyclo[3.2.1]octan-6-yl hydrogen sulfate,
- (2S,5R)-2-(N-((3-acetamidocyclopentyl)sulfonyl)carbamimidoyl)-7-oxo-1,6-diazabicyclo[3.2.1]octan-6-yl hydrogen sulfate,
- (2S,5R)-2-(N-((2-aminocyclopentyl)sulfonyl)carbamimidoyl)-7-oxo-1,6-diazabicyclo[3.2.1]octan-6-yl hydrogen sulfate,
- (2S,5R)-2-(N-((2-(dimethylamino)cyclopentyl)sulfonyl)carbamimidoyl)-7-oxo-1,6-diazabicyclo[3.2.1]octan-6-yl hydrogen sulfate,
- (2S,5R)-2-(N-((2-acetamidocyclopentyl)sulfonyl)carbamimidoyl)-7-oxo-1,6-diazabicyclo[3.2.1]octan-6-yl hydrogen sulfate,
- (2S,5R)-2-(N-((2-acetamidocyclopropyl)sulfonyl)carbamimidoyl)-7-oxo-1,6-diazabicyclo[3.2.1]octan-6-yl hydrogen sulfate,
- (2S,5R)-2-(N-((4-aminocyclohexyl)sulfonyl)carbamimidoyl)-7-oxo-1,6-diazabicyclo[3.2.1]octan-6-yl hydrogen sulfate,
- (2S,5R)-7-oxo-2-(N-(thiophen-2-ylsulfonyl)carbamimidoyl)-1,6-diazabicyclo[3.2.1]octan-6-yl hydrogen sulfate,
- (2S,5R)-7-oxo-2-(N-tosylcarbamimidoyl)-1,6-diazabicyclo[3.2.1]octan-6-yl hydrogen sulfate,
- (2S,5R)-7-oxo-2-(N-(pyridin-3-ylsulfonyl)carbamimidoyl)-1,6-diazabicyclo[3.2.1]octan-6-yl hydrogen sulfate,
- (2S,5R)-7-oxo-2-(N-((6-(trifluoromethyl)pyridin-3-yl)sulfonyl)carbamimidoyl)-1,6-diazabicyclo[3.2.1]octan-6-yl hydrogen sulfate,
- (2S,5R)-7-oxo-2-(N-(pyridin-4-ylsulfonyl)carbamimidoyl)-1,6-diazabicyclo[3.2.1]octan-6-yl hydrogen sulfate, (2S,5R)-2-(N-((1-methyl-1H-imidazol-4-yl)sulfonyl)carbamimidoyl)-7-oxo-1,6-diazabicyclo[3.2.1]octan-6-yl hydrogen sulfate, (2S,5R)-2-(N-((6-fluoropyridin-3-yl)sulfonyl)carbamimidoyl)-7-oxo-1,6-diazabicyclo[3.2.1]octan-6-yl hydrogen sulfate, (2S,5R)-2-(N-(oxazol-4-ylsulfonyl)carbamimidoyl)-7-oxo-1,6-diazabicyclo[3.2.1]octan-6-yl hydrogen sulfate, (2S,5R)-2-(N-(oxazol-5-ylsulfonyl)carbamimidoyl)-7-oxo-1,6-diazabicyclo[3.2.1]octan-6-yl hydrogen sulfate, (2S,5R)-7-oxo-2-(N-((2-(trifluoromethyl) thiazol-4-yl)sulfonyl)carbamimidoyl)-1,6-diazabicyclo[3.2.1]octan-6-yl hydrogen sulfate, (2S,5R)-2-(N-((2-aminothiazol-4-yl)sulfonyl)carbamimidoyl)-7-oxo-1,6-diazabicyclo[3.2.1]octan-6-yl hydrogen sulfate, (2S,5R)-7-oxo-2-(N-(thiazol-5-ylsulfonyl)carbamimidoyl)-1,6-diazabicyclo[3.2.1]octan-6-yl hydrogen sulfate, (2S,5R)-2-(N-((4-cyanophenyl)sulfonyl)carbamimidoyl)-7-oxo-1,6-diazabicyclo[3.2.1]octan-6-yl hydrogen sulfate, (2S,5R)-7-oxo-2-(N-(thiazol-2-ylsulfonyl)carbamimidoyl)-1,6-diazabicyclo[3.2.1]octan-6-yl hydrogen sulfate, (2S,5R)-7-oxo-2-(N-((5-(trifluoromethyl)pyridin-2-yl)sulfonyl)carbamimidoyl)-1,6-diazabicyclo[3.2.1]octan-6-yl hydrogen sulfate, (2S,5R)-2-(N-((4-fluorophenyl)sulfonyl)carbamimidoyl)-7-oxo-1,6-diazabicyclo[3.2.1]octan-6-yl hydrogen sulfate, (2S,5R)-7-oxo-2-(N-((6-(perfluoroethyl)pyridin-3-yl)sulfonyl)carbamimidoyl)-1,6-diazabicyclo[3.2.1]octan-6-yl hydrogen sulfate, (2S,5R)-7-oxo-2-(N-((4-(trifluoromethyl)phenyl)sulfonyl)carbamimidoyl)-1,6-diazabicyclo[3.2.1]octan-6-yl hydrogen sulfate, (2S,5R)-7-oxo-2-(N-(thiazol-4-ylsulfonyl)carbamimidoyl)-1,6-diazabicyclo[3.2.1]octan-6-yl hydrogen sulfate, (2S,5R)-7-oxo-2-(N-(pyrimidin-5-ylsulfonyl)carbamimidoyl)-1,6-diazabicyclo[3.2.1]octan-6-yl hydrogen sulfate, (2S,5R)-7-oxo-2-(N-(pyrimidin-4-ylsulfonyl)carbamimidoyl)-1,6-diazabicyclo[3.2.1]octan-6-yl hydrogen sulfate, (2S,5R)-2-(N-((5-fluoropyrimidin-2-yl)sulfonyl)carbamimidoyl)-7-oxo-1,6-diazabicyclo[3.2.1]octan-6-yl hydrogen sulfate, (2S,5R)-7-oxo-2-(N-((2-(trifluoromethyl)pyrimidin-5-yl)sulfonyl)carbamimidoyl)-1,6-diazabicyclo[3.2.1]octan-6-yl hydrogen sulfate, (2S,5R)-7-oxo-2-(N-((5-(trifluoromethyl)pyrimidin-2-yl)sulfonyl)carbamimidoyl)-1,6-diazabicyclo[3.2.1]octan-6-yl hydrogen sulfate, (2S,5R)-7-oxo-2-(N-(pyridin-2-ylsulfonyl)carbamimidoyl)-1,6-diazabicyclo[3.2.1]octan-6-yl hydrogen sulfate, (2S,5R)-2-(N-((1-methyl-1H-1,2,4-triazol-3-yl)sulfonyl)carbamimidoyl)-7-oxo-1,6-diazabicyclo[3.2.1]octan-6-yl hydrogen sulfate, (2S,5R)-2-(N-(isoxazol-3-ylsulfonyl)carbamimidoyl)-7-oxo-1,6-diazabicyclo[3.2.1]octan-6-yl hydrogen sulfate, (2S,5R)-2-(N-(isoxazol-4-ylsulfonyl)carbamimidoyl)-7-oxo-1,6-diazabicyclo[3.2.1]octan-6-yl hydrogen sulfate, (2S,5R)-2-(N-((1,2,4-oxadiazol-3-yl)sulfonyl)carbamimidoyl)-7-oxo-1,6-diazabicyclo[3.2.1]octan-6-yl hydrogen sulfate, (2S,5R)-2-(N-((5-methylisoxazol-4-yl)sulfonyl)carbamimidoyl)-7-oxo-1,6-diazabicyclo[3.2.1]octan-6-yl hydrogen sulfate, (2S,5R)-2-(N-((1,2,5-oxadiazol-3-yl)sulfonyl)carbamimidoyl)-7-oxo-1,6-diazabicyclo[3.2.1]octan-6-yl hydrogen sulfate, (2S,5R)-2-(N-((4-methyl-4H-1,2,4-triazol-3-yl)sulfonyl)carbamimidoyl)-7-oxo-1,6-diazabicyclo[3.2.1]octan-6-yl hydrogen sulfate, (2S,5R)-2-(N-((1-methyl-1H-1,2,3-triazol-4-yl)sulfonyl)carbamimidoyl)-7-oxo-1,6-diazabicyclo[3.2.1]octan-6-yl hydrogen sulfate, (2S,5R)-7-oxo-2-(N-((trifluoromethyl)sulfonyl)carbamimidoyl)-1,6-diazabicyclo[3.2.1]octan-6-yl hydrogen sulfate, (2S,5R)-2-(N-((difluoromethyl)sulfonyl)carbamimidoyl)-7-oxo-1,6-diazabicyclo[3.2.1]octan-6-yl hydrogen sulfate, (2S,5R)-2-(N-((fluoromethyl)sulfonyl)carbamimidoyl)-7-oxo-1,6-diazabicyclo[3.2.1]octan-6-yl hydrogen sulfate, (2S,5R)-2-(N-((2,5-dichlorothiophen-3-yl)sulfonyl)carbamimidoyl)-7-oxo-1,6-diazabicyclo[3.2.1]octan-6-yl hydrogen sulfate, (2S,5R)-2-(N-(furan-2-ylsulfonyl)carbamimidoyl)-7-oxo-1,6-diazabicyclo[3.2.1]octan-6-yl hydrogen sulfate, (2S,5R)-7-oxo-2-(N-sulfamoylcarbamimidoyl)-1,6-diazabicyclo[3.2.1]octan-6-yl hydrogen sulfate, (2S,5R)-2-(N—(N-methylsulfamoyl)carbamimidoyl)-7-oxo-1,6-diazabicyclo[3.2.1]octan-6-yl hydrogen sulfate, (2S,5R)-2-(N—(N-(acetamidomethyl)sulfamoyl)carbamimidoyl)-7-oxo-1,6-diazabicyclo[3.2.1]octan-6-yl hydrogen sulfate, (2S,5R)-2-(N—(N-(aminomethyl)sulfamoyl)carbamimidoyl)-7-oxo-1,6-diazabicyclo[3.2.1]octan-6-yl hydrogen sulfate, (2S,5R)-2-(N—(N-ethylsulfamoyl)carbamimidoyl)-7-oxo-1,6-diazabicyclo[3.2.1]octan-6-yl hydrogen sulfate, (2S,5R)-2-(N-(azetidin-1-ylsulfonyl)carbamimidoyl)-7-oxo-1,6-diazabicyclo[3.2.1]octan-6-yl hydrogen sulfate, (2S,5R)-2-(N—(((R)-1-acetylpyrrolidin-3-yl)sulfonyl)carbamimidoyl)-7-oxo-1,6-diazabicyclo[3.2.1]octan-6-yl hydrogen sulfate, (2S,5R)-2-(N-((1-methylpiperidin-4-yl)sulfonyl)carbamimidoyl)-7-oxo-1,6-diazabicyclo[3.2.1]octan-6-yl hydrogen sulfate, (2S,5R)-2-(N—(((S)-1-acetylpyrrolidin-3-yl)sulfonyl)carbamimidoyl)-7-oxo-1,6-diazabicyclo[3.2.1]octan-6-yl hydrogen sulfate, (2S,5R)-2-(N—(((S)-1-methylpyrrolidin-3-yl)sulfonyl)carbamimidoyl)-7-oxo-1,6-diazabicyclo[3.2.1]octan-6-yl hydrogen sulfate, (2S,5R)-2-(N-((1-acetylpiperidin-4-yl)sulfonyl)carbamimidoyl)-7-oxo-1,6-diazabicyclo[3.2.1]octan-6-yl hydrogen sulfate, (2S,5R)-2-(N—(((S)-1-(methylsulfonyl)pyrrolidin-3-yl)sulfonyl)carbamimidoyl)-7-oxo-1,6-diazabicyclo[3.2.1]octan-6-yl hydrogen sulfate, (2S,5R)-2-(N—(((R)-1-(methylsulfonyl)pyrrolidin-3-yl)sulfonyl)carbamimidoyl)-7-oxo-1,6-diazabicyclo[3.2.1]octan-6-yl hydrogen sulfate, (2S,5R)-2-(N-((1-(methylsulfonyl)piperidin-3-yl)sulfonyl)carbamimidoyl)-7-oxo-1,6-diazabicyclo[3.2.1]octan-6-yl hydrogen sulfate, (2S,5R)-2-(N—(N-isopropylsulfamoyl)carbamimidoyl)-7-oxo-1,6-diazabicyclo[3.2.1]octan-6-yl hydrogen sulfate, (2S,5R)-2-(N—(N-methyl-N-(2,2,2-trifluoroethyl)sulfamoyl)carbamimidoyl)-7-oxo-1,6-diazabicyclo[3.2.1]octan-6-yl hydrogen sulfate, (2S,5R)-2-(N—(N-isobutyl-N-methylsulfamoyl)carbamimidoyl)-7-oxo-1,6-diazabicyclo[3.2.1]octan-6-yl hydrogen sulfate, (2S,5R)-2-(N—(N-(tert-butyl)sulfamoyl)carbamimidoyl)-7-oxo-1,6-diazabicyclo[3.2.1]octan-6-yl hydrogen sulfate, (2S,5R)-2-(N—(N-(methoxycarbonyl)sulfamoyl)carbamimidoyl)-7-oxo-1,6-diazabicyclo[3.2.1]octan-6-yl hydrogen sulfate, (2S,5R)-2-(N-(isocyanatosulfonyl)carbamimidoyl)-7-oxo-1,6-diazabicyclo[3.2.1]octan-6-yl hydrogen sulfate, (2S,5R)-2-(N—(N-(2-cyanoethyl)-N-methylsulfamoyl)carbamimidoyl)-7-oxo-1,6-diazabicyclo[3.2.1]octan-6-yl hydrogen sulfate, (2S,5R)-2-(N—(N-ethyl-N-methylsulfamoyl)carbamimidoyl)-7-oxo-1,6-diazabicyclo[3.2.1]octan-6-yl hydrogen sulfate, (2S,5R)-2-(N—(N-(2-chloroethyl)sulfamoyl)carbamimidoyl)-7-oxo-1,6-diazabicyclo[3.2.1]octan-6-yl hydrogen sulfate, (2S,5R)-7-oxo-2-(N—(N-propionylsulfamoyl)carbamimidoyl)-1,6-diazabicyclo[3.2.1]octan-6-yl hydrogen sulfate, methyl 4-(N-(imino ((2S,5R)-7-oxo-6-(sulfooxy)-1,6-diazabicyclo[3.2.1]octan-2-yl)methyl)sulfamoyl)piperazine-1-carboxylate, (2S,5R)-2-(N-((4-methylpiperazin-1-yl)sulfonyl)carbamimidoyl)-7-oxo-1,6-diazabicyclo[3.2.1]octan-6-yl hydrogen sulfate, (2S,5R)-2-(N-((4-acetylpiperazin-1-yl)sulfonyl)carbamimidoyl)-7-oxo-1,6-diazabicyclo[3.2.1]octan-6-yl hydrogen sulfate, (2S,5R)-2-(N-((1-methyl-1H-imidazol-2-yl)sulfonyl)carbamimidoyl)-7-oxo-1,6-diazabicyclo[3.2.1]octan-6-yl hydrogen sulfate, (2S,5R)-2-(N-((6-methoxypyridin-3-yl)sulfonyl)carbamimidoyl)-7-oxo-1,6-diazabicyclo[3.2.1]octan-6-yl hydrogen sulfate, (2S,5R)-2-(N-((5-methoxypyridin-2-yl)sulfonyl)carbamimidoyl)-7-oxo-1,6-diazabicyclo[3.2.1]octan-6-yl hydrogen sulfate, (2S,5R)-2-(N-((5-fluoropyridin-2-yl)sulfonyl)carbamimidoyl)-7-oxo-1,6-diazabicyclo[3.2.1]octan-6-yl hydrogen sulfate, (2S,5R)-7-oxo-2-(N-(pyrazin-2-ylsulfonyl)carbamimidoyl)-1,6-diazabicyclo[3.2.1]octan-6-yl hydrogen sulfate or pharmaceutically acceptable salts of such compounds, and deuterated compounds of such compounds and salts.

5. A method of treating a bacterial infection comprising administering to a mammal in need thereof an antibacterially effective amount of a compound as recited in claim 1.

6. A pharmaceutical composition containing, as an active ingredient, at least one compound recited in claim 1.

7. A pharmaceutical composition containing, as an active ingredient, (i) at least one compound as recited in claim 1 and (ii) at least one β-lactam antibiotic, at least one salt of a β-lactam antibiotic, at least one hydrate of a β-lactam antibiotic, or at least one prodrug of a β-lactam antibiotic.

8. The pharmaceutical composition of claim 7, wherein a ratio of the weight of (i) the compound of formula (I) to the weight of (ii) at least one β-lactam antibiotic, at least one salt of a β-lactam antibiotic, at least one hydrate of a β-lactam antibiotic or at least one prodrug of a β-lactam antibiotic, is in the range of 1:30 to 30:1.

9. A pharmaceutical composition containing, as an active ingredient, (i) at least one compound as recited in claim 1 and (ii) at least one antibiotic, at least one salt of an antibiotic, at least one hydrate of an antibiotic, or at least one prodrug of an antibiotic.

10. The pharmaceutical composition of claim 9, wherein a ratio of the weight of (i) the compound of formula (I) to the weight of (ii) at least one antibiotic, at least one salt of an antibiotic, at least one hydrate of an antibiotic or at least one prodrug of an antibiotic, is in the range of 1:30 to 30:1.

11. The pharmaceutical composition of claim 7, further comprising a pharmaceutically acceptable carrier.

12. A method of treating a bacterial infection, which comprises administering to a mammal in need thereof a combination of (i) an effective amount of a compound as recited in claim 1 and (ii) an effective amount of at least one β-lactam antibiotic, at least one salt of a β-lactam antibiotic, at least one hydrate of a β-lactam antibiotic, or at least one prodrug of a β-lactam antibiotic.

13. The method of claim 12, wherein a ratio of the weight of (i) the compound of formula (I) to the weight of (ii) at least one β-lactam antibiotic, at least one salt of a β-lactam antibiotic, at least one hydrate of a β-lactam antibiotic or at least one prodrug of a β-lactam antibiotic, is in the range of 1:30 to 30:1.

14. A method of treating a bacterial infection, which comprises administering to a mammal in need thereof a combination of (i) an effective amount of a compound as recited in claim 1 and (ii) an effective amount of at least one antibiotic, at least one salt of an antibiotic, at least one hydrate of an antibiotic or at least one prodrug of an antibiotic.

15. The method of claim 14, wherein a ratio of the weight of (i) the compound of formula (I) to the weight of (ii) at least one antibiotic, at least one salt of an antibiotic, at least one hydrate of an antibiotic or at least one prodrug of an antibiotic, is in the range of 1:30 to 30:1.

16. A molecular complex comprising a compound as recited in claim 1 and at least one solvent, wherein the solvent comprises water.

17. The method of claim 14, wherein the mammal is a human.

18. A process for preparing a compound recited in claim 1, comprising: step A, the reaction of ammonium with the nitrile (C-1) in presence of a reagent selected from the group consisting of trimethylaluminum, triethylaluminum, Lanthanum (III) or trifluoromethanesulfonate, or a combination thereof, to provide an intermediate of formula (C-2), which is converted to an intermediate amide of formula (C-3) by coupling with proper sulfonyl chloride (R—SO₂Cl) or sulfonic anhydride (R—SO₂—O—SO₂—R) in presence of one or more suitable coupling reagents;

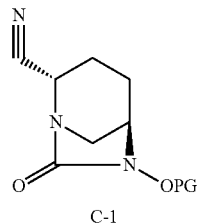
C-1

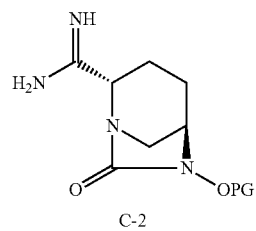
C-2

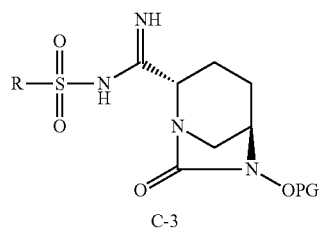
C-3 step B, removing the protecting group (PG) of the intermediate (C-3) to provide deprotection compound (C-4);

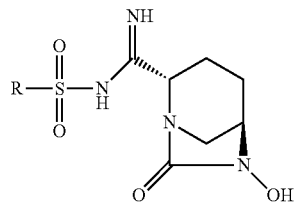
C-4 step C, contacting compound (C-4) with a sulfating reagent to obtain a compound of formula (I) after removal of protection group only when R contains a protecting group;

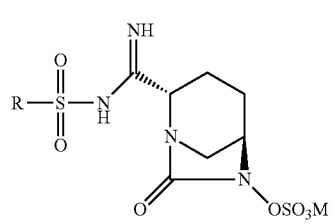
I wherein R and M are recited as in claim 1.

* * * * *